United States Patent
Hodorek et al.

(10) Patent No.: US 11,432,933 B2
(45) Date of Patent: Sep. 6, 2022

(54) HUMERAL IMPLANT ANCHOR SYSTEM

(71) Applicant: HOWMEDICA OSTEONICS CORP., Mahwah, NJ (US)

(72) Inventors: Brian C. Hodorek, Winona Lake, IN (US); Kevin P. Knox, Fort Wayne, IN (US); Thomas Bradley Edwards, Houston, TX (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 0 days.

(21) Appl. No.: 16/740,314

(22) Filed: Jan. 10, 2020

(65) Prior Publication Data

US 2020/0146834 A1    May 14, 2020

Related U.S. Application Data

(63) Continuation of application No. 16/580,367, filed on Sep. 24, 2019, which is a continuation of application
(Continued)

(51) Int. Cl.
*A61F 2/40* (2006.01)
*A61F 2/46* (2006.01)
(Continued)

(52) U.S. Cl.
CPC ........ *A61F 2/4014* (2013.01); *A61B 17/1684* (2013.01); *A61B 17/1778* (2016.11);
(Continued)

(58) Field of Classification Search
CPC .......... A61F 2002/30332; A61F 2/3859; A61F 2/4081; A61F 2/40; A61F 2002/30604;
(Continued)

(56) References Cited

U.S. PATENT DOCUMENTS

| 448,126 A | 3/1891 | Craig |
|---|---|---|
| 1,065,456 A | 6/1913 | Lowrey |

(Continued)

FOREIGN PATENT DOCUMENTS

| DE | 4220217 | 12/1993 |
|---|---|---|
| DE | 10233204 | 1/2004 |

(Continued)

OTHER PUBLICATIONS

Barth, et al., "Is global humeral head offset related to intramedullary canal width? A computer tomography morphometric study," Journal of Experimental Orthopaedics, 2018, vol. 5, pp. 1-8.
(Continued)

*Primary Examiner* — Ann Schillinger
(74) *Attorney, Agent, or Firm* — Duane Morris LLP

(57) ABSTRACT

A stemless humeral shoulder assembly having a base member and an anchor advanceable into the base member. The base member can include a distal end that can be embedded in bone and a proximal end that can be disposed at a bone surface. The base member can also have a plurality of spaced apart arms projecting from the proximal end to the distal end. The anchor can project circumferentially into the arms and into a space between the arms. When the anchor is advanced into the base member, the anchor can be exposed between the arms. A recess can project distally from a proximal end of the anchor to within the base member. The recess can receive a mounting member of an anatomical or reverse joint interface.

23 Claims, 50 Drawing Sheets

Related U.S. Application Data

No. 15/192,628, filed on Jun. 24, 2016, now Pat. No. 10,456,264, which is a continuation-in-part of application No. PCT/US2014/072443, filed on Dec. 26, 2014.

(60) Provisional application No. 61/931,500, filed on Jan. 24, 2014, provisional application No. 62/192,797, filed on Jul. 15, 2015.

(51) Int. Cl.
    A61F 2/30      (2006.01)
    A61B 17/86     (2006.01)
    A61B 17/17     (2006.01)
    A61B 17/16     (2006.01)

(52) U.S. Cl.
    CPC .......... A61F 2/4003 (2013.01); A61F 2/4059 (2013.01); A61F 2/3094 (2013.01); A61F 2/4612 (2013.01); A61F 2/4637 (2013.01); A61F 2002/30289 (2013.01); A61F 2002/30405 (2013.01); A61F 2002/30408 (2013.01); A61F 2002/4007 (2013.01); A61F 2002/4018 (2013.01); A61F 2002/4062 (2013.01); A61F 2002/4074 (2013.01); A61F 2220/0008 (2013.01)

(58) Field of Classification Search
    CPC .................. A61F 2/4014; A61F 2/4059; A61F 2002/0888; A61F 2220/0008; A61F 2002/0882; A61F 2002/3085; A61F 2002/3822; A61F 2002/4018; A61F 2002/4051; A61F 2002/4085
    See application file for complete search history.

(56) References Cited

U.S. PATENT DOCUMENTS

| | | |
|---|---|---|
| 1,123,730 A | 1/1915 | Greenfield |
| 2,444,099 A | 6/1948 | Hennessey, Jr. |
| 2,886,081 A | 5/1959 | Cowley |
| 3,523,395 A | 8/1970 | Rutter et al. |
| 3,609,056 A | 9/1971 | Hougen |
| 3,738,217 A | 6/1973 | Walker |
| 4,042,980 A | 8/1977 | Swanson et al. |
| 4,147,464 A | 4/1979 | Watson et al. |
| 4,250,600 A | 2/1981 | Gunther |
| 4,261,062 A | 4/1981 | Amstutz et al. |
| 4,406,023 A | 9/1983 | Harris |
| 4,550,450 A | 11/1985 | Kinnett |
| 4,601,289 A | 7/1986 | Chiarizzio et al. |
| 4,623,353 A | 11/1986 | Buechel et al. |
| 4,632,111 A | 12/1986 | Roche |
| 4,743,262 A | 5/1988 | Tronzo |
| 4,865,605 A | 9/1989 | Dines et al. |
| 4,883,491 A | 11/1989 | Mallory et al. |
| 4,919,670 A | 4/1990 | Dale et al. |
| 4,964,865 A | 10/1990 | Burkhead et al. |
| 4,986,833 A | 1/1991 | Worland |
| 5,026,373 A | 6/1991 | Ray et al. |
| 5,032,132 A | 7/1991 | Matsen et al. |
| 5,044,393 A | 9/1991 | Jiles |
| 5,080,673 A | 1/1992 | Burkhead et al. |
| 5,112,338 A | 5/1992 | Anspach, III |
| 5,163,964 A | 11/1992 | Lazzeri et al. |
| 5,171,277 A | 12/1992 | Roger |
| 5,257,995 A | 11/1993 | Umber et al. |
| 5,282,865 A | 2/1994 | Dong |
| 5,358,526 A | 10/1994 | Tornier |
| 5,443,471 A | 8/1995 | Swajger |
| 5,489,309 A | 2/1996 | Lackey et al. |
| 5,489,310 A | 2/1996 | Mikhail |
| 5,507,817 A | 4/1996 | Craig et al. |
| 5,514,136 A | 5/1996 | Richelsoph |
| 5,534,006 A | 7/1996 | Szabo et al. |
| 5,540,697 A | 7/1996 | Rehmann et al. |
| 5,681,134 A | 10/1997 | Ebert |
| 5,702,486 A | 12/1997 | Craig et al. |
| 5,720,750 A | 2/1998 | Koller et al. |
| 5,723,018 A | 3/1998 | Cyprien et al. |
| 5,776,194 A | 7/1998 | Mikol et al. |
| 5,800,551 A | 9/1998 | Williamson et al. |
| 5,810,524 A | 9/1998 | Wirth, Jr. et al. |
| 5,820,315 A | 10/1998 | Collard |
| 5,830,215 A | 11/1998 | Incavo et al. |
| 5,849,015 A | 12/1998 | Haywood et al. |
| 5,954,727 A | 9/1999 | Collazo |
| 5,976,148 A | 11/1999 | Charpenet et al. |
| 6,045,582 A | 4/2000 | Prybyla |
| 6,063,124 A | 5/2000 | Amstutz |
| 6,099,214 A | 8/2000 | Lee et al. |
| 6,110,179 A | 8/2000 | Flivik et al. |
| 6,113,605 A | 9/2000 | Storer |
| 6,132,469 A | 10/2000 | Schroeder |
| 6,139,551 A | 10/2000 | Michelson et al. |
| 6,146,423 A | 11/2000 | Cohen et al. |
| 6,174,335 B1 | 1/2001 | Varieur et al. |
| 6,187,012 B1 | 2/2001 | Masini |
| 6,197,063 B1 | 3/2001 | Dews |
| 6,264,299 B1 | 7/2001 | Noda |
| 6,264,657 B1 | 7/2001 | Urbahns et al. |
| 6,306,171 B1 | 10/2001 | Conzemius |
| 6,322,564 B1 | 11/2001 | Surma |
| 6,364,910 B1 | 4/2002 | Shultz et al. |
| 6,368,271 B1 | 4/2002 | Sharratt |
| 6,368,353 B1 | 4/2002 | Arcand |
| 6,379,917 B1 | 4/2002 | Okun et al. |
| 6,409,730 B1 | 6/2002 | Green et al. |
| 6,508,840 B1 | 1/2003 | Rockwood, Jr. et al. |
| 6,520,994 B2 | 2/2003 | Nogarin |
| 6,537,278 B1 | 3/2003 | Johnson |
| 6,626,913 B1 | 9/2003 | McKinnon et al. |
| 6,666,874 B2 | 12/2003 | Heitzmann et al. |
| 6,736,851 B2 | 5/2004 | Maroney et al. |
| 6,746,452 B2 | 6/2004 | Tuke et al. |
| 6,783,549 B1 | 8/2004 | Stone et al. |
| 6,786,684 B1 | 9/2004 | Ecker |
| 6,797,006 B2 | 9/2004 | Hodorek et al. |
| 7,044,973 B2 | 5/2006 | Rockwood, Jr. et al. |
| 7,097,663 B1 | 8/2006 | Nicol et al. |
| 7,140,087 B1 | 11/2006 | Giltner |
| 7,160,328 B2 | 1/2007 | Rockwood, Jr. et al. |
| 7,169,184 B2 | 1/2007 | Pria |
| 7,175,663 B1 | 2/2007 | Stone |
| 7,179,084 B1 | 2/2007 | Kometas |
| 7,189,036 B1 | 3/2007 | Watson |
| 7,189,261 B2 | 3/2007 | Dews et al. |
| 7,204,854 B2 | 4/2007 | Guederian et al. |
| 7,208,222 B2 | 4/2007 | Rolfe et al. |
| 7,344,565 B2 | 3/2008 | Seyer et al. |
| 7,465,319 B2 | 12/2008 | Tornier |
| 7,476,228 B2 | 1/2009 | Abou |
| 7,476,253 B1 | 1/2009 | Craig et al. |
| 7,585,327 B2 | 9/2009 | Winslow |
| 7,615,080 B2 | 11/2009 | Ondrla |
| 7,637,703 B2 | 12/2009 | Khangar et al. |
| 7,648,530 B2 | 1/2010 | Habermeyer et al. |
| 7,670,382 B2 | 3/2010 | Parrott et al. |
| 7,678,150 B2 | 3/2010 | Tornier et al. |
| 7,744,602 B2 | 6/2010 | Teeny et al. |
| 7,758,650 B2 | 7/2010 | Dews et al. |
| 7,887,544 B2 | 2/2011 | Tornier et al. |
| 7,927,376 B2 | 4/2011 | Leisinger et al. |
| D643,926 S | 8/2011 | Collins |
| 8,021,370 B2 | 9/2011 | Fenton et al. |
| 8,114,089 B2 | 2/2012 | Divoux et al. |
| 8,162,947 B2 | 4/2012 | Dreyfuss |
| 8,182,541 B2 | 5/2012 | Long et al. |
| 8,187,282 B2 | 5/2012 | Tornier et al. |
| 8,192,497 B2 | 6/2012 | Ondrla |
| 8,202,275 B2 | 6/2012 | Wozencroft |
| 8,221,037 B2 | 7/2012 | Neitzell |

(56) References Cited

U.S. PATENT DOCUMENTS

| | | |
|---|---|---|
| 8,231,682 B2 | 7/2012 | LaFosse |
| 8,246,687 B2 | 8/2012 | Katrana et al. |
| 8,262,667 B1 | 9/2012 | Silver et al. |
| 8,277,512 B2 | 10/2012 | Parrott et al. |
| 8,317,871 B2 | 11/2012 | Stone et al. |
| 8,409,798 B2 | 4/2013 | Luy et al. |
| 8,419,798 B2 | 4/2013 | Ondrla et al. |
| D685,474 S | 7/2013 | Courtney |
| 8,500,744 B2 | 8/2013 | Wozencroft et al. |
| 8,506,638 B2 | 8/2013 | Vanasse et al. |
| 8,512,410 B2 | 8/2013 | Metcalfe et al. |
| 8,591,592 B2 | 11/2013 | Dreyfuss |
| 8,641,773 B2 | 2/2014 | Bergin et al. |
| 8,647,387 B2 | 2/2014 | Winslow |
| 8,663,334 B2 | 3/2014 | Viscardi et al. |
| 8,690,958 B2 | 4/2014 | Klawitter et al. |
| 8,702,800 B2 | 4/2014 | Linares et al. |
| 8,753,402 B2 | 6/2014 | Winslow et al. |
| 8,795,379 B2 | 8/2014 | Smith et al. |
| 8,840,671 B2 | 9/2014 | Ambacher |
| 8,845,742 B2 | 9/2014 | Kusogullari et al. |
| 8,864,834 B2 | 10/2014 | Boileau et al. |
| 8,870,962 B2 | 10/2014 | Roche et al. |
| 8,876,908 B2 | 11/2014 | Katrana et al. |
| 8,882,845 B2 | 11/2014 | Wirth et al. |
| 8,992,623 B2 | 3/2015 | Hopkins et al. |
| D745,678 S | 12/2015 | Courtney et al. |
| 9,233,003 B2 | 1/2016 | Roche et al. |
| 9,289,218 B2 | 3/2016 | Courtney, Jr. et al. |
| 9,326,865 B2 | 5/2016 | Katrana et al. |
| 9,364,334 B2 | 6/2016 | Katrana et al. |
| 9,498,345 B2 | 11/2016 | Burkhead et al. |
| 9,510,839 B2 | 12/2016 | Maroney et al. |
| 9,603,712 B2 | 3/2017 | Bachmaier |
| 9,615,928 B2 | 4/2017 | Visser et al. |
| 9,820,859 B2 | 11/2017 | Gervasi et al. |
| 10,166,032 B2 | 1/2019 | Stone et al. |
| D840,539 S | 2/2019 | Courtney et al. |
| 10,335,285 B2 | 7/2019 | Viscardi et al. |
| 10,368,999 B2 | 8/2019 | Greiwe |
| 10,433,969 B2 | 10/2019 | Humphrey |
| 10,456,264 B2 * | 10/2019 | Hodorek ............... A61F 2/4014 |
| 10,463,499 B2 | 11/2019 | Emerick et al. |
| 10,898,348 B2 | 1/2021 | Vivanz et al. |
| 10,945,862 B2 | 3/2021 | Roby et al. |
| 11,076,962 B2 | 8/2021 | Kemp et al. |
| 11,229,524 B2 | 1/2022 | Sperling |
| 2001/0034553 A1 | 10/2001 | Michelson et al. |
| 2001/0047210 A1 | 11/2001 | Wolf |
| 2002/0116007 A1 | 8/2002 | Lewis |
| 2002/0156534 A1 | 10/2002 | Grusin et al. |
| 2003/0028253 A1 | 2/2003 | Stone et al. |
| 2003/0031521 A1 | 2/2003 | Haughton et al. |
| 2003/0114933 A1 | 6/2003 | Bouttens et al. |
| 2003/0125810 A1 | 7/2003 | Sullivan et al. |
| 2004/0010262 A1 | 1/2004 | Parkinson et al. |
| 2004/0049270 A1 | 3/2004 | Gewirtz |
| 2004/0186586 A1 | 9/2004 | Seyer et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0220674 A1 | 11/2004 | Pria |
| 2004/0243136 A1 | 12/2004 | Gupta et al. |
| 2004/0254646 A1 | 12/2004 | Stone et al. |
| 2005/0107882 A1 | 5/2005 | Stone et al. |
| 2005/0112397 A1 | 5/2005 | Rolfe et al. |
| 2005/0203539 A1 | 9/2005 | Grimm et al. |
| 2005/0209597 A1 | 9/2005 | Long et al. |
| 2005/0261775 A1 | 11/2005 | Baum et al. |
| 2005/0267478 A1 | 12/2005 | Corradi et al. |
| 2006/0004378 A1 | 1/2006 | Raines |
| 2006/0009852 A1 | 1/2006 | Winslow et al. |
| 2006/0020344 A1 | 1/2006 | Shultz et al. |
| 2006/0064173 A1 | 3/2006 | Guederian |
| 2006/0089656 A1 | 4/2006 | Allard et al. |
| 2006/0142866 A1 | 6/2006 | Baratz et al. |
| 2006/0195105 A1 | 8/2006 | Teeny et al. |
| 2006/0200165 A1 | 9/2006 | Tulkis |
| 2006/0200249 A1 * | 9/2006 | Beguin ................ A61F 2/4014 623/19.14 |
| 2007/0010825 A1 | 1/2007 | Leisinger et al. |
| 2007/0100458 A1 | 5/2007 | Dalla Pria |
| 2007/0123890 A1 | 5/2007 | Way et al. |
| 2007/0123893 A1 | 5/2007 | O'Donoghue |
| 2007/0123909 A1 | 5/2007 | Rupp et al. |
| 2007/0156246 A1 | 7/2007 | Meswania et al. |
| 2007/0162038 A1 | 7/2007 | Tuke |
| 2007/0162141 A1 | 7/2007 | Dews et al. |
| 2007/0173945 A1 | 7/2007 | Wiley et al. |
| 2007/0212179 A1 | 9/2007 | Khangar et al. |
| 2007/0219562 A1 | 9/2007 | Slone et al. |
| 2007/0233132 A1 | 10/2007 | Valla |
| 2007/0288096 A1 | 12/2007 | Surma |
| 2008/0021564 A1 | 1/2008 | Gunther |
| 2008/0077146 A1 | 3/2008 | Pernsteiner et al. |
| 2008/0172061 A1 | 7/2008 | Ragbir |
| 2008/0195111 A1 | 8/2008 | Anderson |
| 2008/0221576 A1 | 9/2008 | Keller |
| 2008/0249577 A1 | 10/2008 | Dreyfuss |
| 2009/0171462 A1 | 7/2009 | Poncet et al. |
| 2009/0281630 A1 | 11/2009 | Delince et al. |
| 2009/0306782 A1 | 12/2009 | Schwyzer |
| 2010/0042214 A1 | 2/2010 | Nebosky et al. |
| 2010/0087927 A1 | 4/2010 | Roche et al. |
| 2010/0114326 A1 * | 5/2010 | Winslow ............... A61F 2/3603 623/23.42 |
| 2010/0121331 A1 | 5/2010 | Sharp et al. |
| 2010/0191340 A1 | 7/2010 | Dreyfuss |
| 2010/0268238 A1 | 10/2010 | Sikora et al. |
| 2010/0274359 A1 * | 10/2010 | Brunnarius ......... A61F 2/30734 623/19.13 |
| 2010/0274360 A1 | 10/2010 | Gunther |
| 2010/0278601 A1 | 11/2010 | Beynon |
| 2010/0331902 A1 | 12/2010 | Biegun |
| 2011/0082587 A1 | 4/2011 | Ziaei et al. |
| 2011/0153023 A1 * | 6/2011 | Deffenbaugh ........ A61F 2/4081 623/19.11 |
| 2011/0224673 A1 | 9/2011 | Smith |
| 2011/0276144 A1 | 11/2011 | Wirth et al. |
| 2011/0313533 A1 | 12/2011 | Gunther |
| 2012/0022664 A1 | 1/2012 | Vandermeulen et al. |
| 2012/0083769 A1 | 4/2012 | Burgi et al. |
| 2012/0109321 A1 | 5/2012 | Stone et al. |
| 2012/0184964 A1 | 7/2012 | Hudak, Jr. et al. |
| 2012/0221111 A1 | 8/2012 | Burkhead, Jr. et al. |
| 2012/0232562 A1 | 9/2012 | Mani et al. |
| 2012/0265315 A1 * | 10/2012 | Kusogullari .......... A61F 2/4003 623/19.14 |
| 2012/0265319 A1 | 10/2012 | Prybyla et al. |
| 2012/0277880 A1 | 11/2012 | Winslow et al. |
| 2012/0290099 A1 | 11/2012 | Gibson et al. |
| 2012/0296435 A1 | 11/2012 | Ambacher |
| 2013/0018382 A1 | 1/2013 | Jones et al. |
| 2013/0018476 A1 * | 1/2013 | Katrana ................ A61F 2/4014 623/19.14 |
| 2013/0123929 A1 | 5/2013 | McDaniel et al. |
| 2013/0123930 A1 | 5/2013 | Burt |
| 2013/0150972 A1 * | 6/2013 | Iannotti ................ A61F 2/4059 623/18.11 |
| 2013/0173006 A1 | 7/2013 | Duport |
| 2013/0178943 A1 | 7/2013 | Duport |
| 2013/0190882 A1 | 7/2013 | Humphrey |
| 2013/0211539 A1 * | 8/2013 | McDaniel ................ A61F 2/28 623/23.53 |
| 2013/0261626 A1 | 10/2013 | Chavarria et al. |
| 2013/0261629 A1 * | 10/2013 | Anthony ............... A61F 2/4003 606/80 |
| 2013/0261630 A1 | 10/2013 | Courtney, Jr. et al. |
| 2013/0261754 A1 | 10/2013 | Anthony et al. |
| 2013/0261755 A1 * | 10/2013 | Anthony ............... A61F 2/4684 623/19.14 |
| 2013/0282129 A1 | 10/2013 | Phipps |
| 2013/0331849 A1 | 12/2013 | Splieth et al. |

(56) References Cited

U.S. PATENT DOCUMENTS

| | | |
|---|---|---|
| 2014/0012272 A1 | 1/2014 | Leisinger |
| 2014/0012380 A1 | 1/2014 | Laurence et al. |
| 2014/0058523 A1 | 2/2014 | Walch et al. |
| 2014/0074246 A1 | 3/2014 | Huebner et al. |
| 2014/0107792 A1 | 4/2014 | Hopkins et al. |
| 2014/0156012 A1 | 6/2014 | Winslow |
| 2014/0236304 A1 | 8/2014 | Hodorek et al. |
| 2014/0257499 A1 | 9/2014 | Winslow et al. |
| 2014/0288657 A1 | 9/2014 | Lederman et al. |
| 2014/0296988 A1 | 10/2014 | Winslow et al. |
| 2014/0358239 A1 | 12/2014 | Katrana et al. |
| 2014/0358240 A1 | 12/2014 | Katrana et al. |
| 2014/0379089 A1 | 12/2014 | Bachmaier |
| 2015/0134066 A1 | 5/2015 | Bachmaier |
| 2015/0250601 A1 | 9/2015 | Humphrey |
| 2015/0289984 A1 | 10/2015 | Budge |
| 2015/0297354 A1 | 10/2015 | Walch et al. |
| 2015/0328015 A1 | 11/2015 | Olson et al. |
| 2016/0051367 A1 | 2/2016 | Gervasi et al. |
| 2016/0059403 A1 | 3/2016 | Mugnier |
| 2016/0157911 A1 | 6/2016 | Courtney, Jr. et al. |
| 2016/0206445 A1 | 7/2016 | Gheevarughese et al. |
| 2016/0324648 A1 | 11/2016 | Hodorek et al. |
| 2016/0331551 A1 | 11/2016 | Slade et al. |
| 2017/0105843 A1 | 4/2017 | Britton et al. |
| 2017/0112634 A1 | 4/2017 | Gunn et al. |
| 2017/0273800 A1 * | 9/2017 | Emerick ............... A61B 17/86 |
| 2017/0304063 A1 | 10/2017 | Hatzidakis et al. |
| 2017/0367714 A1 | 12/2017 | McCulloch et al. |
| 2017/0367836 A1 | 12/2017 | Cardon et al. |
| 2018/0028249 A1 | 2/2018 | Jaumard |
| 2018/0092757 A1 | 4/2018 | Behzadi et al. |
| 2018/0092760 A1 | 4/2018 | Sperling et al. |
| 2018/0103967 A1 | 4/2018 | Rouyer et al. |
| 2018/0161176 A1 | 6/2018 | Vivanz et al. |
| 2018/0193168 A1 | 7/2018 | Termanini et al. |
| 2018/0200067 A1 | 7/2018 | Axelson et al. |
| 2018/0206859 A1 | 7/2018 | Pendleton et al. |
| 2018/0271667 A1 | 9/2018 | Kemp et al. |
| 2019/0105165 A1 | 4/2019 | Sikora et al. |
| 2019/0105169 A1 | 4/2019 | Sperling |
| 2019/0159906 A1 | 5/2019 | Knox et al. |
| 2019/0175354 A1 | 6/2019 | Knox et al. |
| 2019/0216518 A1 | 7/2019 | Courtney, Jr. et al. |
| 2019/0231558 A1 | 8/2019 | Beck et al. |
| 2019/0328536 A1 | 10/2019 | Martin et al. |
| 2019/0336307 A1 | 11/2019 | Sungu et al. |
| 2019/0374349 A1 | 12/2019 | Müller |
| 2020/0000573 A1 | 1/2020 | Whittaker et al. |
| 2020/0008947 A1 | 1/2020 | Emerick et al. |
| 2020/0121467 A1 | 4/2020 | Hodorek et al. |
| 2020/0121474 A1 | 4/2020 | Pendleton et al. |
| 2020/0188125 A1 | 6/2020 | Hodorek et al. |
| 2020/0214845 A1 | 7/2020 | Knox et al. |
| 2020/0214853 A1 | 7/2020 | Sweitzer |
| 2020/0222205 A1 | 7/2020 | Gosik-Wolfe et al. |
| 2021/0030565 A1 | 2/2021 | Dun et al. |
| 2021/0045895 A1 | 2/2021 | Sapio et al. |
| 2021/0212840 A1 | 7/2021 | Sweitzer et al. |
| 2021/0212841 A1 | 7/2021 | Sweitzer et al. |
| 2021/0228370 A1 | 7/2021 | Ek et al. |
| 2021/0244487 A1 | 8/2021 | Beck |
| 2021/0251643 A1 | 8/2021 | Stump |
| 2021/0290411 A1 | 9/2021 | Gosik-Wolfe |
| 2021/0315713 A1 | 10/2021 | Keach et al. |
| 2021/0330476 A1 | 10/2021 | Alden |
| 2021/0338456 A1 | 11/2021 | Wolfe et al. |
| 2021/0386558 A1 | 12/2021 | Alden |
| 2021/0393414 A1 | 12/2021 | Robicheaux et al. |
| 2022/0023053 A1 | 1/2022 | Kim et al. |
| 2022/0023071 A1 | 1/2022 | Sweitzer |
| 2022/0104835 A1 | 4/2022 | Blaser et al. |
| 2022/0117756 A1 | 4/2022 | Blaser et al. |
| 2022/0125591 A1 | 4/2022 | Rivera, Jr. |
| 2022/0151794 A1 | 5/2022 | Fattori et al. |

FOREIGN PATENT DOCUMENTS

| | | | | |
|---|---|---|---|---|
| DE | 102004042502 | | 3/2006 | |
| EP | 0 274 094 | | 8/1990 | |
| EP | 1 413 265 | | 4/2004 | |
| EP | 0 959 822 | | 5/2004 | |
| EP | 1 125 565 | | 12/2004 | |
| EP | 1 518 519 | | 3/2005 | |
| EP | 1 004 283 | | 5/2005 | |
| EP | 1 639 967 | | 3/2006 | |
| EP | 1 762 191 | | 3/2007 | |
| EP | 1 952 788 | | 8/2008 | |
| EP | 1 867 303 | | 9/2010 | |
| EP | 1 977 720 | | 1/2011 | |
| EP | 1 550 420 | | 2/2012 | |
| EP | 2 261 303 | | 11/2012 | |
| EP | 1 706 074 | | 12/2012 | |
| EP | 2 564 814 | | 3/2013 | |
| EP | 2 567 676 | | 3/2013 | |
| EP | 2564814 A1 * | 3/2013 | ........... A61F 2/4003 |
| EP | 2 574 313 | | 4/2013 | |
| EP | 2586387 A1 | | 5/2013 | |
| EP | 2604227 A1 * | 6/2013 | ........... A61F 2/3603 |
| EP | 2 616 013 | | 7/2013 | |
| EP | 2 474 288 | | 9/2013 | |
| EP | 2 663 263 | | 5/2014 | |
| EP | 2 502 605 | | 8/2014 | |
| EP | 2 800 541 | | 11/2014 | |
| EP | 2 815 726 | | 8/2015 | |
| EP | 2 353 549 | | 6/2016 | |
| EP | 3 117 801 | | 1/2017 | |
| EP | 2 965 720 B1 | | 7/2017 | |
| FR | 2 674 122 | | 9/1992 | |
| FR | 2997290 B1 | | 11/2015 | |
| GB | 2405346 | | 3/2005 | |
| JP | 2009523578 A | | 6/2009 | |
| WO | WO 01/67988 | | 9/2001 | |
| WO | WO 02/17822 | | 3/2002 | |
| WO | WO 2008/011078 | | 1/2008 | |
| WO | WO 2008/146124 | | 12/2008 | |
| WO | WO 2011/081797 | | 7/2011 | |
| WO | WO 2012/035263 | | 3/2012 | |
| WO | WO 2012/130524 | | 10/2012 | |
| WO | WO 2013/009407 | | 1/2013 | |
| WO | WO 2013/064569 | | 5/2013 | |
| WO | WO 2013/148229 | | 10/2013 | |
| WO | WO 2014/005644 | | 1/2014 | |
| WO | WO 2014/058314 | | 4/2014 | |
| WO | WO 2015/112307 | | 7/2015 | |
| WO | 2016094739 A1 | | 6/2016 | |
| WO | WO 2016/094739 | | 6/2016 | |
| WO | WO 2017/165090 | | 9/2017 | |
| WO | WO 2017/184792 | | 10/2017 | |
| WO | WO 2018/022227 | | 2/2018 | |
| WO | WO 2019/060780 | | 3/2019 | |
| WO | WO 2019/106278 | | 6/2019 | |
| WO | WO 2020/072452 | | 4/2020 | |
| WO | WO 2020/072454 | | 4/2020 | |

OTHER PUBLICATIONS

Boileau, et al., "The Three-Dimensional Geometry of the Proximal Humerus: Implications for Surgical Technique and Prosthetic Design," J Bone Joint Surg, Sep. 1997, vol. 79-B, Issue 5, pp. 857-865.

Routman, et al., "Reverse Shoulder Arthroplasty Prosthesis Design Classification System," Bulletin of the Hospital for Joint Diseases, 2015, vol. 73 (Suppl 1), pp. S5-S14.

International Search Report and Written Opinion for PCT/US2014/072443 dated Mar. 24, 2015 in 12 pages.

Final Rejection issued in connection with U.S. Appl. No. 16/208,956, filed Apr. 30, 2021, 13 pages.

Non-Final Office Action issued in connection with U.S. Appl. No. 17/250,964, filed Jul. 26, 2021, 27 pages.

Final Rejection issued in connection with U.S. Appl. No. 17/250,964, filed Sep. 9, 2021, 22 pages.

Final Rejection issued in connection with U.S. Appl. No. 16/249,720, filed Aug. 20, 2021, 40 pages.

(56) References Cited

OTHER PUBLICATIONS

Final Rejection issued in connection with U.S. Appl. No. 16/580,367, filed Aug. 24, 2021, 9 pages.
Non-Final Office Action issued in connection with U.S. Appl. No. 17/250,964, filed Feb. 24, 2022, 12 pages.
First Office Action issued in connection with Japanese Patent Application No. 2019-555151, Feb. 21, 2022, 5 pages.
Non-Final Office Action issued in connection with U.S. Appl. No. 16/648,128, dated Mar. 28, 2022, 43 pages.
Office Action issued in connection with Japanese Patent Application No. 2021-518159, dated May 24, 2022, 5 pages.
Third Examination Report issued in connection with Australian Patent Application No. 2019355854, dated May 10, 2022, 4 pages.
First Examination Report issued in connection with Australian Patent Application No. 2021250994, dated Jun. 2, 2022, 5 pages.
Non-Final Office Action issued in connection with U.S. Appl. No. 17/717,253, filed Jun. 29, 2022, 56 pages.
Office Action issued in connection with Japanese Patent Application No. 2021-518174, dated May 24, 2022, 7 pages.

\* cited by examiner

HUMERAL IMPLANT ANCHOR SYSTEM

CROSS-REFERENCE TO RELATED APPLICATIONS

The present application is a continuation of U.S. patent application Ser. No. 16/580,367, filed Sep. 24, 2019, which is continuation of U.S. patent application Ser. No. 15/192,628, filed Jun. 24, 2016, now U.S. Pat. No. 10,456,264, which is a continuation-in-part of PCT Application No. PCT/US2014/072443, filed Dec. 26, 2014, which claims to the priority benefit of U.S. Provisional Application No. 61/931,500, filed Jan. 24, 2014, both of which are hereby incorporated by reference in their entirety herein. U.S. patent application Ser. No. 15/192,628 also claims the priority benefit of U.S. Provisional Application No. 62/192,797, filed Jul. 15, 2015, which is hereby incorporated by reference in its entirety herein.

BACKGROUND

Field

The present disclosure relates to stemmed and stemless humeral components of a shoulder joint prosthesis.

Description of the Related Art

In a shoulder joint, the head of the humerus interacts with the glenoid cavity of the scapula in a manner similar to a "ball and socket" joint. Over time, it may become necessary to replace the shoulder joint with a prosthetic shoulder joint including a humeral component.

Traditionally, the humeral component is a single body implant having a humeral head and a stem. The stem is configured to be inserted into an intramedullary canal of the humerus. In certain cases, insertion of the stem disadvantageously requires bone to be removed to fit the stem to the canal due to patient-to-patient anatomical variation. Another disadvantage of this approach is that integration of the stem into the bone through a natural process of bone ingrowth can make it difficult to remove the humeral component if it becomes necessary to replace the humeral component with another device. Even when no removal was expected, this approach had the disadvantage of only achieving implant security after sufficient time had passed to allow for sufficient bone ingrowth.

A stemless humeral component may be used to address some of the disadvantages of conventional humeral components. Stemless humeral components can decrease the amount of bone loss in preparing the humerus to receive the component and decrease the complexity of the joint replacement procedure.

Stemless humeral component designs can be more challenging to secure to the humerus. Conventional stemless designs rely on bone ingrowth for strength. While such designs perform well over time, there is a risk in the early days and weeks after surgery where such ingrowth has not yet occurred that the stem and stemless humeral component will be dislodged from the humerus. Dislodgement may also occur due to excessive wear, forces applied thereto during a revision surgery or other high load conditions.

SUMMARY

Accordingly, there is a need for a stemless humeral component or prosthesis designed to preserve bone in initial implantation while enhancing initial pull-out resistance. Preferably enhanced initial dislodgement resistance will also provide excellent long term fixation.

The present disclosure relates to various embodiments of a stemless humeral shoulder assembly that can minimize bone loss and provide excellent initial pull-out resistance and long term fixation. Advantageously, the humeral shoulder assemblies described herein provide adequate compression, increase rotational and longitudinal stability, and encourage bone ingrowth.

Certain aspects of the disclosure are directed toward a prosthesis mounting system having a base member adapted to be driven into bone. The base member can include a central portion having a lumen extending along a longitudinal axis and a peripheral portion connected to the central portion. Further, the prosthetic mounting system can include an anchor having an inner passage sized to be advanced along the longitudinal axis of the base member. The anchor can have at least one thread surrounding the inner passage. When the anchor is coupled with the base member, the thread extends outward of the central portion of the base member.

In one embodiment, a stemless humeral shoulder assembly is provided. The assembly includes a base member and an anchor member. The base member has a distal end that can be embedded in bone and a proximal end that can be disposed at a bone surface. The base member has a plurality of spaced apart arms projecting from the proximal end to the distal end. The anchor member is advanceable into the base member to a position disposed within the arms. The anchor member is configured to project circumferentially into the arms and into a space between the arms. The anchor member is exposed between the arms when advanced into the base member. The assembly includes a recess projecting distally from a proximal end of the anchor member to within the base member. The recess is configured to receive a mounting member of an anatomical or reverse joint interface.

In another embodiment, a humeral shoulder assembly is provided that includes a stem and an anchor. The stem has a proximal region to be disposed in the metaphysis of a humerus, a distal end configured to be disposed in a canal of a humerus and a proximal end. The proximal end is to be disposed at a bone surface. The proximal region of the stem has a plurality of spaced apart projections disposed adjacent to the proximal end. The anchor is advanceable into the stem to a position disposed within the projections. The anchor is configured to project circumferentially into the projections and into a space between the projections. The anchor is exposed between the projections when advanced into the stem. The humeral shoulder assembly includes a recess that projects distally from a proximal end of the anchor to within the stem. The recess is configured to couple with an articular component.

In another embodiment, a prosthesis mounting system is provided that includes a stem and an anchor. The stem is adapted to be driven into bone. The stem has a central portion that includes a lumen. The lumen extends along a longitudinal axis. A peripheral portion of the stem is connected to the central portion. The stem extends distally of the central portion. The anchor has an inner passage sized to be advanced along the longitudinal axis. The anchor having at least one thread surrounding the inner passage. When the anchor is coupled with a proximal portion of the stem, the thread extends outward of the central portion of the base member.

Certain aspects of the disclosure are directed toward methods for treating a shoulder joint. The methods can include accessing a humeral head, resecting the humeral head, driving a base member into the humeral head, and advancing an anchor member into the base member. When the anchor member is advanced into the base member, a lateral projection of the anchor member can be disposed through the base member and can be embedded in bone adjacent to the base member. In certain aspects, the methods can also include securing a joint interface to the base member and/or the anchor member.

In another method for treating a shoulder joint, an end portion of a humerus is accessed. A stem is driven into the end portion of the humerus such that a portion of the stem extends into a canal of the humerus. An anchor member is advanced into the stem such that a lateral projection thereof is disposed through the stem and is embedded in bone adjacent to the stem. A joint interface is secured to the stem and/or the anchor member.

As described above, in certain aspects the stemless humeral component can be modular to provide more options for the surgeon during a revision surgery. For example, the modular humeral component can include a stemless fixation component adapted to be secured in the head of the humerus and a spherical head removably attached to the fixation component. During the revision surgery, the modular approach can make it easier to convert an anatomic shoulder prosthesis to a reverse shoulder prosthesis.

In any of the above-mentioned aspects, the anchor member can include a helical structure advanceable to engage corresponding surfaces of the arms. In certain aspects, the anchor can include a cylindrical sleeve and the helical structure can include at least one thread (e.g., one thread, two threads, three threads, or four threads) projecting laterally therefrom.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

DETAILED DESCRIPTION

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Figure 1A:
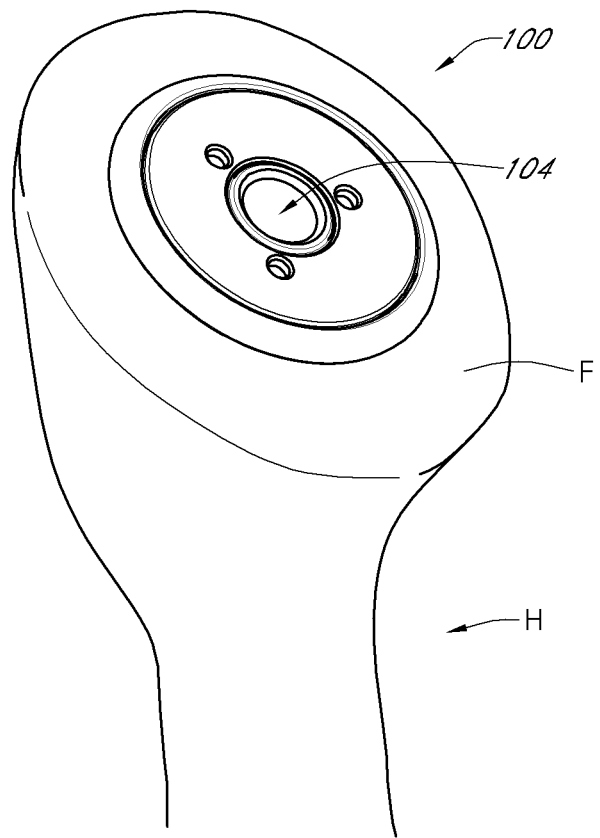
FIG. 1A is a perspective view of one embodiment of a stemless humeral shoulder assembly shown mounted in a humerus.
Figure 1B:
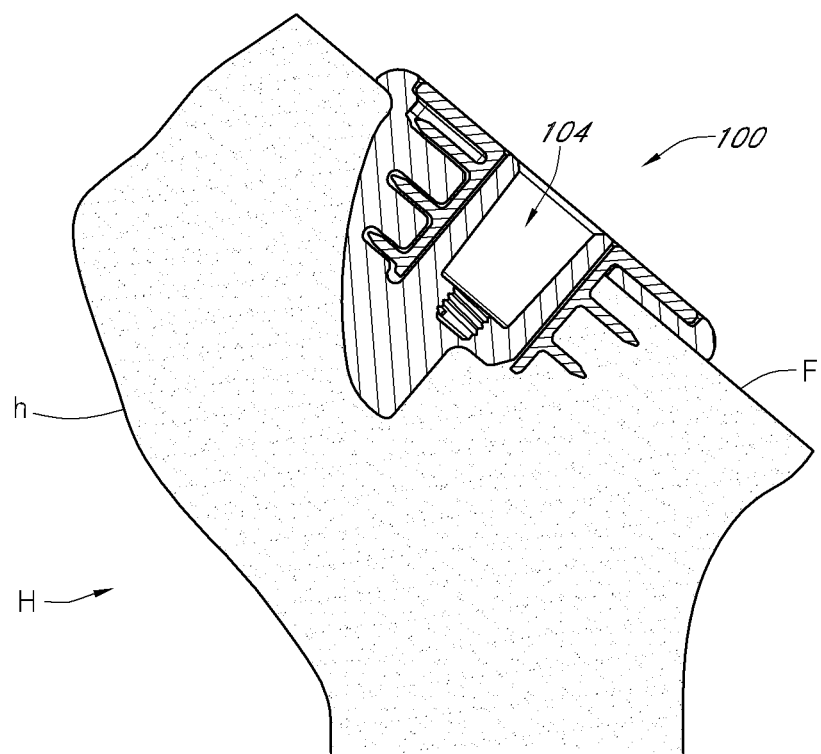
FIG. 1B is a cross-sectional view of FIG. 1A, showing the stemless humeral shoulder assembly disposed in the humeral head.

FIG. 1A shows a humeral shoulder assembly 100 that has been implanted in an exposed face F of a humerus H. The assembly 100 has a recess 104 in which further components of a prosthetic shoulder joint can be secured. The configuration of the assembly including the recess 104 enable the humerus H and a corresponding scapula to be fitted with either an anatomical shoulder or a reverse shoulder configuration either initially or as part of a revision procedure. FIG. 1B shows that in certain applications, the shoulder assembly 100 can be fully retained within a head h of the humerus H. In other words, the distal-most portion of the assembly 100 is disposed in the humeral head h. The assembly 100 does not have members that protrude beyond the head h into the intramedullary canal. This arrangement is less invasive and simplifies the procedure compared to a procedure involving a humeral component with a stem, as discussed elsewhere herein.

Figure 24A:
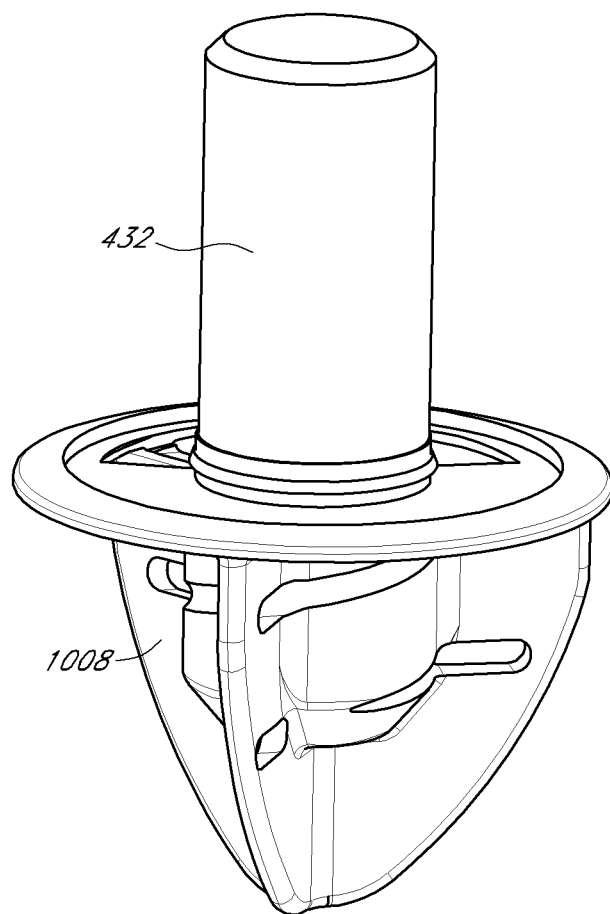
FIGS. 24A-24B illustrate tool and component combinations that can be provided in various methods of implantation of the stemless humeral shoulder assembly of FIG. 17.
Figure 25:
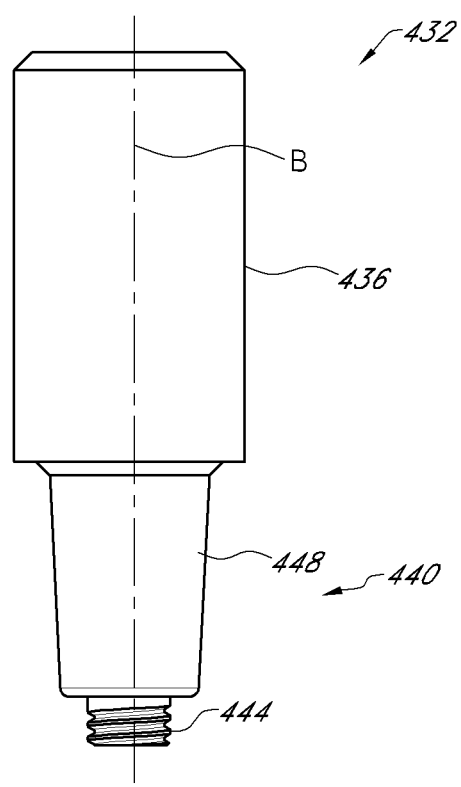
FIG. 25 illustrates an adaptor or centering pin that can be used to align a driver with a base member, as discussed herein.
Figure 26:
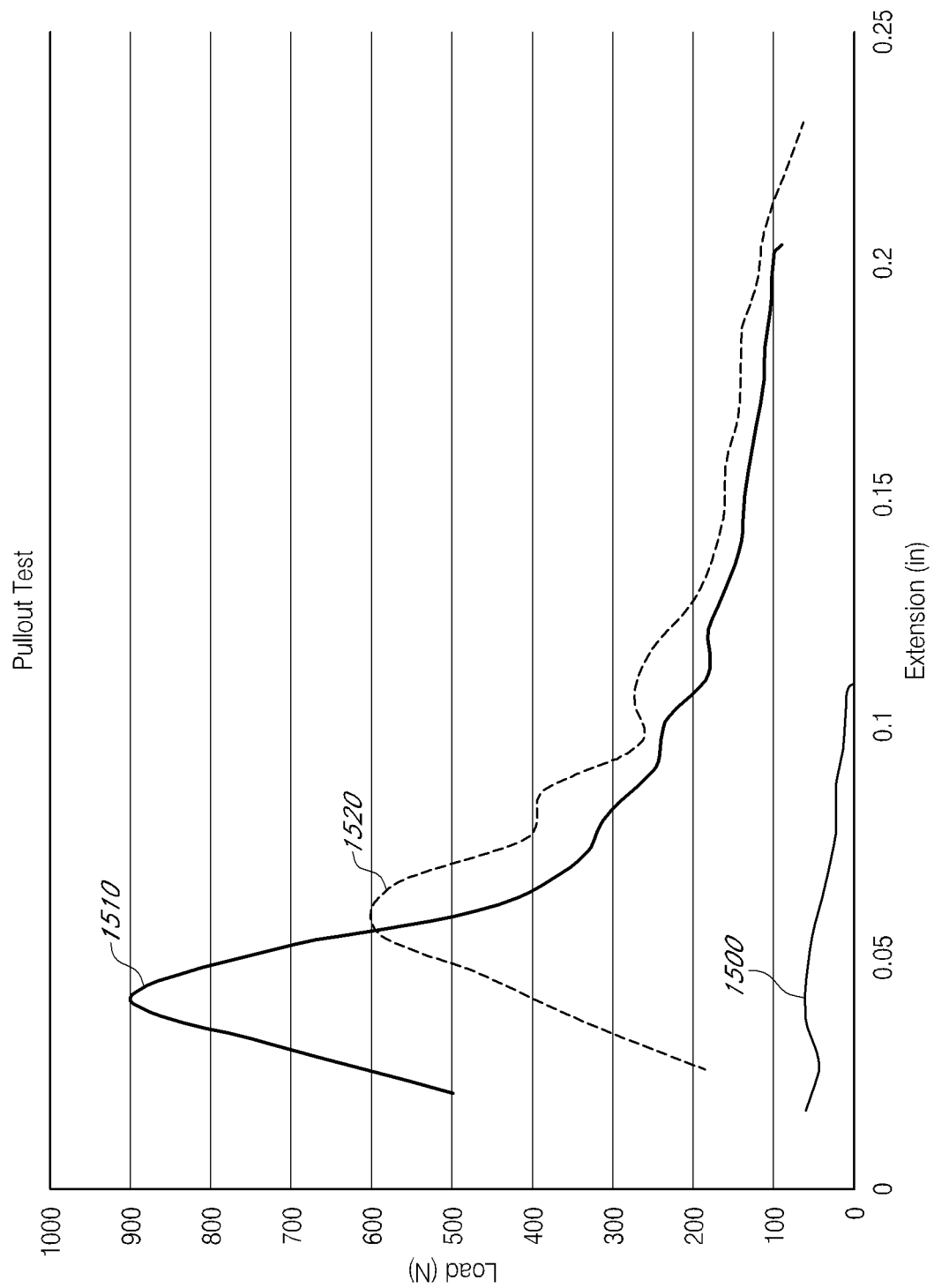
FIG. 26 illustrates the performance of various embodiments of stemless humeral shoulder assemblies.

FIGS. 2-9 elaborate on advantageous structures and variations of the shoulder assembly 100 that can be employed in the stemless approach of FIGS. 1A-1B. Methods of using the shoulder assembly 100 are discussed below in connection with FIGS. 10A-10H. Shoulder assemblies capable of being at least partly delivered over a guide wire are discussed below in connection with FIGS. 11-16C. FIGS. 17-24B illustrate shoulder assemblies where a joint interface mounting platform or recess is disposed on a base member and an anchor member is provided primarily or solely for bone securement function. FIG. 25 shows an adaptor that can be used in connection with several embodiments and methods of applying shoulder assemblies. FIG. 26 illustrates the performance of certain embodiments compared to a prior art design. While incremental differences in these embodiments and methods are discussed below, it is to be understood that features of each embodiment can be combined with features of the other embodiments, as appropriate.

I. Assemblies Having Reinforced Bone Engaging Anchor Members

Figure 2:
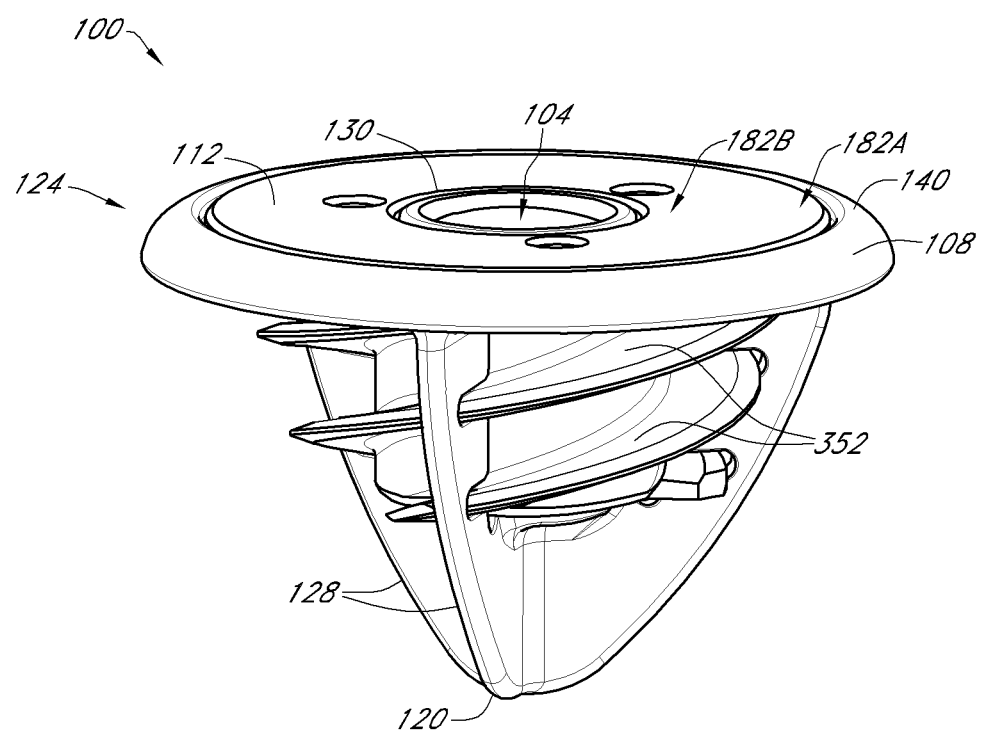
FIG. 2 is a perspective view of the stemless humeral shoulder assembly of FIGS. 1A and 1B.
Figure 3:
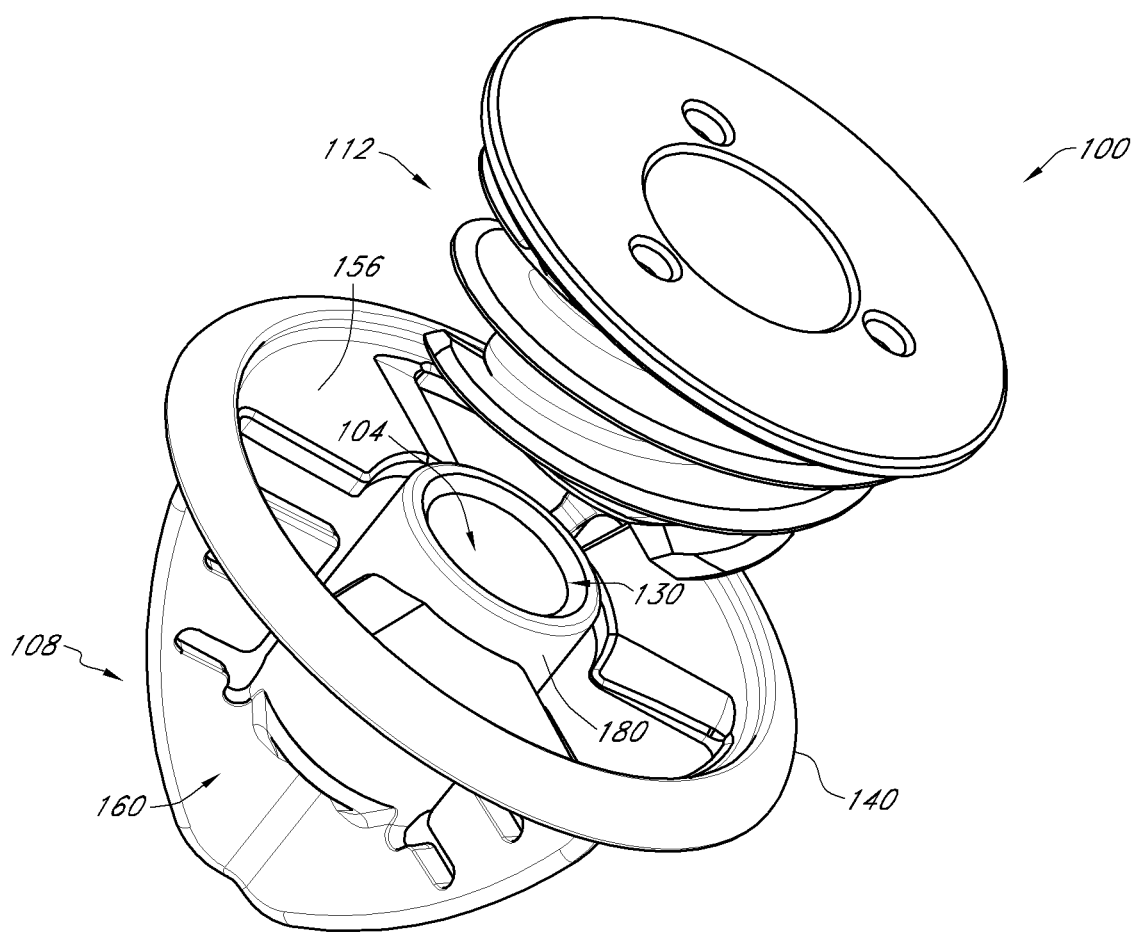
FIG. 3 is an exploded view of the stemless humeral shoulder assembly of FIG. 2.

FIGS. 2 and 3 show more detail of components of the shoulder assembly 100 that among other features and advantages provides an anchor member with an inwardly positioned cylindrical member that reinforces outwardly positioned helical structures as discussed below.

The assembly 100 has a base member 108 and an anchor member 112. FIG. 3 shows that the base member 108 and anchor member 112 are separable components that can be applied to the patient separately, e.g., assembled in multiple steps within the bone as discussed below. The base member 108 has a distal end 120 and a proximal end 124. The distal end 120 is configured to be embedded in the head of a humerus. The proximal end 124 is configured to be disposed adjacent to a face of the humerus or another bone surface. The base member 108 has a plurality of spaced apart arms 128 projecting from the proximal end 124 to the distal end 120. The base member 108 also has a central portion, e.g., a cylindrical member 130, that forms part of the recess 104, as discussed in more detail below. In the illustrated embodiment, the arms 128 are equally spaced about the cylindrical member 130. The arms 128 can be spaced apart by about 120 degrees. The base member 108 and the other base members discussed below can have three arms. The base member 108 and the other base members discussed below can have one or a plurality of arms 128. In various embodiments, the base member 108 and the other base members discussed below can have two, three, four, five, or six arms. The arms 128 preferably are thin in the circumferential direction such that large gaps are provided between the arms.

Figure 4:
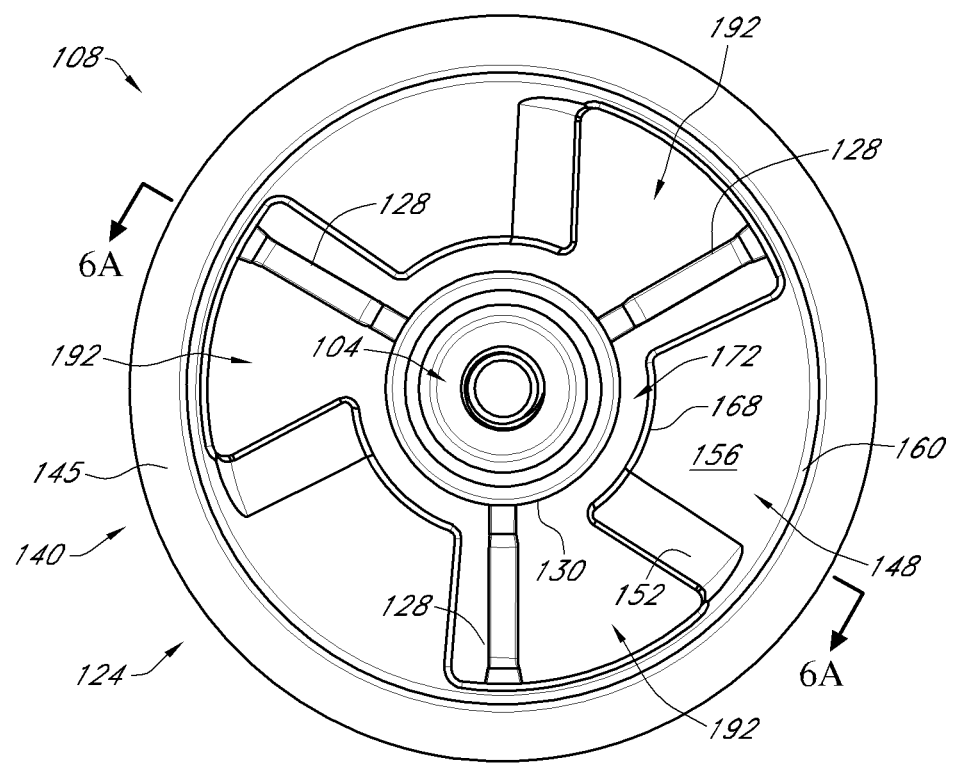
FIG. 4 is a top view of the base member of the shoulder assembly of FIG. 2.

FIGS. 3 and 4 show the proximal end 124 of the base member 108 in more detail. In particular, the proximal end 124 can include a peripheral member 140 disposed about the outer periphery of the proximal end 124. The peripheral member 140 can be coupled with proximal ends 144 of the arms 128 (see FIGS. 5-6A) to provide a unitary structure. In one embodiment, the peripheral member 140 comprises an annular structure 145 that is tapered such that a convex surface 146 is provided between proximal and distal portions of the peripheral member 140. The convex surface 146 extends from a bone engaging side of the peripheral member 140 to a proximal side of the peripheral member 140. The proximal side of the peripheral member 140 is disposed adjacent to but may be spaced from another joint component, such as a portion of an assembly including an anatomical or reverse shoulder joint humeral interface.

In one embodiment, the proximal end 124 can include a plurality of guide members 148 that can be coupled with the peripheral member 140. The guide members 148 can include plate-like projections extending radially inwardly from an arcuate segment of the peripheral member 140. The guide members 148 can be coupled with, attached to or a monolithic extension of an inner edge of the peripheral member 140. In one embodiment, the base member 108 includes three guide members 148. The guide members 148 can include an angled or lead surface 152 that is angled relative to a transverse plane of the proximal end 124. As used in this context, a transverse plane of the proximal end 124 is a plane that extends perpendicular to a longitudinal axis A (see FIGS. 5 and 6A) of the cylindrical member 130. The angle of the lead surface 152 is selected to match the angle of a distal face of a helical structure of the anchor member 112 as discussed further below in connection with FIGS. 6A and 8.

In one embodiment, each of the guide members 148 includes a flat surface 156. Each of the flat surfaces 156 can be disposed on a transverse plane of the proximal end 124. The flat surfaces 156 can extend between an outer portion 160 coupled with the peripheral member 140 and an inner portion 168 disposed adjacent to the cylindrical member 130. In the illustrated embodiment, each inner portion 168 of three guide members 148 is spaced from the cylindrical member 130 by a corresponding gap 172. The gaps 172 partly define an annular volume (projecting distally into the page in FIG. 4) in which a cylindrical portion of the anchor member can be disposed, as discussed further below.

FIG. 3 shows that the flat surface 156 can be disposed at an elevation distal of (or below) the proximal-most aspect of the peripheral member 140. The distance between the proximal-most aspect of the peripheral member 140 and the flat surface 156 can provide a space into which at least a portion of the anchor member 112 can be recessed. In one embodiment, a proximal end 180 of the cylindrical member 130 is disposed at about the same elevation of the proximal-most aspect of the peripheral member 140. In some embodiments, an outside surface of the cylindrical member 130 and an inside surface of the peripheral member 140 define side surfaces of an annular space into which a proximal portion of the anchor member 112 can be received. FIG. 2 shows that the annular space bounded by the outside surface of the cylindrical member 130 and the inside surface of the peripheral member 140 provides a substantially flush, e.g., stepless, profile or transition from the inner and proximal-most aspect of the peripheral member 140 to an outer periphery 182A of the anchor member 112 and from an inner periphery 182B of the anchor member to the proximal end 180 of the cylindrical member 130. The flush profile enables other components of a shoulder joint to be drawn down adjacent to but preferably spaced from the assembly 100.

Figure 6:
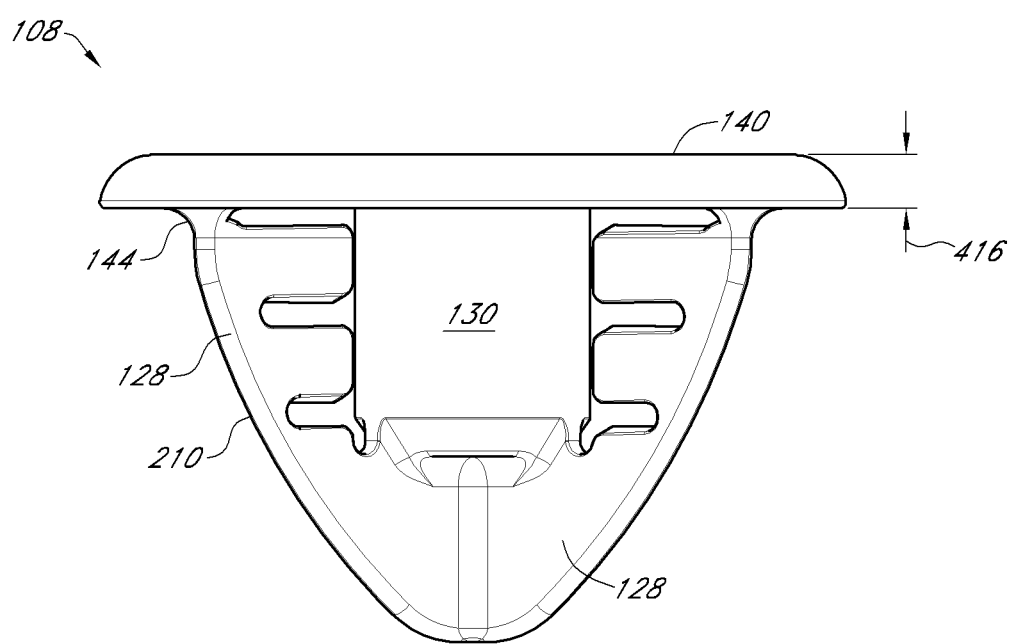
FIG. 6 is a second side view of the base member of FIG. 4.
Figure 6A:
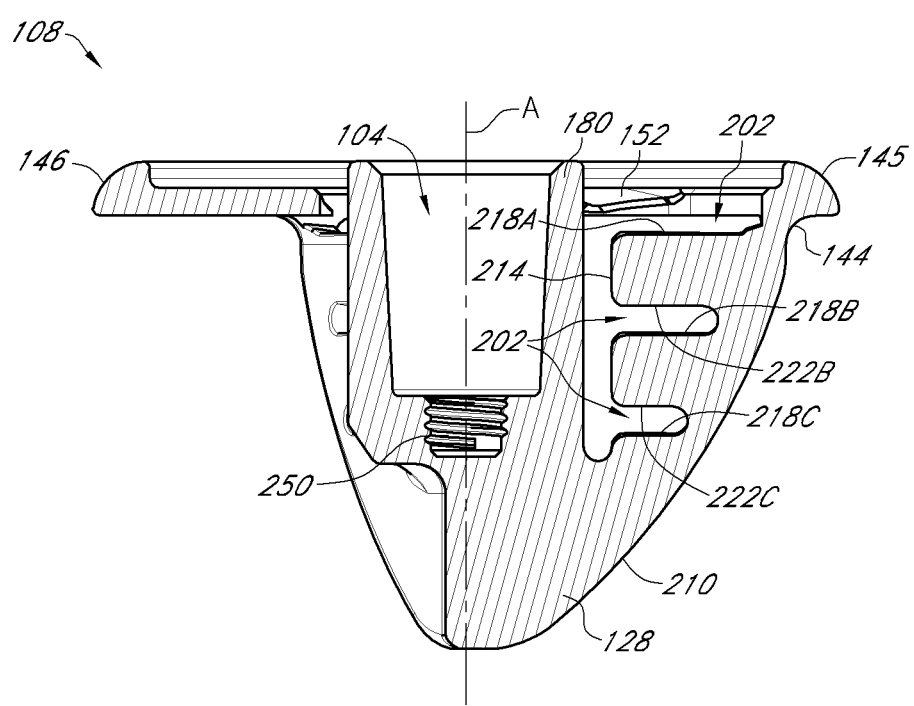
FIG. 6A is a cross-section of the base member shown in FIG. 6 through line 6A-6A in FIG. 4.

FIG. 4 shows that the guide members 148 generally are spaced apart by arcuate openings 192. The openings 192 extend from a lower end of one of the angled surfaces 152 to an end of an adjacent guide member 148. As discussed further below, the openings 192 permit laterally extending portions of the anchor member 112 to be advanced into the base member 108. In certain embodiments, the laterally extending projections include one or more, e.g., three, threads that can be advanced through the openings to engage with the base member 108 at a position distal of the guide members 148. FIG. 4 shows that the arms 128 are disposed distal of but accessible through the openings 192. The arms 128 are located at a circumferential position between the angled surface 152 of a first guide member 148 and a non-angled surface of a second guide member 148, where the second guide member is adjacent to the first guide member. Preferably, the circumferential position of the arms 128 is closer to the circumferential position of the non-angled surface of the second guide member 148 as shown. In this context, the circumferential position is determined by projecting these structures to the plane upon which the non-angled surface 148 is disposed. FIG. 6A shows that a proximal portion of the arms 128 is located distal of the distal-most aspect of the angled surface 152.

FIG. 6A shows one of the arms 128 in more detail. In some embodiments, the arms 128 are each identical. In other embodiments, the arms differ from each other. For example, in the single thread configurations of FIGS. 11 and 17 the arms differ from each other in having slots advanced distally from a first arm to a next arm in the direction of rotation of an anchor member to accommodate the path of the helical member or thread, as discussed below in connection with those embodiments. The arms 128 have a plurality of slots 202, e.g., three slots disposed between proximal and distal ends thereof. FIG. 6A shows that the proximal-most slot 202 can be different from the two slots 202 disposed distal thereof in that the proximal-most slot 202 is bounded by a lower surface 218A discussed below but not by a corresponding upper edge formed in the arm 128. As noted above, the arm 128 is coupled with the peripheral member 140 at a proximal end 144 of the arm 128. In one embodiment, a unitary structure is provided. In such a structure, a continuous structure can be provided from within the peripheral member 140 to within a proximal portion of the arm 128 so that there are no welds or joining lines or boundaries in this area. Such an arrangement simplifies the structure and eliminates potential areas for concentration of stress and potentially failure.

An outer edge 210 of the arms 128 provides a continuously arcuate sloping surface in one embodiment. The sloping surface can facilitate insertion of the base member 108 into an exposed humeral face F as discussed above and further below in connection with FIGS. 10A-10H. An inner edge 214 of the arm 128 can include one or a plurality of, e.g., three, laterally extending faces or surfaces 218A, 218B, 218C.

The angle of the surfaces 152, 218A, 218B, 218C can be configured to facilitate advancement of a lateral extent of the anchor member 112 along a helical path. For example, initial advancement of a lateral portion of the anchor member 112 can cause a leading edge surface of the anchor member 112 to slide along the surface 152 shown in FIG. 6A. Continued advancement can cause the leading edge surface of the anchor member 112 to approach and then slide across the surface 218A shown in FIG. 6A. Continued advancement can cause the leading edge surface of the anchor member 112 to approach and then slide across a surface 218B of an arm 128 disposed adjacent to and on a first side of the arm 128 shown in FIG. 6A. Continued advancement can cause the leading edge surface of the anchor member 112 to approach and then slide across a surface 218C of an arm 128 disposed adjacent to and on a second side of the arm 128 shown in FIG. 6A. Once the anchor member 112 slides across the surface 218C of each arm 128, the anchor member 112 can continue to rotate an additional 5-15 degrees to further compress the entire construct into the bones. Advancement is complete when a proximal face of the threads 340 (see FIG. 8) contacts an upper surface 222B, 222C of the slots 202 (see FIG. 6A).

At least some of the surfaces 218A, 218B, 218C can be disposed in laterally projecting recesses or channels of the arms 128. For example, the surface 218B extends laterally outwardly from the inner edge 214 of the arms 128. A corresponding surface 222B can extend outwardly from the inner edge 214 adjacent to the surface 218B. The surfaces 218B, 222B can be substantially parallel along their length. The surfaces 218B, 222B can be spaced apart by a short distal-proximal distance. The short distal-proximal distance can be about the same as the thickness of lateral protrusions (e.g., threads) of the anchor member 112 discussed below. In these embodiments both of the surfaces 218B, 222B play a role in guiding the advancement of the anchor member 112. The face 222B can have an angled surface similar to that of the surface 218B. For example, the angle of the face 222B can be the same angle as that of the face 218B.

In one embodiment, each of the faces 218A, 218B, 218C has a length as measured radially away from the axis A that differs from the length of the other faces. The distal-most face 218C can have the shortest length. The proximal-most face 218A can have the longest length. A face 218B disposed between the distal- and proximal-most faces 218C, 218A can have an intermediate length. These lengths can correspond to the tapered profile of the base member 108, e.g., with the arms 128 having a generally convex shape from proximal to distal as viewed from the side. The lengths of the faces 218A, 218B, 218C can correspond to the profile of the lateral projection of the anchor member 112, which is some embodiments may be tapered.

In one embodiment, the proximal-most face 218A does not have a corresponding face on the arm 128 disposed proximal thereof. A lower surface of the guide member 148 disposed adjacent to but clockwise of the arm 128 can abut a proximal side of a thread while a distal side of the thread advances along the face 218A. In this sense, each of the faces 218A, 218B, 218C has a corresponding surface that together guide a thread of the anchor member 112 as discussed further below.

In the embodiment of FIGS. 1-10H, each arm has a plurality of, e.g., three faces 218A, 218B, 218C. The face 218A of each of the arms 128 is disposed at the same elevation as the corresponding face 218A of adjacent arms 128. The face 218B of each of the arms 128 is disposed at the same elevation as the corresponding face 218B of adjacent arms 128. The face 218C of each of the arms 128 is disposed at the same elevation as the corresponding face 218C of adjacent arms 128. This construction defines a plurality of helical paths on the base 108 for guiding helical members, as appropriate for certain embodiments. Other embodiments have different helical paths, such as a single path as discussed below in connection with the embodiments of FIGS. 11 and 17. Rather, a plurality of spaced-apart surfaces reside on and/or define the helical path. In one right-hand configuration, a first helical path is defined by a face 218A of a first arm 128, a face 218B of a second arm 128 adjacent to but disposed clockwise of (as defined above) the first arm, and a face 218C of a third arm 128 adjacent to but disposed counter-clockwise of (as defined above) the first arm. In one embodiment, the first helical path also includes the lead surface 152 disposed above and circumferentially between the first and third arms 128. A second helical path can extend from a surface 152 to the second arm 128 to a face 218C of the first arm 128. A third helical path can extend from a surface 152 of the third arm 128 to a face 218C of the second arm 128. Each of the surfaces on the helical paths can have substantially the same angle relative to a transverse plane of the base 108. In some embodiments, the angle of the faces 218A, 218B, 218C can be different.

In other embodiments of the base member 108, three left-handed helical paths can be provided, each one commencing with an oppositely oriented surface similar to the surfaces 152 and traversing counter-clockwise to a face 218A below and on the arm 128 immediately counter-clockwise of the oppositely oriented surface, then to the face 218B on the next arm 128 and then to the face 218C on the next arm 128. In this context, the "next arm 128" is the arm circumferentially spaced from and immediately counter-clockwise of the arm from which the path extends.

Unlike a conventional mating screw structure, only very small segments of the helical path involve contact between the faces 218A, 218B, 218C and a mating structure. This arrangement enhances the surface area of the anchor thread contacting bone when the assembly 100 is disposed in the bone.

Figure 5:
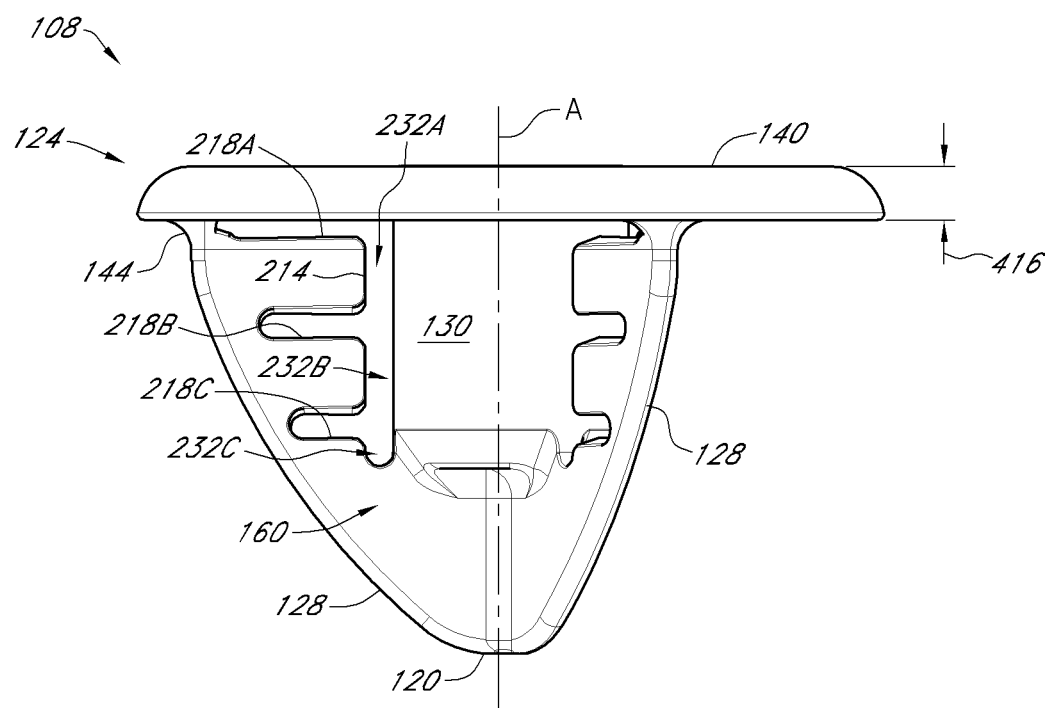
FIG. 5 is a first side view the base member of FIG. 4.

FIG. 5 shows that a gap 232A is provided between the inner edge 214 and the cylindrical member 130 below the face 218A. A gap 232B is provided between the inner edge 214 and the cylindrical member 130 below the face 218B. A gap 232C is provided between the inner edge 214 and the cylindrical member 130 below the face 218C. The gap 232C is substantially the same width as the gaps 232A, 232B. In one embodiment, the gaps 232A, 232B, 232C are substantially the same as the gap 172. The gaps 172, 232A, 232B, 232C define part of a cylindrical space configured to receive part of the anchor member 112 as discussed further below. The gap 232C enables a distal portion of the anchor member 112 to be advanced distal of the face 218C.

FIG. 6A shows that in some embodiments, the cylindrical member 130 has a threaded recess 250 formed in a lower portion thereof. The threaded recess 250 enables a component to be advanced into engagement with the base member 108. The component can be another component of a prosthetic joint or can be a tool used in placement of one or more components of the shoulder assembly 100. The recess 250 can engage a guide tool 432 (see FIG. 25) in one technique, discussed in more detail in connection with FIG. 10F.

FIGS. 2 and 7-9 illustrate features of the anchor member 112 which, as discussed above, is advanceable into the base member 108 to a position disposed within the arms 128. The anchor member 112 includes a proximal face 300, a helical structure 304 disposed distally of the proximal face 300, and a cylindrical sleeve 308 configured to be disposed around the recess 104. In some embodiments, the sleeve 308 is configured to be advanced over and receive the cylindrical member 130 as discussed further below.

The proximal face 300 comprises the proximal side of a disc structure 312 disposed at the proximal end of the anchor member 112. The disc structure 312 is configured to be disposed in a space partly bounded by the flat surfaces 156, the inner face of the peripheral member 140, and the outer face at the proximal end 180 of the cylinder member 130 of the base member 108 (see FIG. 3). The disc structure 312 can have a thickness (proximal-to-distal distance) substantially the same as the distance from the flat surfaces 156 to the proximal most aspect of the peripheral member 140. The anchor member 112 is configured such that regions 320 (FIG. 9) of the distal surface of the disc structure 312 are advanced into a position to abut the flat surfaces 156 of the base member 108 when the shoulder assembly 100 is assembled.

Figure 8:
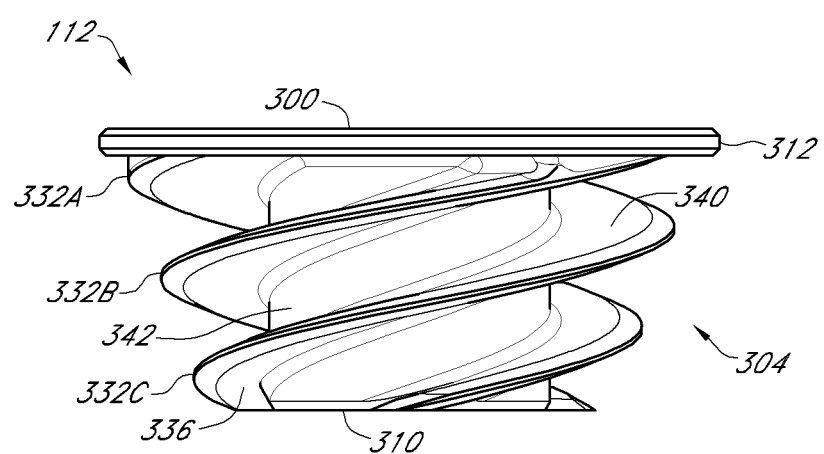
FIG. 8 is a side view of the anchor member of FIG. 7.
Figure 9:
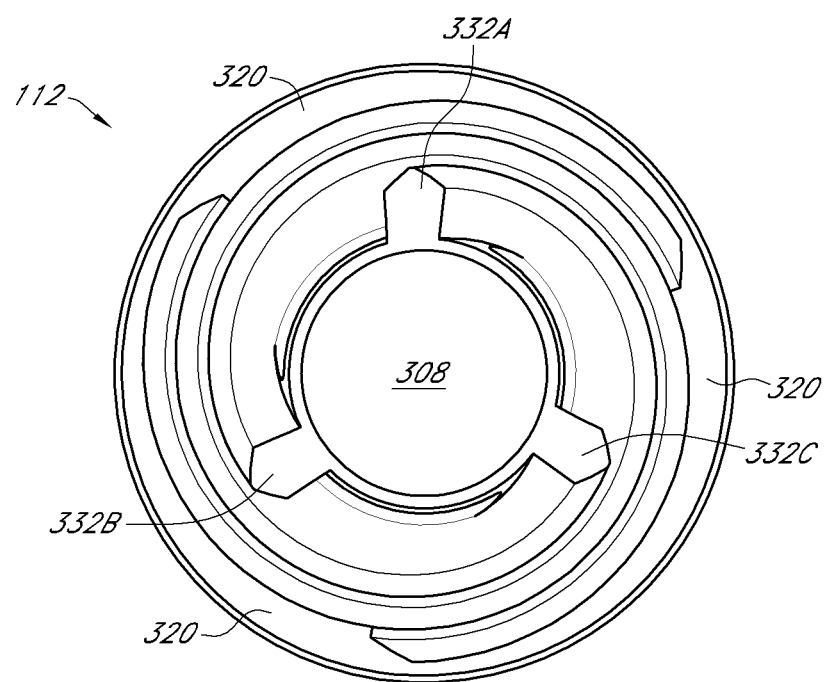
FIG. 9 is a bottom view of the anchor member of FIG. 7.

FIGS. 8 and 9 show the helical structure 304 in more detail. In one embodiment, the helical structure 304 includes three spaced apart helical protrusions 332A, 332B, 332C. In this embodiment, the anchor member 112 has a triple lead configuration. Other embodiments can have a single lead (as in the embodiments discussed in connection with FIGS. 11 and 17 below), a double lead, or a quadruple lead configuration. Distal ends of the three helical protrusions 332A, 332B, 332C can be seen in FIG. 9. Each of these helical protrusions 332A, 332B, 332C has progressively larger diameter from a distal end to a proximal end thereof in the illustrated embodiment. The larger size toward the proximal end enables the helical protrusions to project farther laterally into the faces 218A, 218B, 218C of the arms 128. The smaller size toward the distal end enables the disruption of bone toward the distal end to be minimized. The helical protrusions can be threads in some embodiment.

FIG. 8 shows distal and proximal faces 336, 340 of one of the helical protrusions. The distal face 336 is configured to be advanced along one or guided by one of the helical paths described above. The distal face 336 is angled relative to a transverse (e.g., perpendicular) cross-sectional plane of the anchor member 112, which angle may be selected to match the lead surface 152, as discussed above. For example, the distal face 336 can slide along the lead surface 152, one of the faces 218A, one of the faces 218B, and one of the faces 218C. The proximal face 340 can slide along or be guided by the surface 228B (FIG. 6A) or another distally-oriented face disposed in one of the arms 128 or on a lower surface of the guide member 148.

FIG. 8 shows that a spiral or helical surface 342 extends between adjacent helical protrusions 332A, 332B, 332C. The spiral surface 342 can extend from the base of a distal surface 336 of the helical protrusion 332B to the base of the proximal surface of the helical protrusion 332C. The spiral surface 342 has a proximal to distal dimension that is about the same as the proximal-distal dimension of the side surface 214 between the surfaces 218A, 228B (See FIG. 6A). The proximal to distal dimension of the spiral surface 342 is about 50% larger than and in some cases twice as large as the proximal to distal dimension of the helical protrusions 332A, 332B, 332C.

FIG. 2 shows that the anchor member 112 projects into the arms 128 and into a space between the arms when the anchor member and the base member are assembled. The anchor member 112 is exposed between the arms 128 when advanced into the base member 108. More specifically, a plurality of elongate segments 352 of the helical protrusions 332A, 332B, 332C are not covered by the faces 218A, 218B, 218C, 222B of the arms 128 but rather are located in an open area between the arms. The exposed segments 352 create areas of engagement with the bone that vastly increase the initial pull-out force of the assembly 100 when initially placed. This improved initial pullout force greatly reduces the chance of dislodgement, as discussed below in connection with FIG. 26.

Some additional unique features of the assembly 100 include helical surfaces in the anchor member 112 that mate only in very small and spaced apart areas of the base member 108 while exposing a majority of the helical surface to allow the exposed areas to be disposed directly in the bone for direct contact therewith. In some embodiments, a portion of the helical surface is disposed within the arms 128 and not exposed but a majority of the helical surface is exposed to be embedded in bone. The percentage of the surface area of the exposed segments 352 to the total area of the helical protrusions 332A, 332B, 332C is between about 80 and 98% in some embodiments. The percentage of the area of the exposed segments 352 to the total area of the helical protrusions 332A, 332B, 332C is between about 85 and 95% in some embodiments. The percentage of the area of the exposed segments 352 to the total area of the helical protrusions 332A, 332B, 332C is about 91% in some embodiments. Similarly, the ratio of the length of the exposed segments 352 to the total length of the helical protrusions 332A, 332B, 332C is between about 0.8 and about 0.98, e.g., between about 0.85 and about 0.95, e.g., about 0.9 in various embodiments. It may be desirable to further enhance engagement of the assembly 100 and other assemblies herein by increasing the ratios and percentages discussed in this section. Higher percentages and ratios can be provided by decreasing the distance between threads such that each thread has more turns. The percentage and ratios discussed in this passage are also applicable to the other embodiments discussed below.

Also, the structure provided herein enables the threads to extend a large distance from the center of the recess 104. For example, the lateral extent, e.g., radius of the helical protrusions 332A, 332B, 332C can be at least 50% of the lateral extent, e.g., radius of the peripheral member 140, for example, at least about 50% and/or less than or equal to about 75%. In some embodiments, the lateral extent of at least one of the helical protrusions 332A, 332B, 332C can be at least about 50%, such as between about 50% and about 55%, of the diameter of the peripheral member 140. In some embodiments, the lateral extent of at least one of the helical protrusions 332A, 332B, 333C can be at least about 60%, such as between about 60% and about 65%, of the diameter of the peripheral member 140. In some embodiments, the lateral extent of the helical protrusions 332A, 332B, 333C can be at least about 70%, such as between about 70% and about 75%, of the diameter of the peripheral member 140. In certain embodiments, as shown in FIG. 8, the diameter of each of the helical protrusions 332A, 332B, 332C can vary from the proximal face 300 to the distal end 310 of the anchor 112. For example, the diameter of a portion of the helical protrusions 332A, 332B, 332C near the proximal face 300 can be greater than the diameter of a portion of the helical protrusions 332A, 332B, 332C near the distal end 310. The percentage can be measured against any portion of the protrusions 332A, 332B, 332C. In some embodiments, the lateral extent of the helical protrusion 332C can be between about 50% and 55% of the diameter of the peripheral member 140, while the lateral extent of the helical protrusion 332A can be between about 70% and 75% of the diameter of the peripheral member 140.

Figure 7:
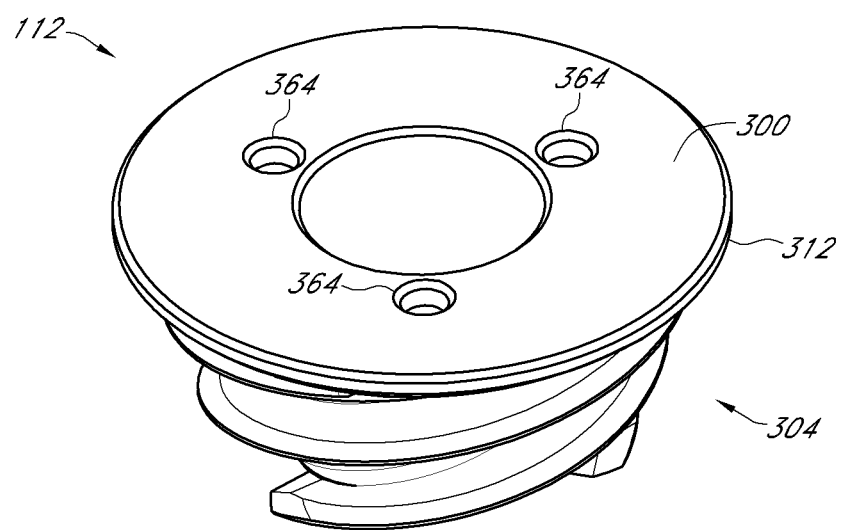
FIG. 7 is a top perspective view of an anchor member of the shoulder assembly of FIG. 2.

FIG. 7 shows that the proximal face 300 of the anchor member 112 can include a driver interface 364 to facilitate advancing the anchor member 112 into the base member 108. The driver interface 364 can take any suitable form, for example, as three spaced apart recesses. The recesses can be cylindrical recesses extending into the disc member 312.

Figure 10A:
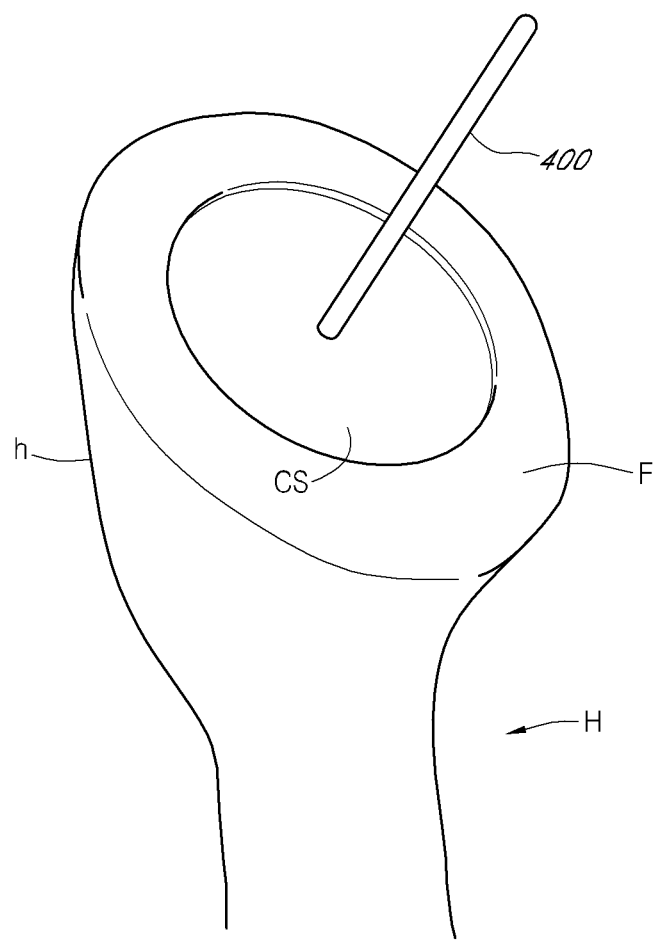
FIGS. 10A-10H illustrate steps of various methods of implantation of the stemless humeral shoulder assembly of FIG. 2.
Figure 10B:
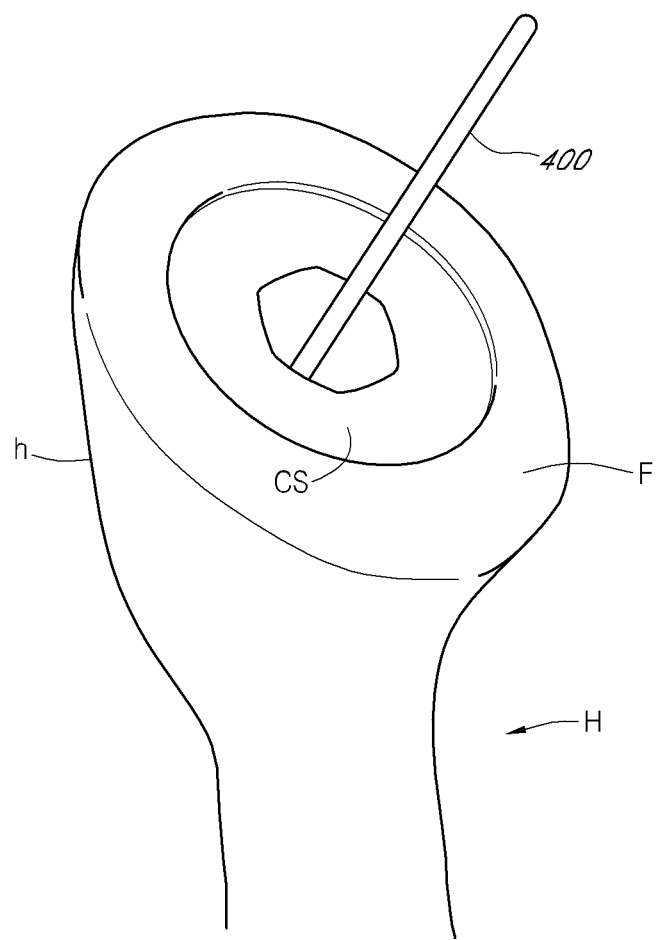
Figure 10C:
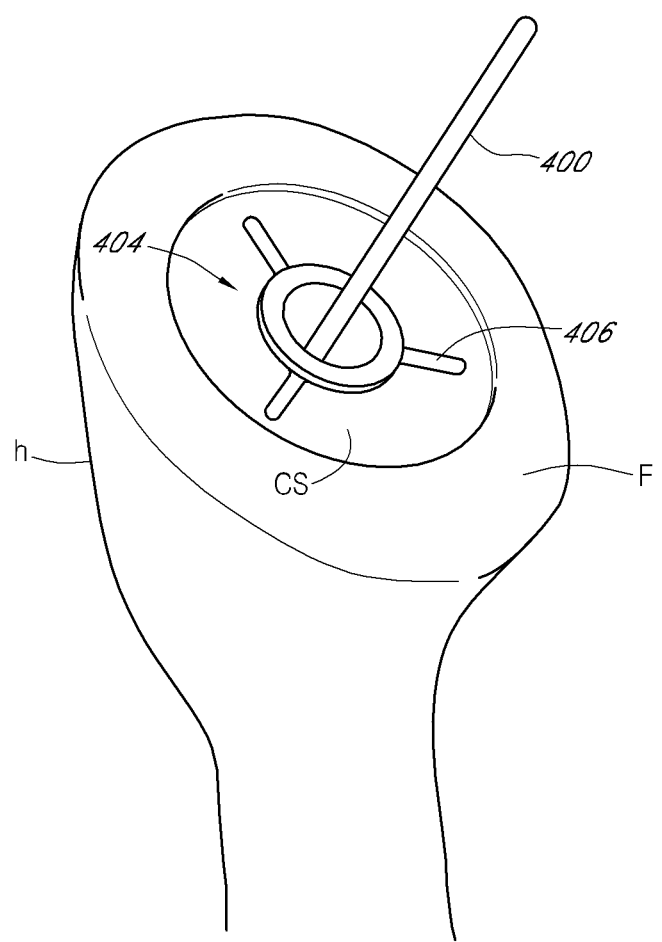
Figure 10D:
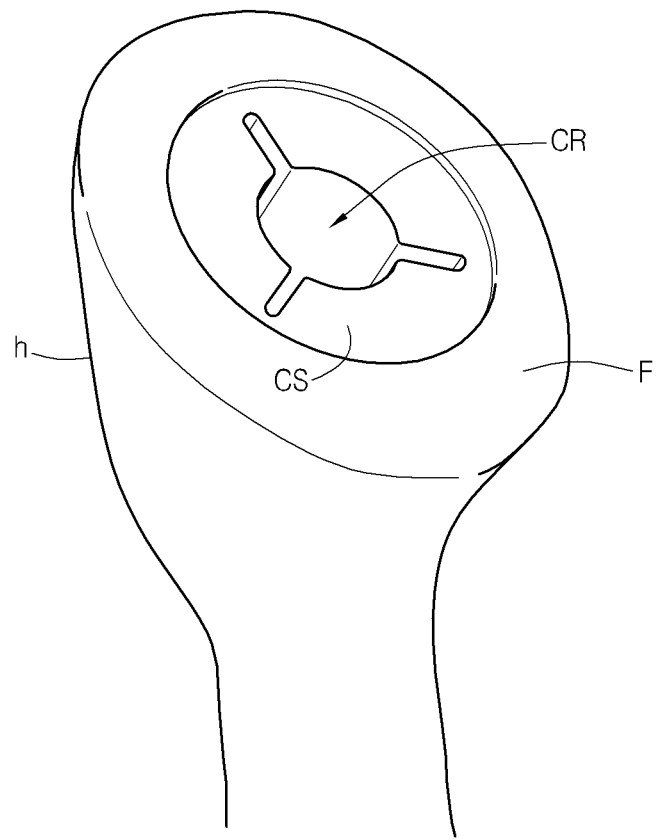

FIGS. 10A-10H illustrate methods of implanting the humeral shoulder assembly 100 into the humerus H. Prior to the step illustrated by FIG. 10A, surgical access has been provided to the humerus H and the humerus has been prepared. Preparing the humerus H can include cutting off a joint-facing portion of the humeral head h. The joint facing portion can be further prepared, for example by providing a countersunk region CS in the exposed face F. The countersunk region CS enhances a low profile application of the assembly 100 as discussed further below. A pin 400 is placed in a central region of the countersunk region CS. FIG. 10B shows that the pin 400 may be used to guide a reamer to create a well at the base of the pin. FIG. 10C shows the well having received a tool 404 that has been advanced into the face F to modify the well to receive the base member 108. For example, the tool 404 has a plurality of, e.g., three, radial projections 406 to create channels radiating from the well as shown in FIG. 10D. Preferably the projections 406 have an edge profile similar to that of the arms 128, e.g., with a convex edge from proximal to distal when viewed from the side similar to the edge 210.

Figure 10E:
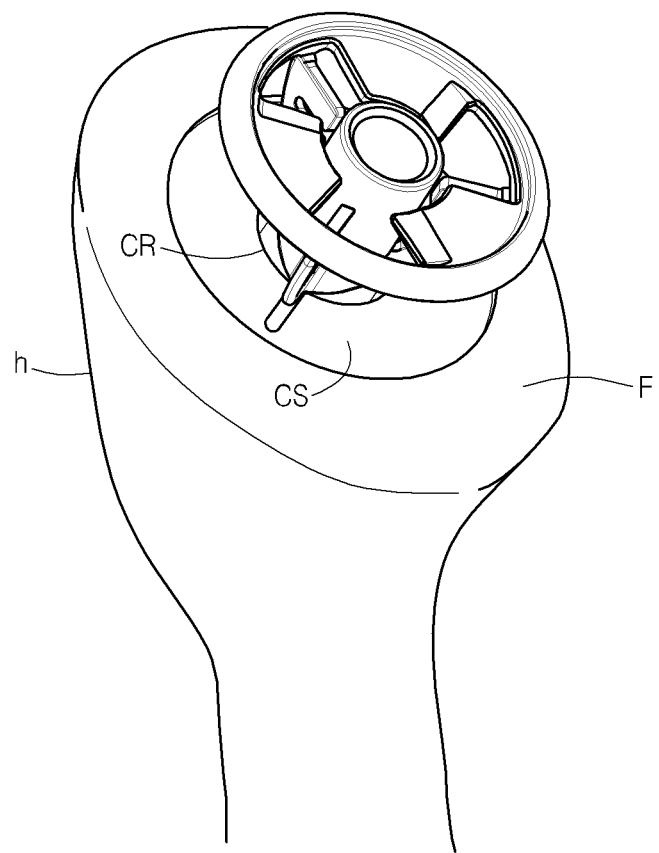

FIG. 10D show the expose humeral face F with the pin 400 and tool 404 removed so that a created recess CR in the face F is shown. The recess CR is configured to permit the base 108 to be advanced with ease into the face F of the humeral head h as shown in FIG. 10E. More specifically, the recess CR is shaped to match the shape of a portion of the base member 108 that projects distally. For example, FIG. 4 shows that the arms 128 can be equally spaced about the base member 108, e.g., outer ends thereof coupled with the peripheral member 140 can be spaced circumferentially by about 120 degrees. The arms 128 can be thin at radially outer portions thereof and can be joined adjacent to the distal end 120 of the base member 108. Accordingly, the radial projections of the recess CR created by the radial projections 406 of the tool 404 can be narrow and spaced apart by the same amount as the arms 128, e.g., about 120 degrees apart.

Although the projection 406 and corresponding projections of the recess CR are generally straight, radial projections, the projections 406 could be curved and/or can extend away from a central region to in a non-radial direction matching the shape and orientation of any projections of the base member 108.

Preferably, the insertion of the base member 108 into the recess CR can be achieved with ease, e.g., without an impactor or any other tools, but rather by hand force. The base member 108 advantageously is symmetrical about the axis A (see FIGS. 4 and 5). This allows the surgeon to insert the base member 108 in any orientation provided that the arms 128 and the projections in the recess CR are aligned. Other configurations have a preferred orientation, as discussed further below.

Figure 10F:
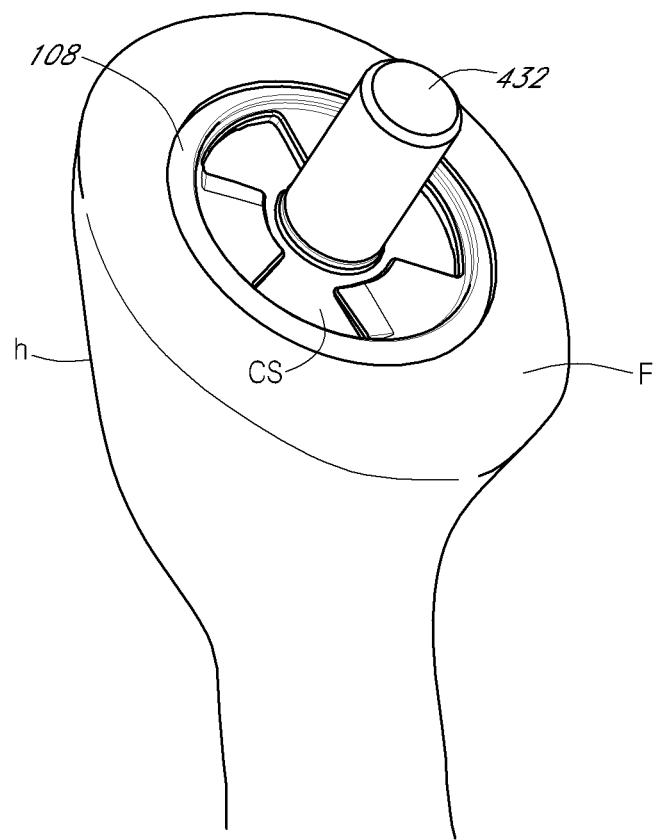

FIGS. 10E-10F show that the countersunk region CS is configured to receive the peripheral member 140 in a recessed position. For example, the countersunk region CS has a bone recessed area, which is recessed by about the proximal-distal dimension 416 (shown in FIG. 6) of the peripheral member 140. By recessing the base member 108, the base member and/or the humeral shoulder assembly 100 can positioned as desired relative to the face F of the humeral head h, e.g., with a small gap or flush mounted. Flush-mount enables a joint interface coupled with the assembly 100 to be positioned close to the face F, e.g., with little to no gap therein. Consistent and accurate positioning of the assembly 100 and joint interface can be important factors in properly locating the prosthetic joint interface.

FIG. 10F shows that after the base member 108 has been inserted into the face F of the humerus a subsequent step can involve coupling the guide tool 432 with the base member. FIG. 25 shows details of one embodiment of the guide tool 432. The guide tool 432 preferably includes a guide body 436 disposed at a proximal portion thereof. The guide body 436 projects outside and proximally of the base member 108 and is configured to guide the anchor member 112 to be advanced thereover. In one form, the guide body 436 is a cylindrical member. A distal portion 440 of the guide tool 432 is configured to be coupled with the base member 108. In particular, a threaded distal portion 444 is configured to mate with the threads in the threaded recess 250 (see FIG. 6A). A tapered portion 448 facilitates insertion of the guide tool 432 into the cylindrical member 130 of the base member 108. More particularly as shown in FIG. 6A, the cylindrical member 130 can be tapered on an inside surface thereof, such that the recess formed in the member 130 is narrower at the distal end than at the proximal end thereof. Stated another way, a wall surrounding the recess in the cylindrical member 130 is closer to the axis A near the threads 250 than near the proximal end of the recess. Similarly, the outside surface of the tapered portion 448 is closer to a central longitudinal axis B of the guide tool 432 than is a proximal portion of the tapered portion 448. The tapers match such that if the guide tool 432 is inserted into the cylindrical member 130 with the axis A, B offset, the surface 448 and the inside surface of the recess in the cylindrical member 130 match to align these axes before the threads 444 and the threads in the recess 250.

Figure 10G:
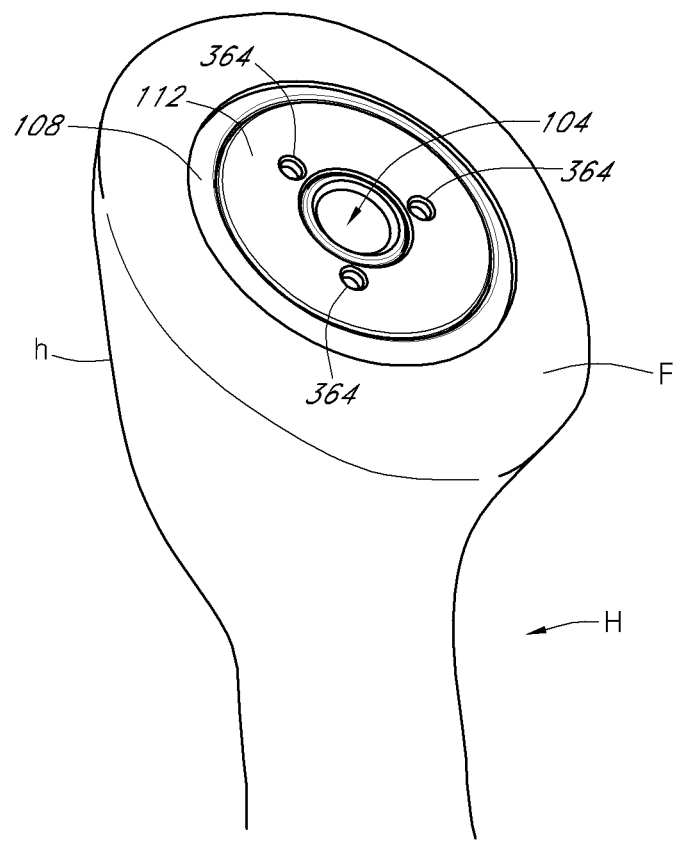

FIG. 10G shows the anchor member 112 engaged with the base member 108. This configuration results from advancement of the anchor member 112 over the guide tool 432 in one method. In one embodiment, a method step includes coupling a driver with the driver interface 364 on the proximal face 300 of the anchor member 112. The driver can take any suitable form, e.g., can include a plurality of protrusions configured to mate with recesses of the driver interface 364. The driver can be configured to snap into or onto the anchor member 112 at the driver interface 364. Embodiments of a driver are discussed below in connection with FIGS. 16B and 24B. Preferably, the driver has a ratchet mechanism such that the surgeon can continuously hold the tool and need not release the handle to re-grip it to apply additional turns to the anchor member 112. However, one advantage of the three thread design of the anchor member 112 is that less rotation of the anchor member is required as compared to a two thread design or a one thread design to fully seat the anchor member in the base member 108.

In one method, the surgeon observes the face F of the humerus and advances the anchor member 112 until some fluid is observed to emerge from the recess CR and/or around the assembly 100. The emergence of fluid suggests that the anchor member 112 is fully seated in the bone in a way providing excellent initial bone retention. Such retention provides enhanced pull-out force.

FIG. 26 illustrates the initial pull-out force 1510 for Embodiment A, a variant of the shoulder assembly 100 in which the anchor member 112 has a single continuous thread. Portions of the helical structure 304 project into the open area defined between the arms 128 and engage the bone thereby increasing the initial pull-out force of the assembly 100 when initially placed. As shown in FIG. 26, the peak force corresponding to the initial pull out force 1510 of Embodiment A is at least ten times greater than the peak force corresponding to the initial pull out force 1500 of the prior art design having a base member and no anchor thread.

Figure 10H:
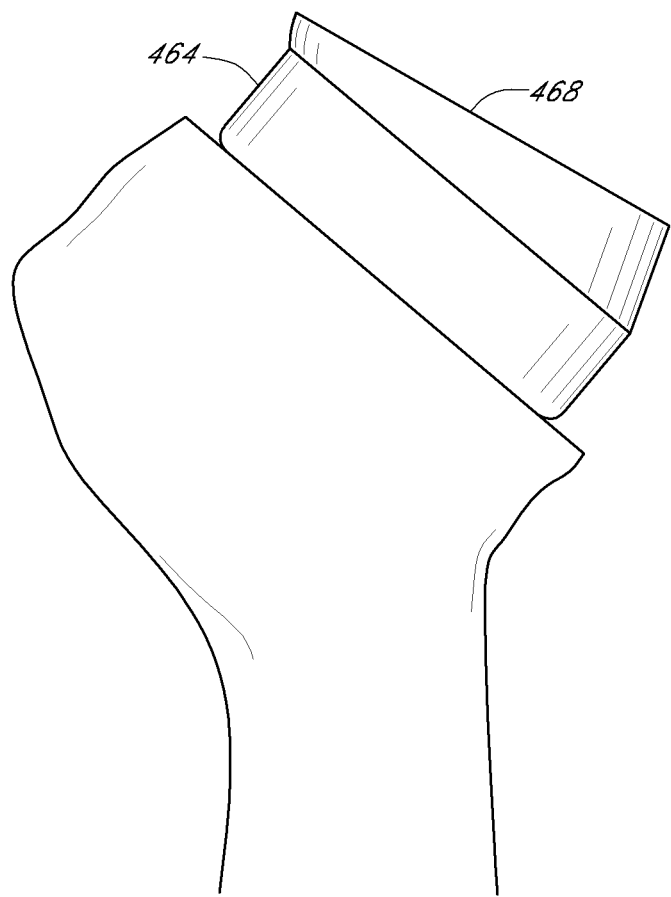
Figure 11:
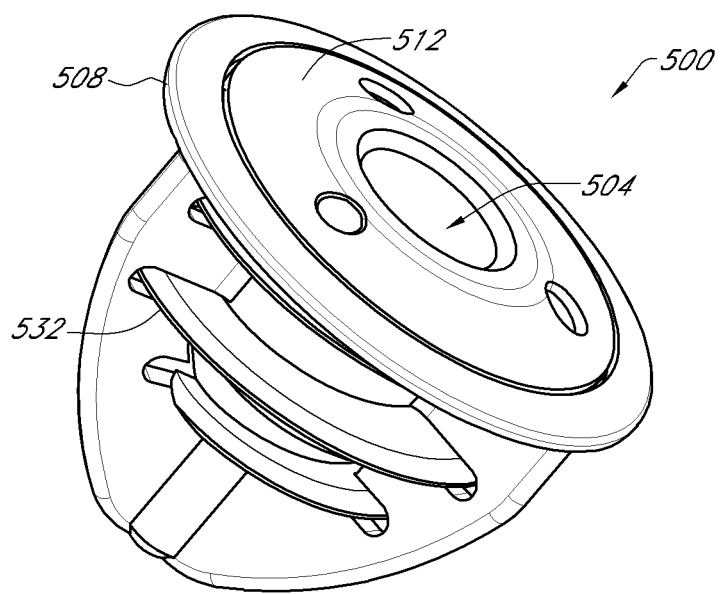
FIG. 11 is a top perspective view of another embodiment of a stemless humeral shoulder assembly.

As discussed above, the assembly 100 enables a variety of joint interface components. The surgeon can couple an anatomical joint interface with the assembly 100, e.g., by positioning an anchor portion of the anatomical joint interface in the recess 104. In some cases, a reverse shoulder configuration is better for the patient. The surgeon can dispose an anchor portion of a reverse configuration shoulder joint interface in the recess 104. FIG. 10H shows an adaptor 464 coupled with the recess 104. The adaptor 464 can be seated with a concave socket portion 468 that can be coupled with a convex head implanted in the scapula in the reverse shoulder configuration.

The methods described above, e.g., in connection with FIGS. 10A-10H, can include additional steps and employ additional tools as discussed below. The shoulder assembly 100 also can be adapted to be compatible with other methods herein, e.g., having a guidewire passage suitable for employing over-the-wire methods discussed below.

The assembly 100 and the methods described above can be modified by incorporation of structures and methods discussed in connection with the embodiments below.

II. Assemblies Having Guidewire Delivery Capability

FIG. 11-16C show a stemless shoulder assembly 500 and methods similar to the shoulder assembly 100 and methods discussed above except as described differently below. The assembly 500 is configured to allow a guidewire to be used to advance components thereof into a prepared humeral face F, providing for an efficient and accurate procedure. The assembly 500 includes a recess 504, a base member 508, and an anchor member 512. As discussed more below, a thread or other helical protrusion 532 extends from the anchor member 512 into engagement with the base member 508 and into an open area where it can engage bone. In this embodiment, the anchor member 512 has a single lead configuration. Other embodiments can have a multiple lead configuration, e.g., including a double lead, a triple lead, or a quadruple lead configuration.

Figure 12:
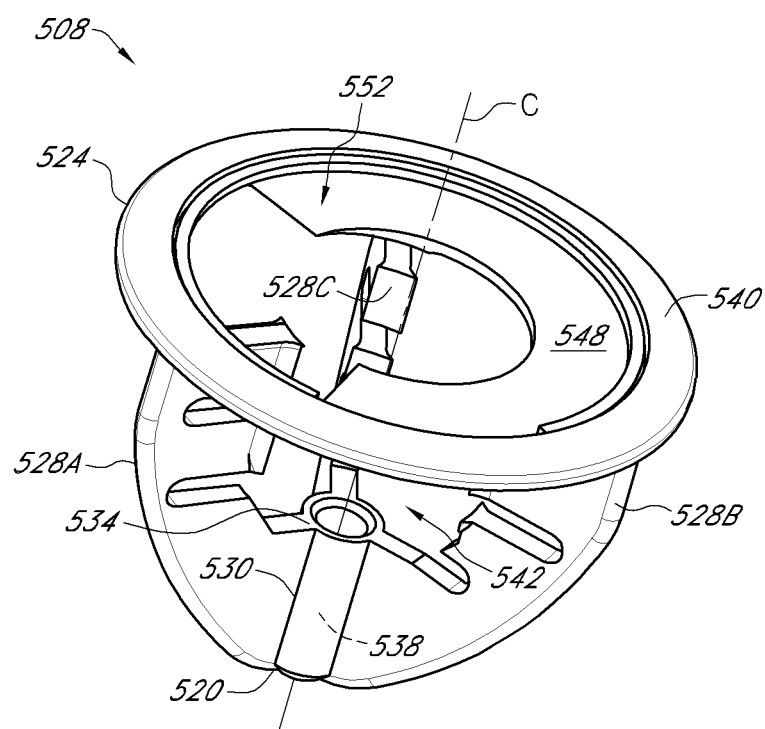
FIG. 12 is a top perspective view of a base member of the stemless humeral shoulder assembly of FIG. 11.
Figure 13:
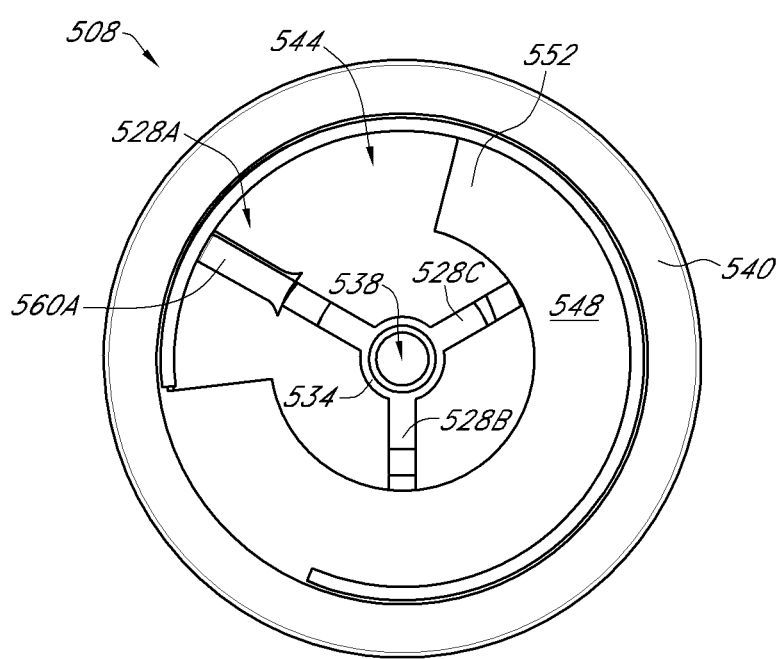
FIG. 13 is a top view of the base member of FIG. 12.
Figure 13A:
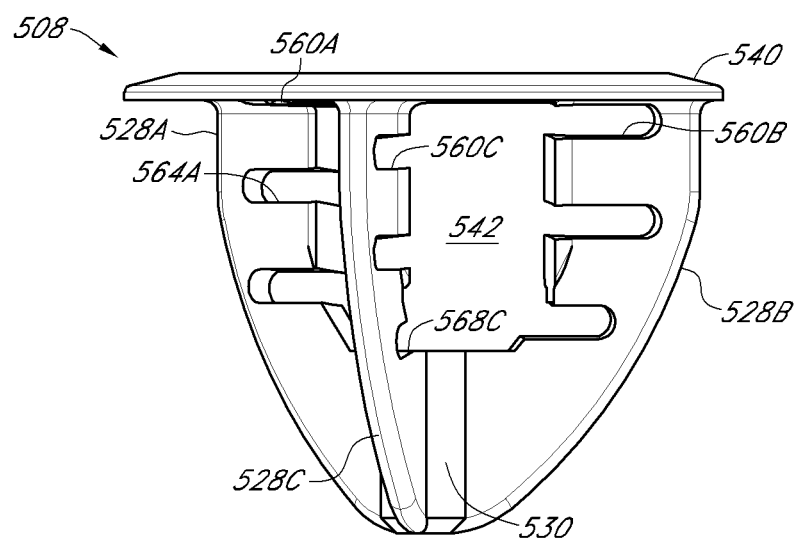
FIG. 13A is a side view of the base member of FIG. 12.

FIGS. 12, 13 and 13A show features of the base member 508 that facilitate delivery of the base member and/or the anchor member 512 over a guidewire. For example, the base member 508 has a plurality of arms 528A, 528B, 528C that extend between a distal and a proximal end 520, 524 of the base member 508. The arms 528A, B, C are coupled with a sleeve 530 disposed adjacent to the distal end 520 of the base member 508. The sleeve 530 has an opening at a proximal end 534 thereof extending into a lumen 538. The lumen 538 extends from the opening at the proximal end 534 to an opening at the distal end 520 of the sleeve 530. The lumen 538 is accessible through an open space 542 disposed between the arms 528A, B, C and between the proximal end 534 of the sleeve 530 and the proximal end 524 of the base member 508. The space 542 provides access to the lumen 538 by a direct path, e.g., a path perpendicular to the plane of the proximal end 524 of the base member 508.

FIG. 12 shows that the base member 508 includes a guide surface 548 and a lead surface 552 in some embodiments. The guide and lead surfaces 548, 552 can be regions of a continuous guide member and can be a continuous expanse without a change in orientation between them. The guide surface 548 can be substantially flat, e.g., disposed on a plane that is perpendicular to a longitudinal axis C of the lumen 538. The lead surface 552 can be angled to match the pitch of the helical protrusion 532 (see FIG. 14) on the anchor member 512. The guide member or the guide and lead surfaces 548, 552 can be disposed adjacent to a periphery of the base member 508, e.g., between a peripheral member 540 and the axis C. In one embodiment, the guide and lead surfaces 548, 552 are coupled at outer edges thereof with an inner edge of the peripheral member 540. In one embodiment, a circumferential gap 544 is provided between ends of the guide and lead surfaces 548, 552. The gap 544 is configured to permit the helical protrusion 532 (see FIG. 14) to be advanced along the lead surface 548 to a top laterally extending surface 560A of the first arm 528A, which is disposed beneath the gap 544.

FIG. 13A show the path from the lead surface 552 to the top surface 560A through the gap 544 is a first segment of a helical path about the axis C. A second segment of the helical path extends from the top laterally extending surface 560A to a top laterally extending surface 560B on the arm 528B. A third segment of the path extends from the top laterally extending surface 560B to a top laterally extending surface 560C of the arm 528C. A fourth segment of the path extends from the top laterally extending surface 560C to a laterally extending surface 564A of the arm 528A below the surface 560A. The laterally extending surface 564A is a mid-level surface on the arm 528A. The helical path through the base 508 extends in the same manner across a plurality of mid-level surface corresponding to the surface 564A and a plurality of surfaces at a lower level of the arms to a distal end point on or adjacent to or at a laterally extending surface 568C. The helical path described above accommodates a single helical protrusion, e.g., thread, of the anchor member 512. An advantage of this design is that only a single thread must traverse a gap in the proximal surface of the base portion 508. Also, the thread is much longer than the thread of the anchor member 112 and is generally at a shallower angle and so may be advanceable along the helical path with less torque than is required for the anchor member 112.

Figure 14:
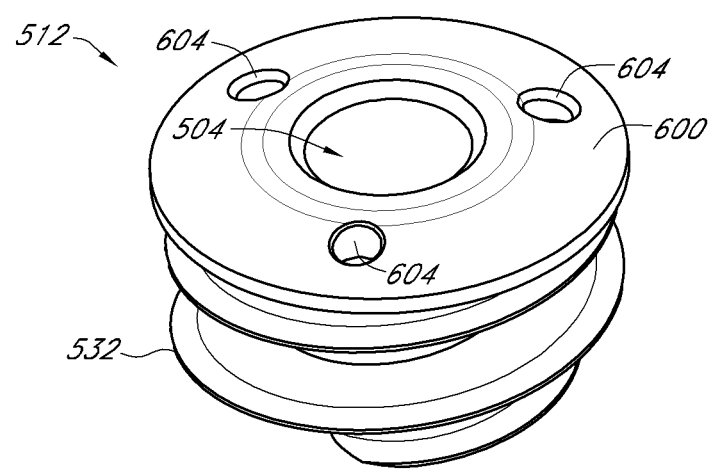
FIG. 14 is a top perspective view of an anchor member of the stemless humeral shoulder assembly of FIG. 11.
Figure 15:
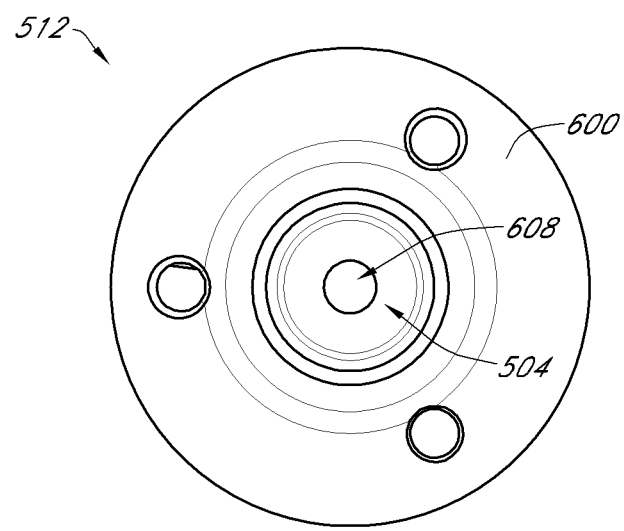
FIG. 15 is a top view of the anchor member of FIG. 14.

FIGS. 14 and 15 show further details of the anchor member 512. In particular, the anchor member 512 has a proximal face 600 having a tapered annular surface. The proximal face 600 can include a driver interface 604 that can take any suitable form, such as any of those described above. For example, driver interface 604 can include a plurality of recesses. FIG. 15 shows that the recess 504 can extend from the proximal face 600 to a distal end having an aperture 608 formed therein. The aperture 608 can be configured to receive a guidewire such that the anchor member 512 can be advanced over a wire, as discussed further below.

Figure 16A:
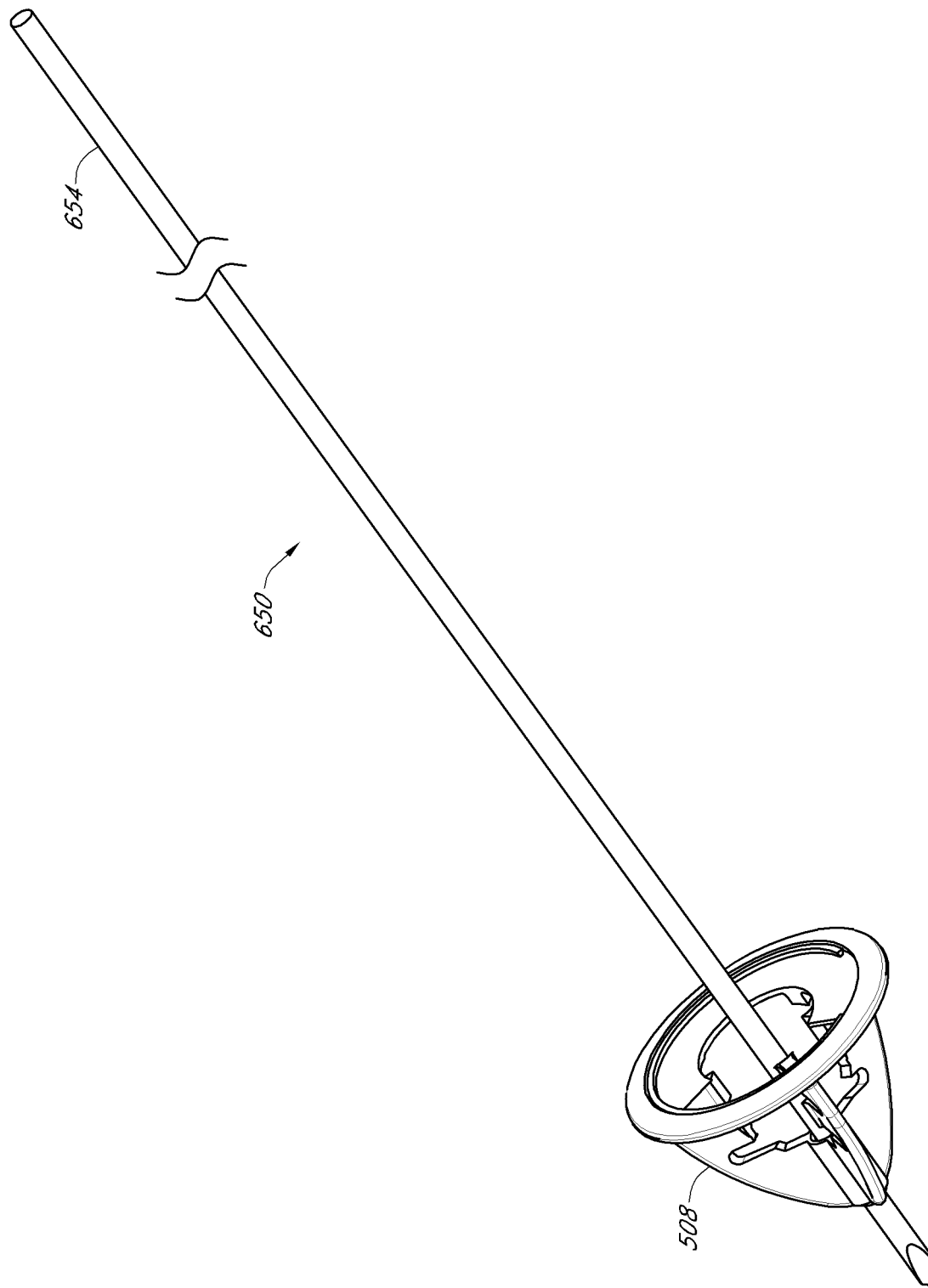
FIGS. 16A-16C illustrate steps of various methods of implantation of the stemless humeral shoulder assembly of FIG. 11.
Figure 16B:
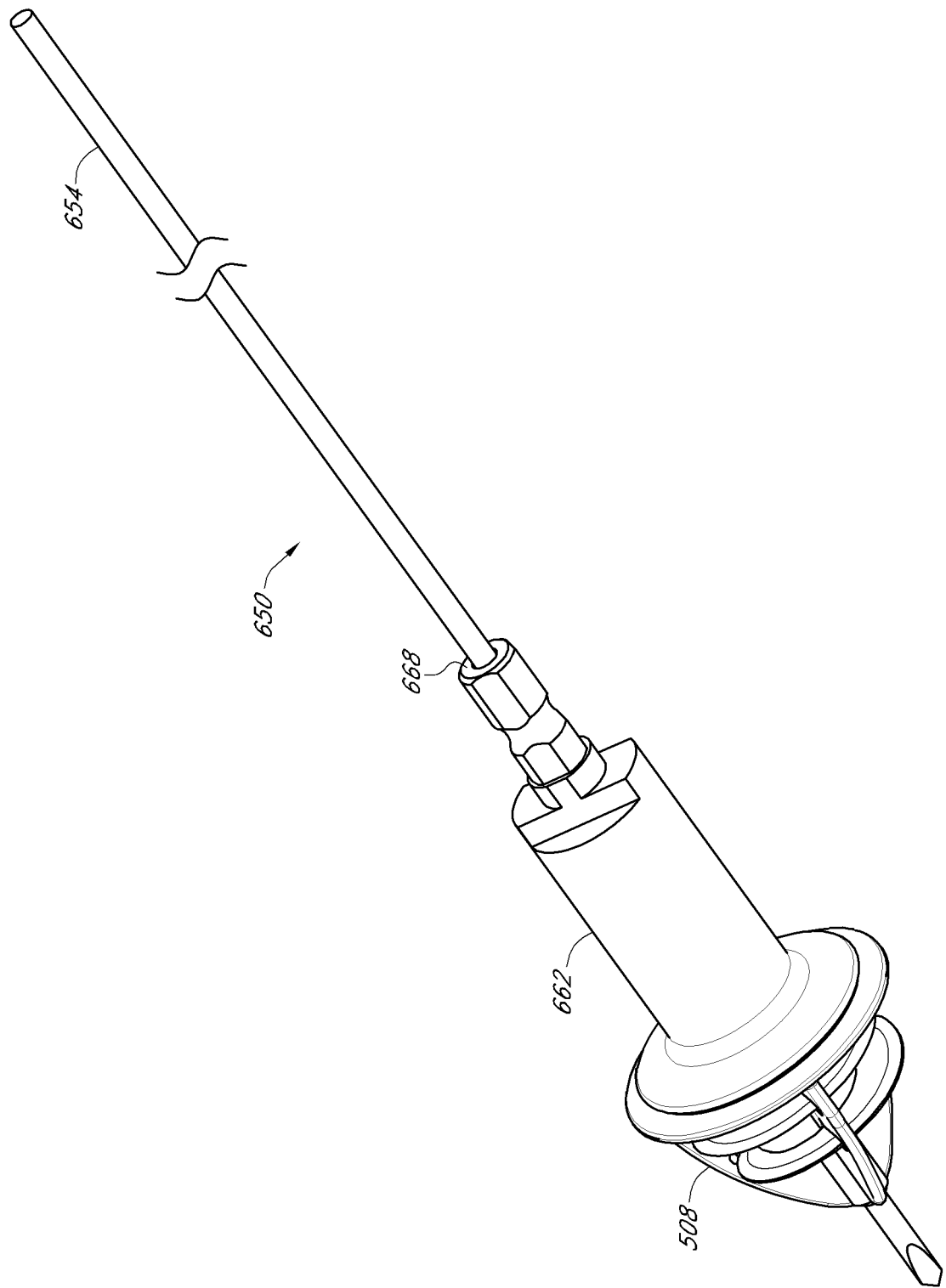
Figure 16C:
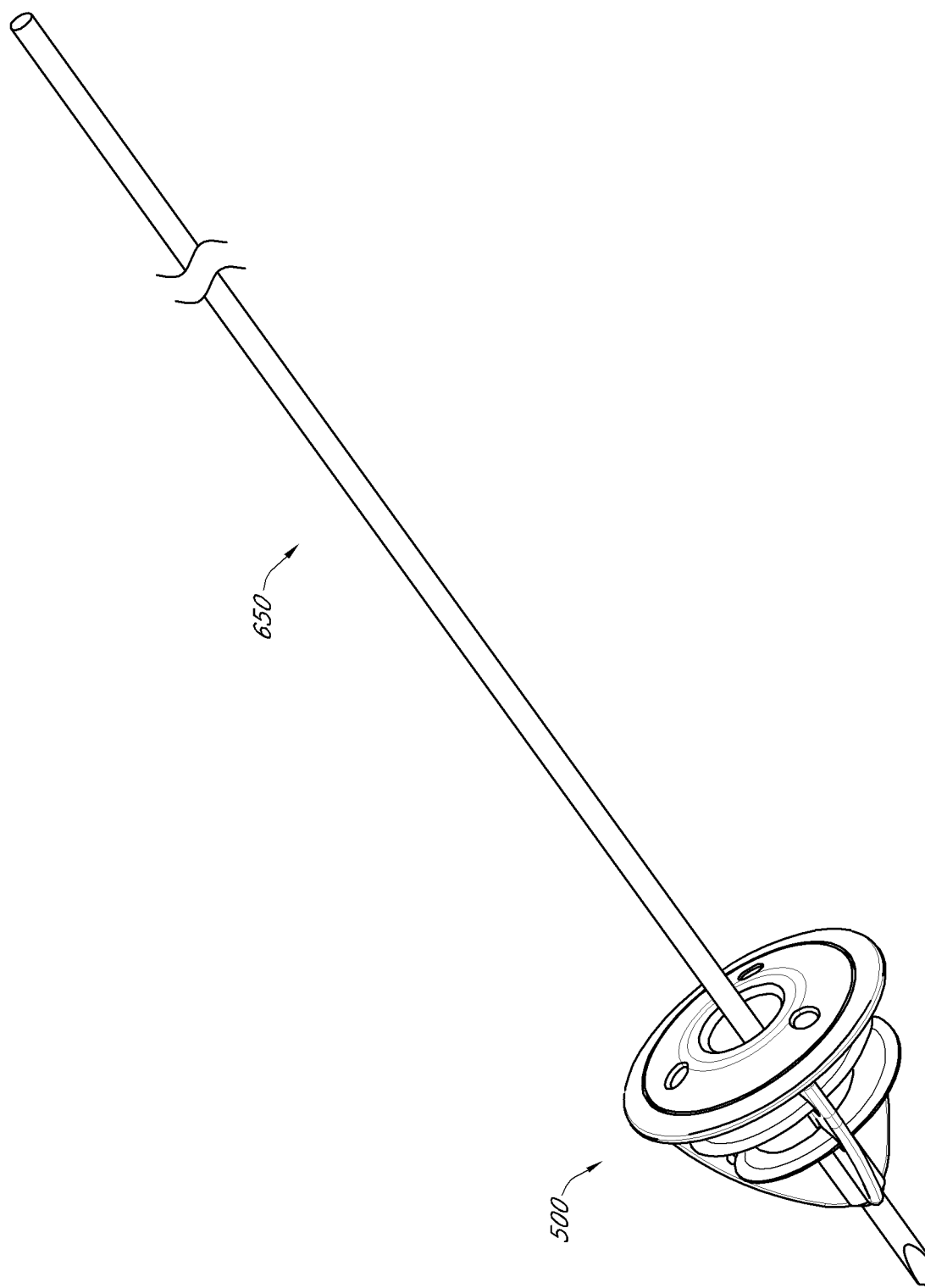

FIGS. 16A-C illustrate various methods of implanting the shoulder assembly 500. The method can include compatible steps of any of the methods discussed above in connection with FIGS. 10A-10H, including initial preparation of a humeral head with a recess to receive a guidewire 650. The guidewire 650 can take any suitable form and is sometimes known as a Kirschner wire or K-wire. The guidewire 650 is placed into a recess extending distally into a face of a humeral head. Once in place, the base member 508 is advanced over the proximal end 654 of the guidewire 650, e.g., an opening at the distal end of the lumen 538 is advanced over the proximal end 654 of the guidewire 650. The lumen 538 is sized so that the base member 508 can easily slide along the length of the guidewire 650 to a position corresponding to the position of the base member 108 in FIG. 10E.

Thereafter, the base member 508 is advanced into the bone. For example, if a recess have been formed that has a profile similar to that of the base member 508, the base member can be urged into the recess with low force, e.g., with hand force and without impactors or with light force from the impactor. In some methods, the gap 544 is oriented with respect to the anatomy. For example, the gap 544 can be disposed at a lower elevation (caudad) compared to the position of the guide surface 548.

FIG. 16B illustrates further step in which a cannulated driver 662 is advanced over the guidewire 650. The cannulated driver 662 preferably has an interface configured to mate with the driver interface 604 on the anchor member 512. The driver 662 can have a plurality of prongs extending distally therefrom to engage recesses in the face 600 of the anchor member 512. In one step, the surgeon couples the driver 662 with the anchor member 512. Once so coupled, the driver 662 and the anchor member 512 are advanced over the guidewire 650. An initial step of advancing the driver 662 and the anchor member 512 over the guidewire 650 includes inserting the proximal end 654 of the guidewire 650 into the aperture 608 in the anchor member 512. Continued advancement of the driver 662 and the anchor member 512 causes the guidewire 650 to be advanced through the driver 662 and out of a proximal end 668 thereof.

Once the driver 662 and the anchor member 512 are adjacent to the proximal portion of the base member 508, the distal portion of the helical protrusion 532 is placed against the guide surface 548 and/or the lead surface 552 and through the gap 544 and from there along the helical path discussed above. Once fully advanced, the cannulated driver 662 can be removed leaving the shoulder assembly 500 in place as shown in FIG. 16C. Thereafter the guidewire 650 is removed to allow subsequent steps to proceed, including attachment of a joint interface as discussed above.

Among the additional advantages of the shoulder assembly 500 is providing a single sleeve-like structure in the anchor member 512 rather than co-axial sleeve one in each of the base and anchor members. In particular, in the assembly 500 only the anchor member 512 includes a cylindrical structure. The cylindrical structure of the assembly 500 reinforces the helical protrusion 532 and also comprises the recess 504. This provides a simpler construction having fewer components. Also, there is no chance for multiple cylinders to be slid over each other to become misaligned, leading to binding or increased torque requirements for advancing the anchor member 512 into the base member 508.

III. Assemblies Having Reinforced Base Members

FIGS. 17-24B illustrate an embodiment of a humeral shoulder assembly 1000 in which distally projecting arms are more rigid by virtue of being coupled to each other and directly to a cylinder member at intermediate positions. This structure retains the direct bone engagement of exposed threads while making the arms more rigid.

Figure 17:
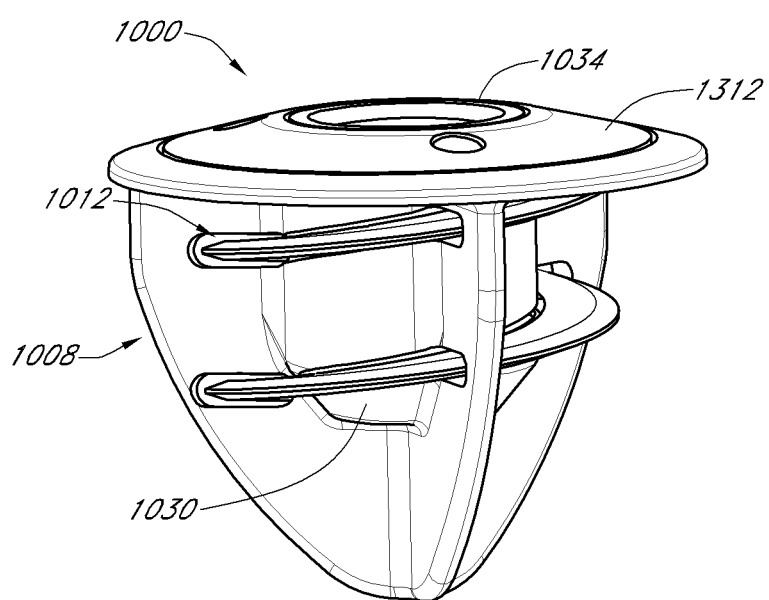
FIG. 17 is a top perspective view of another embodiment of a stemless humeral shoulder assembly.
Figure 18:
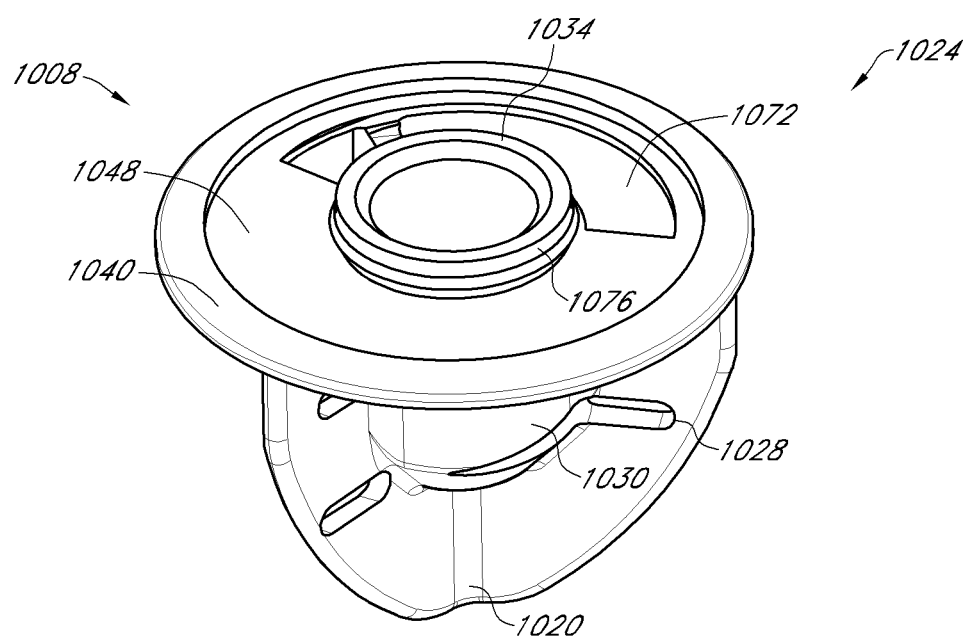
FIG. 18 is a top perspective view of a base member of the stemless humeral shoulder assembly of FIG. 17.

FIG. 17 illustrates the assembly 1000 having a base member 1008 and an anchor member 1012. The base member 1008 and the anchor member 1012 are separable components that can be applied to the patient separately, e.g., assembled in multiple steps within the bone in techniques similar to those discussed above.

FIGS. 18-22 illustrate various views of the base member 1008. The base member 1008 has a distal end 1020 configured to be embedded in bone and a proximal portion 1024 to be disposed adjacent to the face F of the humerus H or another bone surface.

Figure 20:
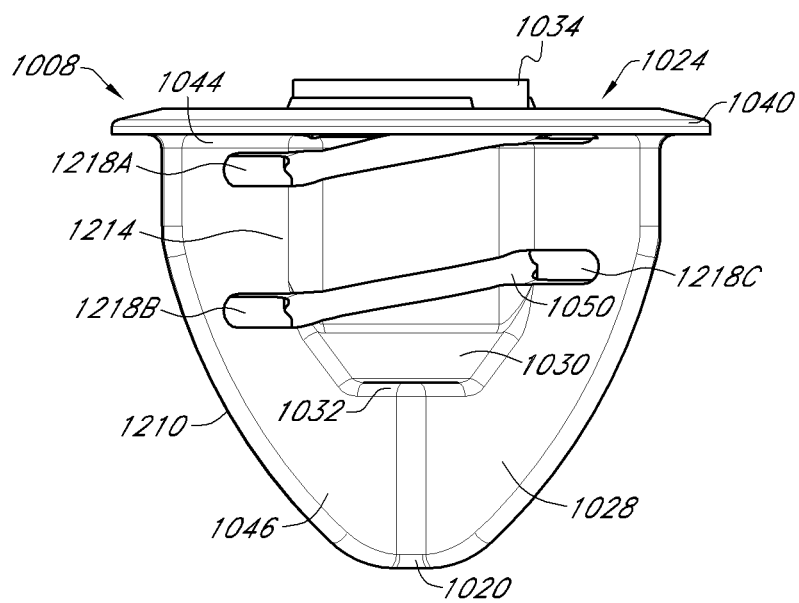
FIG. 20 is a side view of the base member of FIG. 18.
Figure 21:
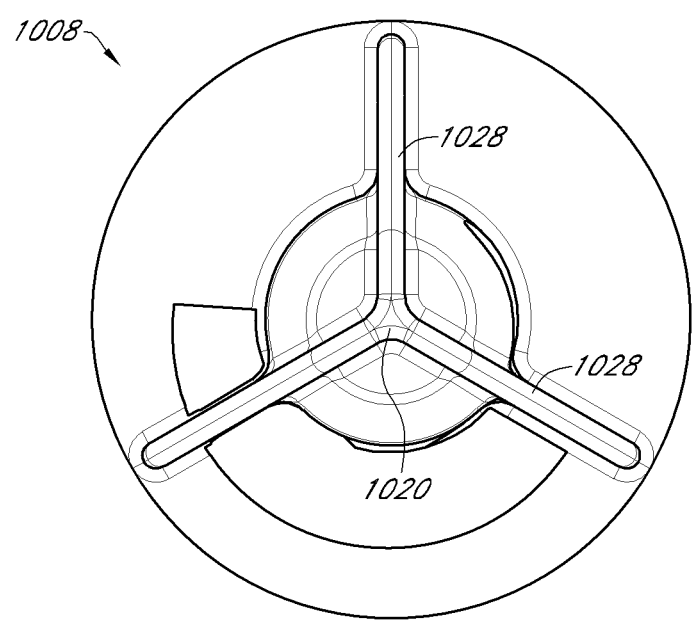
FIG. 21 is a bottom view of the base member of FIG. 18.

As shown in FIG. 20, the base member 1008 can have a plurality of spaced apart arms 1028 projecting from the proximal portion 1024 to the distal end 1020 of the base member 1008. Each arm 1028 can define an outer edge 1210 having an arcuate sloping surface. The sloping surface can facilitate insertion of the base member 1008 into an exposed humeral face F as discussed above in connection with FIGS. 10A-10H. Further, each arm can define an inner edge 1214. The inner edge 1214 of a distal portion 1046 of each of the arms can be connected to form the distal end 1020 of the base member 1008 (see FIG. 21).

The inner edge 1214 of each arm 1208 can include one or more laterally extending recesses 1218A, 1218B, 1218C. The number of laterally extending recesses can vary between different arms 1028. For example, as shown in FIG. 20, a first arm can include a first recess 1218A and a second recess 1218B, while a second arm can include only one recess 1218C. The recesses 1218A, 1218B of the first arm can be longitudinally displaced from the recess 1218C of the second arm to accommodate a helical structure 1304 of the anchor member 1012 (see FIG. 17). Additionally, the outermost edge of each of the laterally extending recesses 1218A, 1218B, 1218C can be equidistant from the longitudinal axis of the base member 1008 to accommodate an anchor member 1012 having a substantially constant outer diameter along the helical structure 1304 (see FIG. 17).

Figure 22:
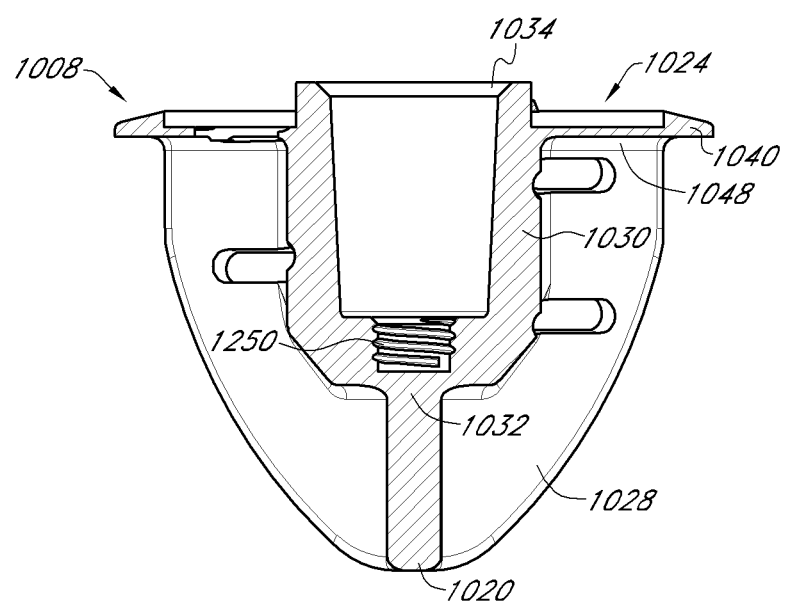
FIG. 22 is a cross-sectional view of the base member of FIG. 19 along line 22-22.

The base member 1008 can also include a central portion (e.g., a cylindrical member 1030). As shown in FIG. 22, the cylindrical member 1030 can include an open proximal end 1034 and a closed distal end 1032. The proximal end 1034 can define the proximal-most point of the base member 1008. In certain aspects, the proximal end 1034 can include an annular groove 1076 (FIG. 18) for receiving a c-ring that may be present to prevent loosening between the anchor member 1012 and the base member 1008. A c-ring can be part of a locking device, as discussed further in connection with FIGS. 27-27A below. Further, a threaded recess 1250 can be formed in the distal portion of the cylindrical member 1030. The threaded recess 1250 enables a component to be advanced into a secure position of engagement with the base 1008. The component can be part of a prosthetic joint interface or can be a tool used in placement of the shoulder assembly 1000. For example, as shown in FIG. 24A, the recess 1250 can engage a guide tool 432 (FIG. 25). The guide tool 432 can extend the length of the cylindrical member 1030 to facilitate insertion of the anchor member 1012 into the base member 1008.

FIG. 20 shows that the outer wall of the cylindrical member 1030 can define a helical channel 1050 (e.g., groove or opening). The outer wall of the cylindrical member 1030 can connect to the inner edge 1214 of the arms 1028, such that portions of the helical channel 1050 can align with each of the laterally extending recesses 1218A, 1218B, 1218C to form a pathway for the helical structure 1304 of the anchor member 1112 (see FIG. 17).

Figure 19:
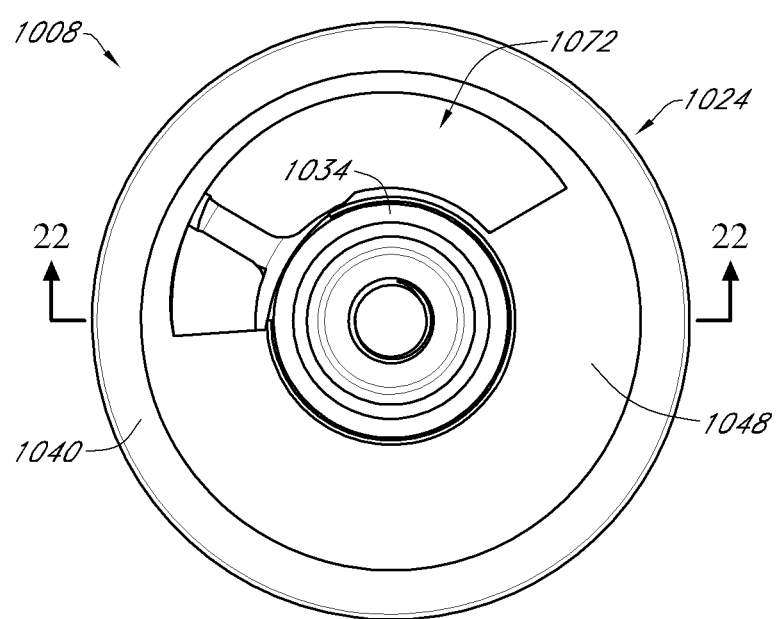
FIG. 19 is a top view of the base member of FIG. 18.

FIG. 19 illustrates that the proximal portion 1024 of the base member 1008 can include a peripheral member 1040 disposed about the outer periphery of the proximal portion 1024. The peripheral member 1040 can be coupled with the proximal ends of the arms 1028 (see FIG. 22) to provide a unitary structure. As shown in FIG. 19, the proximal portion 1024 can include a guide member 1048 that can be connected to the peripheral member 1040. The guide member 1048 can be partially recessed from the proximal face of the peripheral member 1040 to provide a space into which a proximal disc structure 1312 of the anchor member 1012 can be positioned (see FIG. 17). Further, the guide member 1048 can include a plate-like projection extending radially inwardly from the peripheral member 1040 to a proximal portion of the cylindrical member 1030. For instance, the guide member 1048 can extend continuously from the inner edge of the peripheral member 1040 to the cylindrical member 1030 around at least about 50% of an inner diameter of the peripheral member 1040. In an arcuate segment, the guide member 1048 can extend discontinuously from the inner edge of the peripheral member 1040 to the cylindrical member 1030. For example, a gap 1072 can be defined adjacent to but radially inward of an arcuate segment of the guide member 1048 that is disposed between the peripheral portion 1040 and the gap 1072. The gap 1072 facilitates insertion of the anchor member 1012 into the base member 1008.

As shown in FIG. 20, the proximal end 1034 of the cylindrical member 1030 can be elevated above the proximal-most aspect of the peripheral member 1040. When the anchor member 1012 is connected to the base member 1008 (see FIG. 17), the proximal disc structure 1312 can fill the annular space bounded by the outside surface of the cylindrical member 1030 and the inside surface of the peripheral member 1040 to create a tapered, annular surface from proximal end 1034 of the cylindrical member 1030 to the peripheral member 1040. This structure avoids inflection points in the side profile of the assembly 1000, which is advantageous in reducing or eliminating gaps between the assembly 1000 and another component of a shoulder joint assembly coupled therewith.

Figure 23:
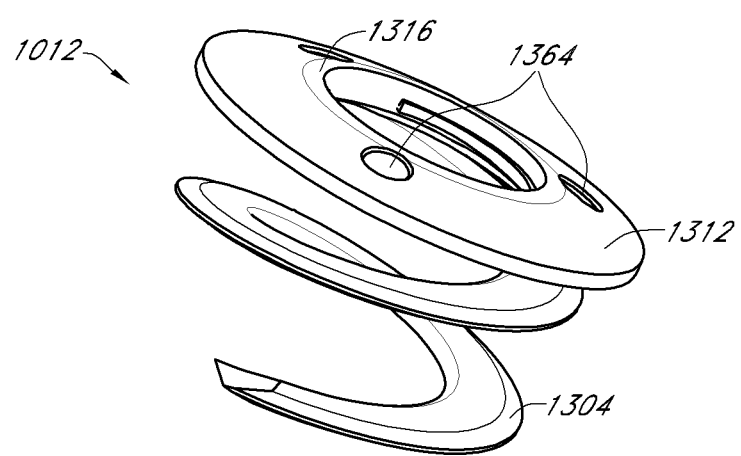
FIG. 23 is a top perspective view of an anchor member of the stemless humeral shoulder assembly of FIG. 17.

FIG. 23 illustrates features of the anchor member 1012, which has a proximal disc structure 1312. The proximal disc structure 1312 can define a central opening 1316 that can surround the proximal end 1034 of the cylindrical member 1030 when the shoulder assembly 1000 is assembled. Further, the proximal disc structure 1312 can include a driver interface 1364 (e.g. a plurality of openings) for engaging a driving tool 450 (see FIG. 24B). Rotating the driving tool 450 can advance the anchor member 1012 to rotationally engage the base member 1008.

The anchor member 1012 can also include a continuous helical structure 1304 disposed distally of the proximal disc structure 1312. In this embodiment, the anchor member 1012 has a single helical structure 1304. Other embodiments can have a multiple helices, e.g., including a double helix, a triple helix, or a quadruple helix configuration. The inner edge of the helical structure 1304 can define the innermost edge of the anchor member 1012 distal of the disc structure 1312 in that the anchor member 1012 does not include a central body structure. In at least this sense, the anchor member 1012 has an open helix construction. The helical structure 1304 defines a substantially constant inner diameter and a substantially constant outer diameter in one embodiment.

When the shoulder assembly 1000 is assembled, the disc structure 1312 can abut the guide member 1048 of the base member 1008 and the helical structure 1304 can be disposed in the helical groove 1350 and the laterally extending recesses 1218A, 1218B, 1218C of the base member 1008 (see FIG. 17). Portions of the helical structure 1304 project into the open area defined between the arms 1208 and engage the bone, thereby increasing the initial pull-out force of the assembly 1000 when initially placed. As shown in FIG. 26, the peak force corresponding to the initial pull out force 1520 of the shoulder assembly 1000 is at least five times greater than the peak force corresponding to the initial pull out force 1500 of the prior art.

Figure 24B:
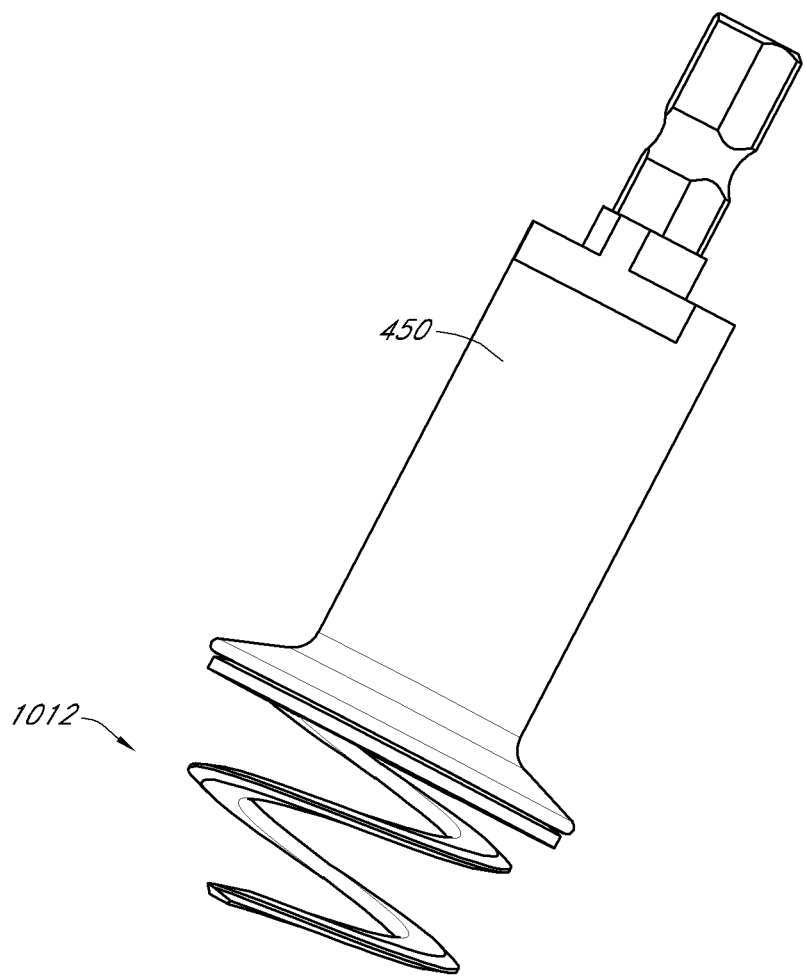

FIGS. 24A-24B illustrate tools that can be used to implant the shoulder assembly 1000 and corresponding methods. The method of using the tools can include compatible steps of any of the methods discussed above in connection with FIGS. 10A-10H including creating a recess CR in the humeral head (see FIG. 10D). Once the recess CR is created, the base member 1008 can be inserted into the face F of the humerus head h (similar to FIG. 10E). Preferably, the insertion of the base member 1008 can be achieved without an impactor or any other tools, but rather just inserted by hand force.

After the base member 108 has been inserted into the recess CR, a subsequent step can involve coupling the guide tool 432 with the base member 1008 (see FIG. 24A). As described above, FIG. 25 illustrates one embodiment of the guide tool 432. The guide tool 432 can extend the length of the cylindrical member 1030 to guide the anchor member 1112 into the base member 1008. To advance the anchor member 1012 over the guide tool 432, the method can include coupling a driver 450 with the driver interface 1364 (see FIG. 24B). The driver 450 can take any suitable form, e.g., can include a plurality of protrusions configured to mate with openings of the driver interface 1364. Preferably, the driver 450 has a ratchet mechanism such that the surgeon can continuously hold the tool and need not release the handle to re-grip it. Once the shoulder assembly 1000 is assembled, the driver 450 and the guide tool 432 can be removed.

The methods described above, e.g., in connection with FIGS. 24A-24B, can include additional steps and employ additional tools as discussed above. The shoulder assembly 1000 and/or the tool 450 also can be adapted to be compatible with other methods, e.g., with over-the-wire methods. For instance, the base member 1008 can have a lumen extending through the distal end 1020 to guide the base member into place. A channel in the tool 450 can be used in guiding the anchor member 1012 into place in the base member 1008.

IV. Locking Devices to Reduce or Eliminate Disengagement of Base and Anchor Members FIGS. 27-32 show features that can reduce or eliminate disengagement between a base member and an anchor member. These embodiments are illustrated in connection with the shoulder assembly 100, but can be used in connection with any of the embodiments herein. Also, although the features are discussed separately they could be combined in some embodiments.

Figure 27:
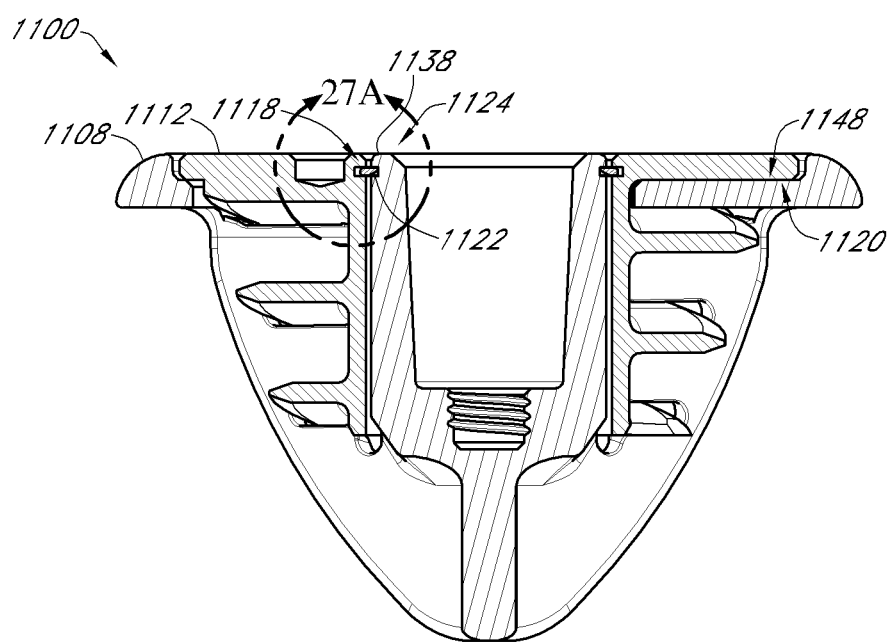
FIG. 27 is a cross-sectional view of another embodiment of a shoulder assembly having a locking device disposed between a base member and an anchor member thereof to reduce or eliminate disengagement of the anchor member from the base member.
Figure 27A:
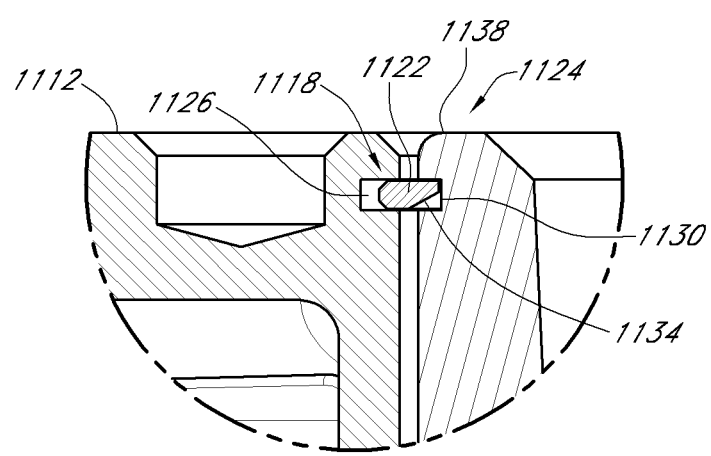
FIG. 27A is an enlarged view of the locking device shown in FIG. 27 taken through line 27A-27A.
Figure 28:
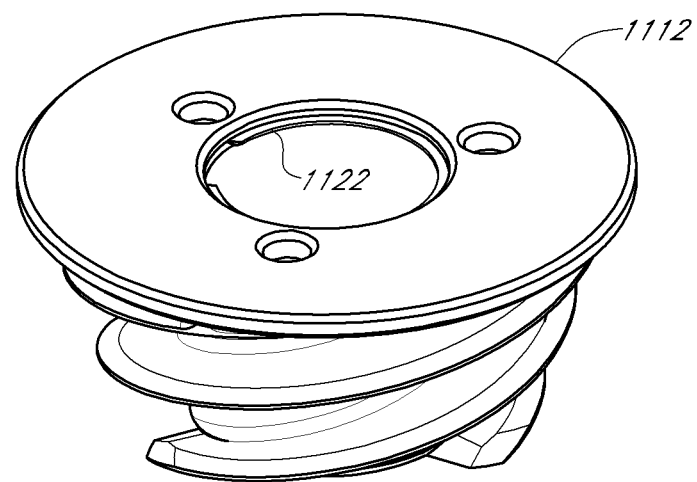
FIG. 28 is a top perspective view of an anchor member assembly of the shoulder assembly of FIG. 27.

FIGS. 27 and 27A shows a shoulder assembly 1100 that includes a base member 1108, an anchor member 1112, and a locking device 1118 disposed adjacent to a proximal end 1124 of the base member 1108. The locking device 1118 comprises a C-ring 1122 that is disposed partially in a recess or groove 1126 (See FIG. 27A) of the anchor member 1112 and partially in a groove 1130 (see FIG. 27A) of the base member 1108. FIG. 28 shows a partial assembly in which the C-ring 1122 is coupled with the anchor member 1112 prior to coupling the anchor member 1112 to the base member 1108. In the illustrated embodiment, the C-ring 1122 is disposed in the anchor member 1112 prior to implantation. FIG. 27A shows that the cross-sectional shape of the C-ring 1122 facilitates actuation of the C-ring 1122 during assembly. A distal face 1134 of the C-ring 1122 is angled relative to a plane oriented perpendicular to the distal-proximal direction of the assembly 1100. In assembly, the anchor member 1112 is advanced into the base member 1108 until the distal face 1134 engages a proximal portion 1138 (See FIG. 27A) of the base member 1108 and is deflected thereby into or deeper into the recess 1126 of the anchor member 1112. This permits the anchor member 1112 to move relative to the base member 1108 until the C-ring 1122 moves to the position of the groove 1130. The resilience of the C-ring 1122 causes the C-ring to return to an un-deflected configuration thereof. FIG. 27A shows the final position of the C-ring 1122 with a portion disposed in the groove 1130 and a portion disposed in the groove 1126. In this configuration, the anchor member 1112 is locked into the base member 1108 because further advancement of the anchor member 1112 into the base member 1108 is prevented by contact between a base face 1148 and an anchor face 1120 and because retraction of the anchor member 1112 from the base member 1108 is prevented by the C-ring 1122 in cooperation with grooves 1126 and 1130 (see FIG. 27).

In other embodiments, the C-ring 1122 can be coupled with the base member 1108 prior to assembly of the anchor member 1112 with the base member 1108. In such embodiments, a surface of the anchor member 1112 can be configured to deflect the C-ring 1122 into or deeper into the groove 1130. In such embodiments, a proximal face of the C-ring 1122 may be angled relative to a plane oriented perpendicular to the distal-proximal direction of the assembly to facilitate deflection of the C-ring. Although a C-ring is illustrated, other structures that can be temporarily deflected into the recess 1126 or the recess 1130 can be used, such as spring loaded or resilient detents or members or other similar structures.

Figure 29:
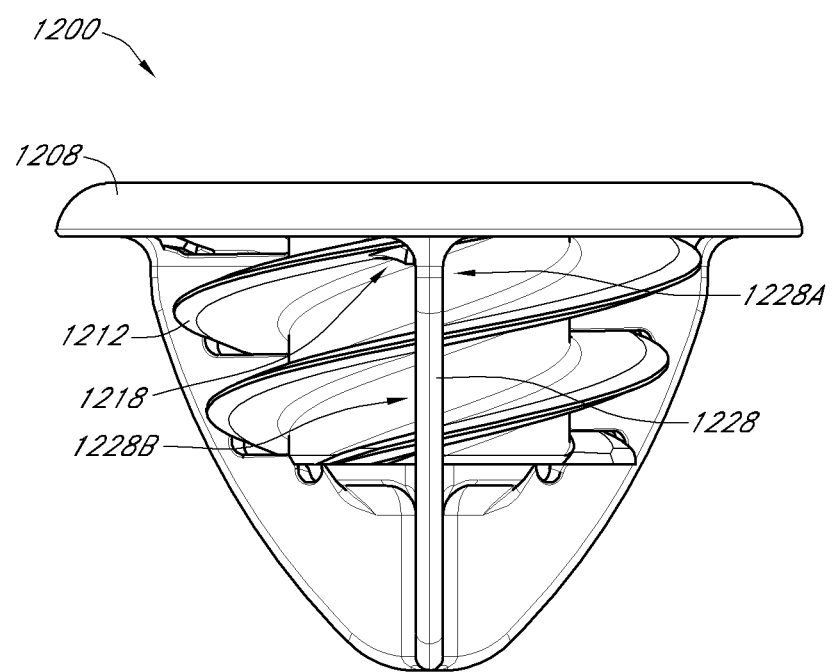
FIG. 29 is a side view of a shoulder assembly having another embodiment of a locking device.
Figure 30:
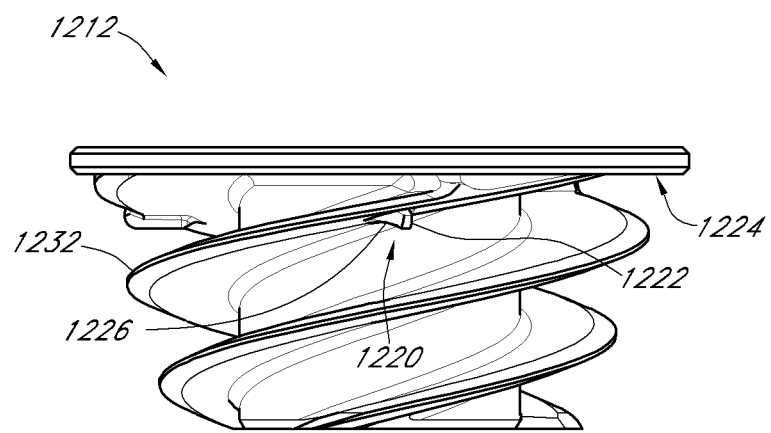
FIG. 30 is a side view of an anchor member of the shoulder assembly of FIG. 29.

FIGS. 29 and 30 illustrate another embodiment of a shoulder assembly 1200 that has a base member 1208, an anchor member 1212, and a locking device 1218 comprising an interface between the anchor member 1212 and the base member 1208. The locking device 1218 includes a distal projection 1220 disposed on a distal side of a helical protrusion 1232 (see FIG. 30). FIG. 30 shows that the distal projection 1220 can have a first face 1222 that is oriented generally proximal to distal and a second face 1226 that is disposed at an angle relative to a plane extending perpendicular to the proximal-distal direction of the anchor member 1212.

In use, the anchor member 1212 is advanced into the base member 1208 in the same manner as described above in connection with the assembly 100. As the anchor member 1212 approaches the fully engaged position, the second face 1226 of the projection 1220 approaches a first side 1228A of the arm 1228 of the base member 1208. The second face 1226 passes across a lower lateral face of an upper-most slot of the arm 1228. As the second face 1226 crosses the arm 1228 from the first side 1228A, local deformation of at least one of the arm 1228 and the projection 1220 permits further advancement of the second surface 1226 relative to the arm until the first surface is disposed on the second side 1228B of the arm 1228 (see FIG. 29). The local deformation is preferably temporary such that the deformed structure(s) return toward their undeformed state(s). Once disposed on the second side 1228B of the arm 1228, the first face 1222 abuts a corresponding surface of the second side 1228B of the arm 1228. In this configuration, the anchor member 1212 is locked into the base member 1208 because further advancement of the anchor member 1212 into the base member 1208 is prevented by contact between an upper surface of the base member 1208 and an anchor face 1224 and because retraction of the anchor member 1212 from the base member 1208 is prevented by contact between the first face 1222 and the second side 1228B of the arm 1228.

The locking device 1218 is simple in construction in that a first portion of the interface is disposed on the anchor member 1212 and a second portion of the interface is disposed on the base member 1208 and thus does not require another separable component compared to the shoulder assembly 1100. Also, the locking device 1218 does not require an additional discrete step in the locking of the base member 1208 to the anchor member 1212 because the final step of passing the projection 1220 from the first side 1228A to the second side 1222B is accomplished with the same rotation as is required in connection with the assembly 100, though some additional force may be required to provide the local deformation discussed above.

Figure 31:
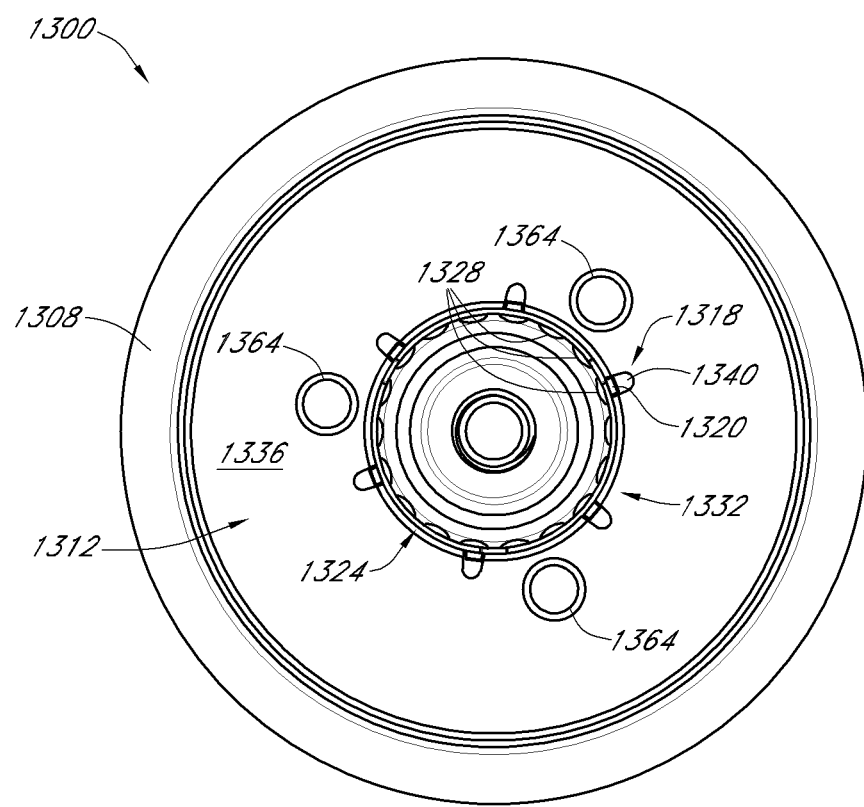
FIG. 31 is a top view of a shoulder assembly having another embodiment of a locking device.
Figure 32:
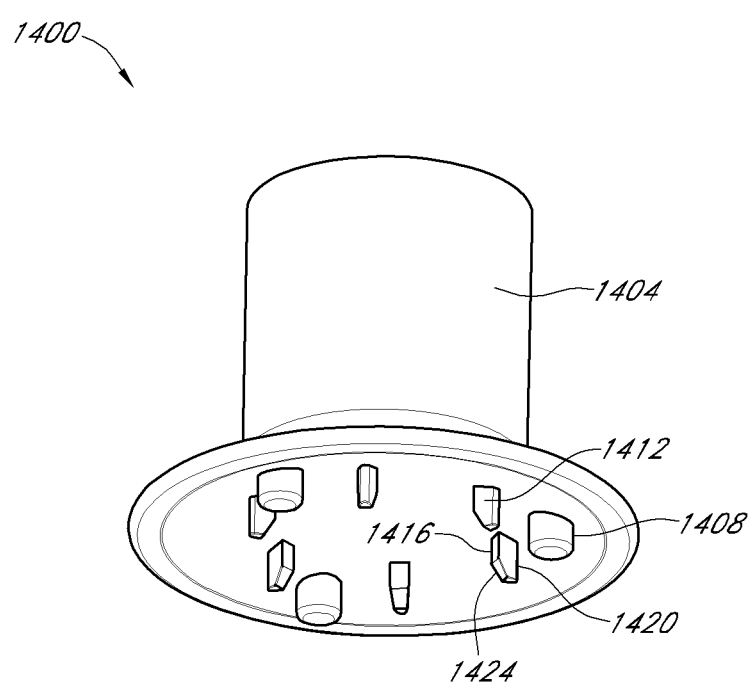
FIG. 32 is a bottom perspective view of a tool for actuating a locking structure of the locking device of the shoulder assembly of FIG. 31 from a disengaged configuration to an engaged configuration.

FIGS. 31 and 32 show another embodiment of a shoulder assembly 1300 that has a base member 1308, an anchor member 1312, and a locking device 1318 comprising at least one, e.g., a plurality of deflectable prongs 1320 that can be deployed to span from one of the anchor member 1312 and the base member 1308 to the other of the anchor and base members. The spanning of the prong(s) 1320 causes a portion of the prong to be engaged with the base member 1308 and another portion to be engaged with the rotatable anchor member 1312 such that rotation of the anchor member in either direction is reduced or eliminated.

FIG. 31 shows that the prongs 1320 can be disposed on the anchor member 1312 about an inner periphery 1332 of a disc structure 1336 thereof. The base member 1308 can have a cylindrical member 1324, similar to that discussed above in connection with the assembly 100. The cylindrical member 1324 can have a plurality of scallops or recesses 1328 disposed on a side surface thereof. The recesses 1328 can extend entirely around the cylindrical member 1324 in one embodiment to enable the prong(s) 1320 to be engaged at a nearest recess 1328 rather than come precisely to rest at a specific rotational position and recess. In other embodiments, the base and anchor members 1308, 1312 could be provided with the same number or prongs and recesses, wherein the location of the prongs and recesses are provided at an expected fully engaged position of the anchor member 1312 relative to the base member 1308.

FIG. 31 shows the prong(s) 1320 in a disengaged position. Any suitable technique or tool can be used to deploy the prongs 1320 across a gap between the anchor member 1312 and the base member 1308. FIG. 32 illustrates a tool 1400 that can be used to deploy the prongs 1320. The tool 1400 includes a proximal user grip portion 1404, which can be a cylindrical member or any other ergonomic gripping structure. The tool 1400 also includes a plurality of pins 1408 disposed on a distal portion thereof that are configured and positioned to engage driver interfaces 1364 disposed on the proximal face of the disc structure 1336. The pins 1408 can be on an opposite side of the tool 1400 from the grip portion 1404. The tool 1400 also includes a plurality of prong actuators 1412 disposed on the same side of the tool as are the pins 1408. The prong actuators 1412 can each include a first, radially inward side 1416 and a second, radially outward side 1420. An angled surface 1424 is disposed between the sides 1416, 1420. The angled surface 1424 is configured to engage the prongs 1320 and deflect and in some cases deform them as the tool 1400 is advanced. For example, the radially outward side 1420 is configured and positioned to be inserted into a recess 1340 disposed in the proximal faces of the disc 1336 radially outward of the prongs 1320. This initial insertion of the prong actuator 1412 into the recess 1340 can be up to a point where the angled surface 1424 first engages the prong 1320. The radial distance from the first, radially inward side 1416 to the second, radially outward side 1420 is greater than the radial extent of the recess 1340. The radial distance from the first, radially inward side 1416 to the second, radially outward side 1420 spans the recess 1340, the gap between the anchor and base members 1312, 1308 and into the scallop or recess 1328. Further advancement of the tool 1400 causes the angled surface 1424 to engage the prong 1320. Still further advancement of the tool 1400 causes the prong 1320 to be deflected, e.g., bent or otherwise deformed into the recess 1328 of the base member 1308. When so deflected, the prong 1320 spans from the disc structure 1336 of the anchor member 1312 to the recess 1328 of the base member 1308. Because the base member 1308 is fixed in the bone, the coupling of the prong 1320 with the base member 1308 causes the anchor member 1312 also to be fixed relative to the bone. This prevents any backing out or unintended disengagement of the anchor member 1312 from the base member 1308.

As illustrated, one embodiment of the locking device 1318 comprises six prongs 1320. In other embodiments, one prong 1320 can be provided. In other embodiments, a plurality of prongs, e.g., two three, four, five, twenty, or more prongs 1320 can be provided. The prongs 1320 could be disposed on the base member 1308 and could be deflected, e.g., bent or otherwise deformed, into a scallop or recess disposed on the anchor member 1312 in other embodiments. In further embodiments, the prong 1320 can be configured as a spanning member that need not be formed as a part of either the base member 1308 or the anchor member 1312 but rather as a separate components installed at the proximal side of the assembly 1300. As discussed above, the various locking devices discussed herein can be combined to provide multiple locking structures.

V. Anchor Members which Lock to Stems

Figures 33, 34:
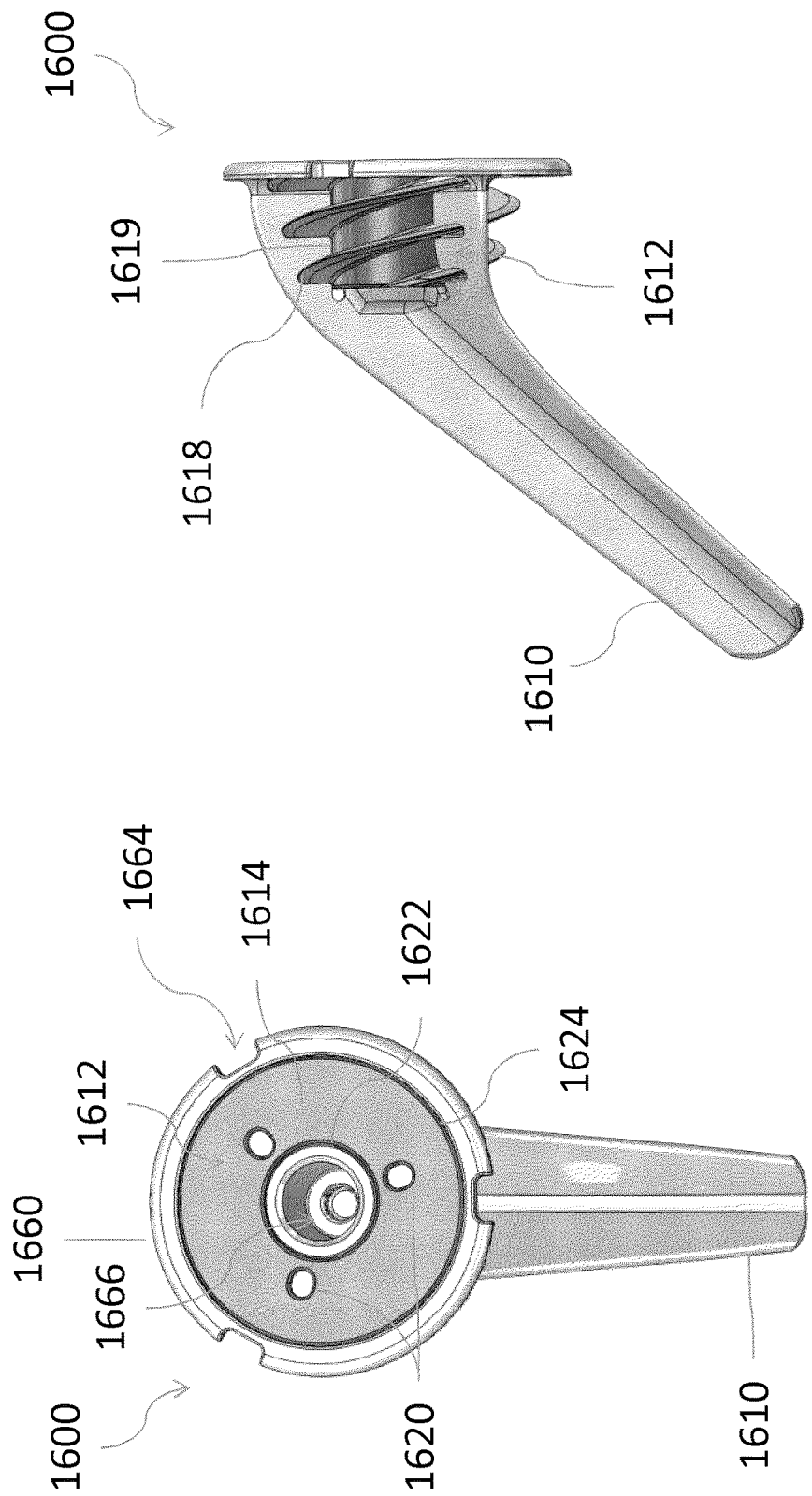
FIGS. 33 and 34 are a top perspective and side views of a humeral implant including the anchor member.
Figure 35:
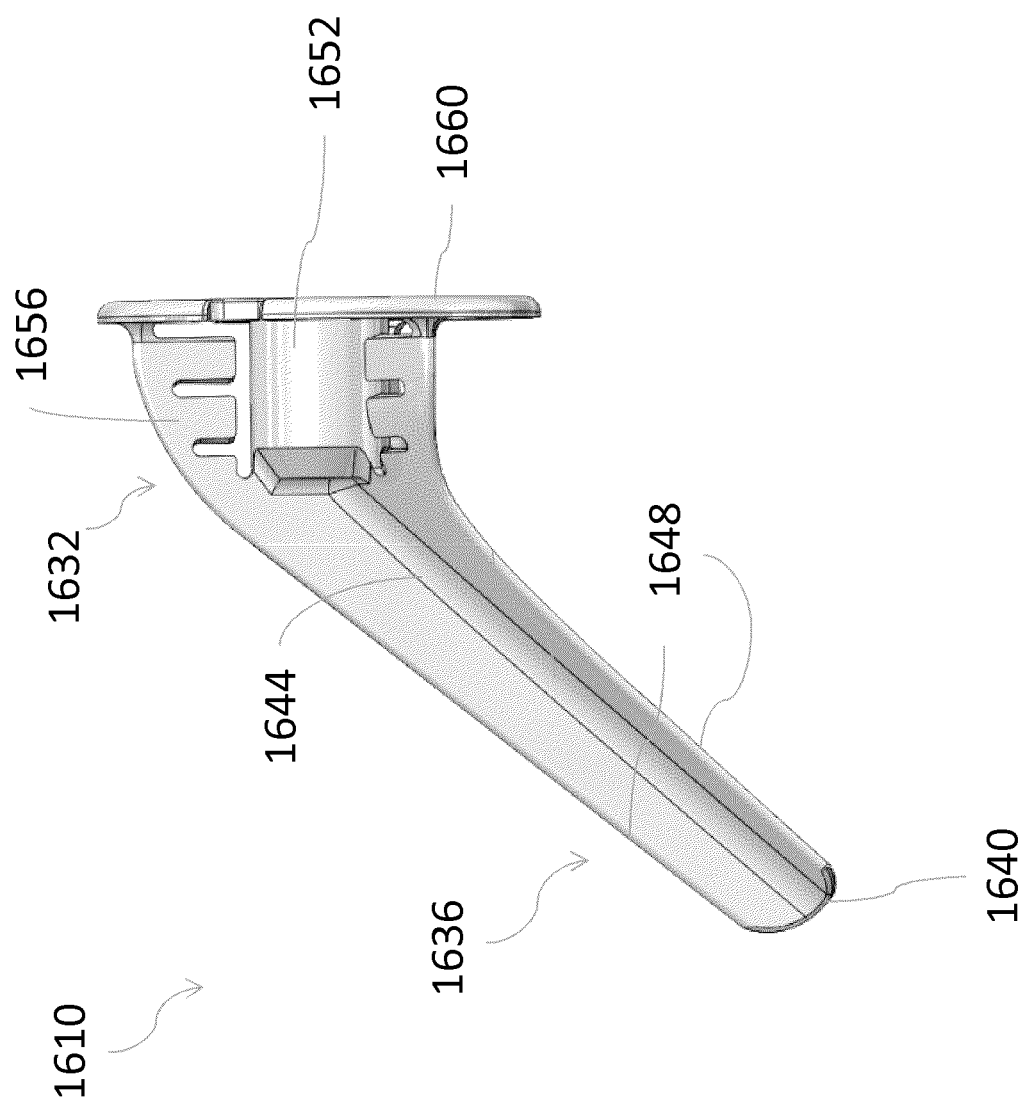
FIG. 35 is a side view of a stem of the humeral implant of FIG. 33 without anchor member.

As demonstrated above, the unique anchor and base members described herein provide for excellent securement of joint implant to bone, e.g., of humeral implants to a resected humerus. The excellent securement provided by these implants is provided immediately after a procedure without the need to wait for bone ingrowth. FIGS. 33-35 illustrate a humeral implant 1600 and components thereof. The humeral implant 1600 includes a stem and that combines the securement benefits of a stem with the securement benefits of the base and anchor member as discussed herein.

FIGS. 33 and 34 show the humeral implant 1600 includes a stem 1610. The implant 1600 also includes an anchor member 1612. As discussed further below, the anchor member 1612 is similar to other anchor members discussed above. The description of the features of the other anchor members discussed herein may be combined with or substituted for the features of the anchor member 1612 described below.

The anchor member 1612 has a proximal face 1614 and a distal threaded portion 1618. The distal threaded portion 1618 can have a radially inner edge coupled with a cylindrical portion 1619 of the anchor member 1612. A radial outer edge and an expanse between the inner and outer edges of the threaded portion 1618 are adapted to be advanced into and then to be embedded in bone. The implant 1600 provides high confidence in securement by combining the engagement between the threaded portion 1618 and the bone matter in the metaphysis with engagement between the distal portion 1636 of the stem 1610 and the bone matter surrounding the canal of the humerus. In the event the engagement between the threaded portion 1618 and the bone matter of the metaphysis is not sufficient, the stem 1610 provides additional securement. See FIG. 26 and corresponding discussion for details of securement using such a threaded portion. The proximal face 1614 can have a tool interface 1620 that can be engaged by a driver to advance the anchor member 1612 into or remove the anchor member from the stem 1610. FIG. 34 shows that the proximal face 1614 can be flush with a proximal portion of the stem 1610 when fully advanced. That is, the face 1614 can be positioned so that it does not protrude proximally of a proximal most aspect of the stem 1610, which is discussed further below. FIG. 33 shows that the proximal face 1614 can be annular, providing an inner edge 1622 that allows access to a portion of the stem 1610 as discussed below. The inner edge 1622 can be disposed at the proximal end of the cylindrical portion 1619. In one embodiment, the cylindrical portion 1619 projects from the inner edge 1622. FIG. 33 also shows that the proximal face 1614 includes an outer edge 1624 that can be received by and in some cases surrounded by an outer periphery of a proximal portion of the stem 1610.

The stem 1610 is advantageous in providing multiple modes of securement to a bone, e.g., to a proximal humerus. Compared to the aforementioned stemless designs, the stem 1610 gives a surgeon an option in evaluating a patient to be able to quickly adapt a surgical plan to an implant providing more security or providing security to a different bone segment, such as a canal which may be more robust than the cancellous bone disposed at or just beneath the resection plane. FIG. 35 shows that the stem 1610 includes a proximal portion 1632 and a distal portion 1636. The distal portion 1636 is configured to be inserted through cancellous bone, for example through a resected humerus of a patient. A distal tip 1640 of the distal portion 1636 can be inserted to extend into an intramedullary canal of the humerus. In some embodiments the distal portion 1636 includes a central portion 1644 extending proximally from the distal tip 1640, with one or more projections 1648 extending away from the central portion 1624. The projections 1648 can include two, three, four or more projections 1648. In some embodiments, the projections 1648 are evenly spaced around the central portion 1644. For example, if there are three projections 1648, they may be spaced apart by 120 degrees. The projections 1648 enable the distal portion 1636 to be inserted into the canal of a long bone, such as a humerus, along thin outer edges of the projections 1348 such that contact with the bone in the canal is initially line contact. This makes insertion of the distal portion 1636 easier because there is less friction between the stem 1610 and the bone. While this provides for relatively minimal surface contact, the anchor member 1612 provides excellent securement, as discussed further below.

The proximal portion 1632 includes a distal region that can have the same or a similar form to that of a proximal region of the distal portion 1636. For example, the distal region of the proximal portion 1632 can have a central portion 1652 and one or a plurality of projections 1656. The proximal portion 1632 also can have one or more, e.g., three, projections. In one use, the stem 1610 is configured such that when implanted in a long bone, e.g. in the humerus, the proximal portion 1632 is disposed in the metaphysis of the bone. That is, the bone may be resected and thereafter, the distal portion 1636 can be advanced into the canal of the humerus, leaving the proximal portion 1632 in the metaphysis.

The projections 1656 can include similar or the same features discussed above in connection with the arms 128 projection from the proximal end of the anchor member 108. For example, the projections 1656 can include lateral spaces to receive and guide the threaded portion 1618 of the anchor member 1612 to the advanced position as shown in FIGS. 33 and 34. A gap also can be defined between the inner edges of the projections 1656 and an outer surface of the central portion 1652. The gap can accommodate the cylindrical portion 1619 of the anchor member 1612.

FIG. 33 shows that the stem 1610 of the implant 1600 includes a peripheral rim 1660 disposed about, e.g., surrounding the central portion 1652. The central portion 1652 can include a cylindrical member that is similar to the cylindrical member 130 in some embodiments. The peripheral rim 1660 preferably is coupled with each of the projections 1656. The peripheral rim 1660 can be configured to provide structural integrity to the projections. The peripheral rim 1660 has a plurality of tool features 1664 disposed about the periphery. In one embodiment, the tool features 1664 include three features equally spaced about the rim. The features can be used to advance the stem 1610 distally into the humerus after the humerus has been resected. In the event the stem 1610 is to be explanted the tool features 1664 can be engaged to dislodge the stem from the humerus.

The stem 1610 also includes a recess 1666 in which an articular component, such as a glenosphere, can be anchored. The recess 1666 is similar to the recess 104 discussed above in certain embodiments. The recess 1666 can be disposed in the central portion 1652. The central portion 1652 can have a tapered inner surface to provide a Morse taper connection with the articular component.

A method of implanting the implant 1600 can be similar to those discussed above. For example, the humerus can be resected at about the level of the metaphysis. Thereafter, access to the canal of the humerus can be provided or confirmed. After the access has been provided, the stem 1610 can be advanced through the resected surface of the humerus. For example, the tip 1640 can be urged through the resection plane and thereafter deeper into the humerus and further into the humeral canal. As the stem 1610 is advanced the projections 1648 engage the canal and act to center the distal portion 1636 of the stem in the canal. Advancement can be over a wire (in which case stem 1610 can be cannulated) as illustrated above in connection with FIGS. 16A-16C or freehand. After the stem 1610 is situated in the bone such that the peripheral rim 1660 is about at the plane of the resection, the surgeon can confirm placement. If appropriate, the surgeon may further advance the stem by impacting the stem into the bone. After the stem 1610 is properly placed, the anchor member 1612 can be advanced into the proximal portion 1632 of the stem as discussed above. For instance, a tool can engage the features 1620 and then apply a torque to engage the thread start(s) of the anchor member 1612 with the thread guiding features of the projections 1656. Full advancement of the anchor member 1612 can be confirmed by a positive stop of the cylindrical portion 1619 or by visible confirmation. The implant 1600 provides at least two independent modes or zones of securement. In one mode, the implant 1600 is secured in the cancellous bone of the humerus at the methaphysis by the threaded portion 1618 disposed within the proximal portion 1632 of the stem 1610. The proximal portion 1632 thus corresponds to one zone of securement. This mode and zone of securement are similar to that discussed above in connection with FIG. 26. A second mode of securement is provided by the distal portion 1636 of the stem 1610, wherein the stem can integrate with the bone matter surrounding the canal of the humerus. The distal portion 1636 thus corresponds to another zone of securement.

VI. Assemblies Having Porous Titanium Structures

Figure 36:
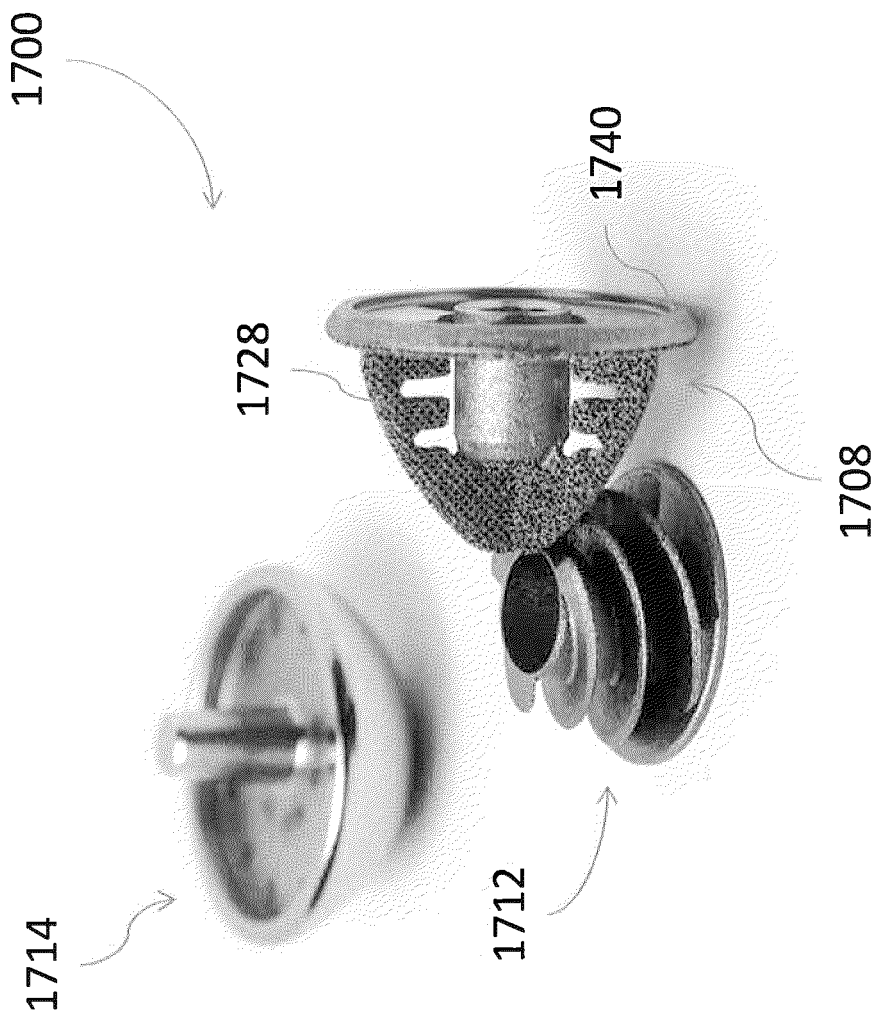
FIG. 36 is a view showing the components of a stemless humeral implant having one or more surfaces formed by additive manufacturing.
Figure 37:
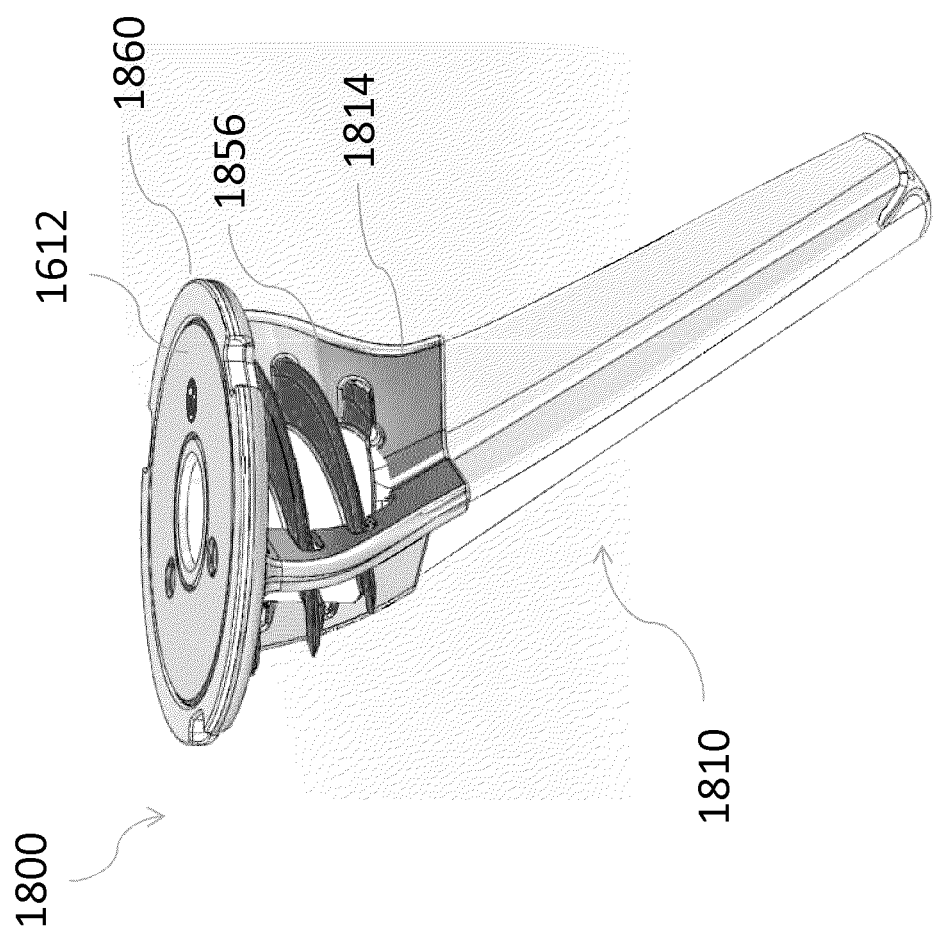
FIG. 37 is a top perspective view of another embodiment of a humeral implant with a stem, at least a portion of the implant being formed by additive manufacturing.

FIGS. 36-37 illustrate embodiments in which one or more components are at least partially formed by additive manufacturing. In certain additive manufacturing techniques a structure is assembled from components to create a three dimensional porous metal structure. The structure is formed by applying or creating individual layers that are later joined together through a suitable process, such as sintering. The layers can be laid down to progressively to form the three dimensional structure. FIG. 36 shows a humeral implant 1700 including a base member 1708, an anchor member 1712, and a humeral head 1714. In one embodiment, one or more features of the anchor member 1712 are formed by a process of additive manufacturing. More specifically, the spaced apart arms or projections 1728 of the anchor member 1708 and other structures that interact with the bone may be comprised of a unitary or monolithic porous titanium (Ti-6Al-4V). A bottom surface of a peripheral rim 1740 can be formed by additive manufacturing. As a result, the arms 1728 and/or the distal side of the rim 1740 can have a porous titanium structure that contacts a bone, e.g., a resected portion of the humerus. Porous titanium has a modulus similar to bone or of about 2.6 GPa. Matching the modulus of the porous titanium to the bone may enable better stress transfer from the implant to the bone, reducing wear on the bone, and increasing strength at the bone/implant interface.

The porous titanium structure can have a pore size from about 300 to about 800 μm, in embodiments from about 350 to about 750 μm, and in further embodiments from about 400 to about 700 μm. The porosity of the porous titanium structure may be optimized per implant geometry and anatomy and can be about 50%, 55%, 60%, 65%, 70%, 75%, and 80% porous.

Porous titanium can be formed by an additive manufacturing process, including a 3 dimensionally (3-D) printing process where layers of titanium are formed to create a three dimensional structure. The initial layer or layers are formed by such a method directly onto a portion or surface of the anchor member 1708. The 3-D printing process includes direct metal laser sintering onto the implant, more specifically, the anchor member 1708. First, blanks are formed by sintering titanium powder with a laser directly onto the substrate or anchor member. Next, in some techniques the blanks are machined, constructed or shaped to create a specific geometry of the bone-engaging surface. In some embodiments, the blanks are shaped to create either a stemless implant (as in FIG. 36) or an implant with a stem that can couple with the anchor member discussed herein (as in FIG. 37). Although the 3-D process is used herein to create stemmed or stemless members for implantation in the metaphysis and/or the canal of the humerus, other portions and surfaces of the implants may be formed with porous titanium, and are within the scope of this disclosure, including, but not limited to the anchor member or peripheral screws or portions thereof, central posts, and other structures that may be combined therewith. Once constructed, the porous structure and the solid substrate of baseplate comprise a monolithic, or one-piece structure. Alternatively, Electron Beam Melting (EBM) can be used to 3-D print a porous three dimensional structure on the implant.

FIG. 37 shows a humeral implant 1800 that is a modified embodiment of the humeral implant 1600. The implant 1800 includes an anchor member 1812 and a stem 1810. The stem 1810 includes a porous substrate 1814 that is disposed over a portion thereof. In one embodiment, the porous substrate is formed by additive manufacturing, e.g., 3-D printing as discussed above. The porous substrate 1814 can extend over a proximal portion of the stem 1810. For example, the porous substrate can be disposed over the metaphyseal bone contacting surfaces of the portion of the base not embedded in a canal of the humerus in use. The proximal portion that is porous titanium can include some or all of a plurality of projections 1856. The proximal portion that is porous titanium also can include some or all of a peripheral rim 1860, e.g., a distal bone engaging side of the rim 1860. The porous titanium substrate can also extend distally of the projections 1856 to a location at or just distal of the narrowing of the metaphysis.

In one embodiment, a kit is provided that includes a stemless humeral implant, such as the humeral shoulder assembly 100, and a stemmed humeral implant such as the implant 1600 or the implant 1800. By providing these components together in a kit a clinician can quickly adapt during a procedure from a stemless approach to a stemmed approach. For example, if the bone is not strong enough to support a stemless implant, the stemmed implant can be used without significant delay or use of much different components. In fact, the anchor member 112 could be used with either stem or stemless implants. Furthermore, some kits can include a variety of sizes of one or both of the stemless implant or the stemmed implant. For example, the base member 108 can come in different sizes to occupy an appropriate volume of the metaphysis of the specific humerus that is being treated by the surgeon. In some embodiments, the stem 1610 or the stem 1810 can be provided in a number of sizes such that the distal ends thereof reaches an appropriate depth in the canal of the humerus and/or fits in the canal with little or no preparation of the bone around the canal.

As used herein, the relative terms "proximal" and "distal" shall be defined from the perspective of the humeral shoulder assembly. Thus, distal refers the direction of the end of the humeral shoulder assembly embedded in the humerus, while proximal refers to the direction of the end of the humeral shoulder assembly facing the glenoid cavity.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A stemless humeral shoulder assembly, comprising:
a mounting member of a shoulder joint articular interface component; and
a base member including:
a first end including a peripheral rim that encircles the first end and an inner member having an outside surface and an inside surface, the inside surface including an inner periphery of the base member, the inner member configured to receive and thereafter be located around an outside surface of the mounting member when the mounting member is advanced into the inner member of the base member;
a second end configured to be embedded in a bone;
at least one flat surface extending between the peripheral rim and the inner member, the at least one flat surface disposed at an elevation distal of a proximal-most aspect of the peripheral rim; and
a plurality of spaced apart arms extending radially outward of the outside surface of the inner member, each of the plurality of spaced apart arms including (i) an outer edge and first and second lateral surfaces extending from the outer edge toward the outside surface of the inner member, (ii) a plurality of openings extending through the first and second lateral surfaces and open toward the outside surface of the inner member, and (iii) an inner edge spaced apart from the outside surface of the inner member,
wherein the first and second lateral surfaces of each of the plurality of spaced apart arms are separated by a thickness, each of the first and second lateral surfaces extending from the second end of the base member toward the first end of the base member, each of the first and second lateral surfaces having a width measured in a radial direction, the width of each of the first and second lateral surfaces being greater than the thickness.

2. The stemless humeral shoulder assembly of claim 1, wherein in each of the plurality of spaced apart arms, the plurality of openings are spaced apart along a longitudinal direction of a corresponding one of the each of the plurality of spaced apart arms.

3. The stemless humeral shoulder assembly of claim 1, wherein in each of the plurality of spaced apart arms, the plurality of openings are a plurality of slots.

4. The stemless humeral shoulder assembly of claim 1, wherein the plurality of spaced apart arms is three spaced apart arms.

5. The stemless humeral shoulder assembly of claim 1, wherein each of the plurality of openings intersects a longitudinal axis of the respective one of the plurality of spaced apart arms.

6. The stemless humeral shoulder assembly of claim 1, wherein the mounting member includes an anatomical joint interface configured to be received in the inner member.

7. The stemless humeral shoulder assembly of claim 1, wherein each of the plurality of spaced apart arms comprises a porous structure.

8. The stemless humeral shoulder assembly of claim 2, wherein the plurality of spaced apart arms and the peripheral rim form a monolithic structure.

9. The stemless humeral shoulder assembly of claim 2, wherein the inner member projects from the first end of the base member and through the second end of the base member.

10. The stemless humeral shoulder assembly of claim 1, wherein the plurality of spaced apart arms comprises three spaced apart arms extending between the first end and the second end of the monolithic base member, each of the three spaced apart arms comprising a porous structure.

11. The stemless humeral shoulder assembly of claim 1, wherein each of the three plurality of spaced apart arms comprises an arcuate outer edge.

12. The stemless humeral shoulder assembly of claim 1, wherein each of the plurality openings comprises a radially outer edge.

13. The stemless humeral shoulder assembly of claim 12, wherein the radially outer edges of the plurality of openings in each of the plurality of spaced apart arms are located at different distances from the inner edge of each of the plurality of spaced apart arms along a radial direction of each of the plurality of spaced apart arms.

14. The stemless humeral shoulder assembly of claim 1, wherein the first end of the base member comprises a plurality of arcuate openings.

15. The stemless humeral shoulder assembly of claim 14, wherein each of the plurality of arcuate openings comprises a first straight edge, a second straight edge, and an arcuate edge therebetween.

16. A stemless humeral shoulder assembly, comprising:
   a mounting member of a shoulder joint articular interface component; and
   a stemless humeral bone coupler, comprising:
   a first end comprising:
   a peripheral rim that defines an outer circumference of the stemless humeral bone coupler; and
   an inner member having an outside surface and an inside surface that defines a recess sized and configured to receive the mounting member;
   a second end configured to be embedded in humeral bone;
   a flat surface extending between the peripheral rim and the inner member, the at least one flat surface disposed at a distance distal of a proximal-most aspect of the peripheral rim; and
   a plurality of spaced apart arms extending radially outward of the inner member, each of the plurality of spaced apart arms comprising:
   an outer edge,
   an inner edge, and
   first and second lateral surfaces extending from the inner edge toward the outer edge and extending from the second end of the base member toward the first end of the base member,
   wherein the inner edge that is spaced apart from the inner member such that an opening is defined between the inner member and the inner edge, the opening extending from the first lateral face to the second lateral face,
   wherein the first and second lateral surfaces of each of the plurality of spaced apart arms are separated by a thickness and have a width extending from the inner edge toward the outer edge in a radial direction, and
   wherein the width of each of the first and second lateral surfaces is greater than the thickness.

17. The stemless humeral shoulder assembly of claim 16, wherein the plurality of spaced apart arms includes four arms.

18. The stemless humeral shoulder assembly of claim 16, wherein the inner member and the plurality of spaced apart arms comprise a unitary structure.

19. The stemless humeral shoulder assembly of claim 18, the inner member and the plurality of spaced apart arms are configured to be advanced into the humeral bone.

20. The stemless humeral shoulder assembly of claim 16, wherein the inner member is cylindrical.

21. The stemless humeral shoulder assembly of claim 16, wherein at least the plurality of arms of the stemless humeral bone coupler comprise a porous structure.

22. The stemless humeral shoulder assembly of claim 21, wherein at least the plurality of arms of the stemless humeral bone coupler comprise titanium.

23. A kit comprising:
   the stemless humeral shoulder assembly of claim 16;
   a pin configured to guide a reaming instrument; and
   a tool comprising radial projections configured to create channels in cancellous bone, each channel configured to receive one of the arms of the plurality of arms.

* * * * *